United States Patent
Sakaguchi

(10) Patent No.: US 10,765,751 B2
(45) Date of Patent: *Sep. 8, 2020

(54) PH SENSITIVE CARRIER AND PREPARATION METHOD THEREOF, AND PH SENSITIVE DRUG AND PH SENSITIVE DRUG COMPOSITION EACH CONTAINING THE CARRIER, AND METHOD FOR TREATING OR PREVENTING DISEASES USING THE SAME

(71) Applicant: TERUMO KABUSHIKI KAISHA, Shibuya-ku, Tokyo (JP)

(72) Inventor: Naoki Sakaguchi, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 32 days.

This patent is subject to a terminal disclaimer.

(21) Appl. No.: 15/816,513

(22) Filed: Nov. 17, 2017

(65) Prior Publication Data
US 2018/0104343 A1    Apr. 19, 2018

Related U.S. Application Data

(60) Division of application No. 15/007,830, filed on Jan. 27, 2016, now abandoned, which is a continuation of
(Continued)

(30) Foreign Application Priority Data

May 31, 2012    (JP) .................................. 2012-124796

(51) Int. Cl.
*A61K 47/24*    (2006.01)
*A61K 9/107*    (2006.01)
(Continued)

(52) U.S. Cl.
CPC ............ *A61K 47/24* (2013.01); *A61K 9/1075* (2013.01); *A61K 9/1272* (2013.01); *A61K 38/00* (2013.01);
(Continued)

(58) Field of Classification Search
None
See application file for complete search history.

(56) References Cited

U.S. PATENT DOCUMENTS 4,158,707 A  *  6/1979   Steffen ................. A61K 9/1075
                                                        514/221
4,882,164 A      11/1989  Ferro et al.
(Continued)

FOREIGN PATENT DOCUMENTS

CN          102068410 A       5/2011
CN          102106821 A       6/2011
(Continued)

OTHER PUBLICATIONS

Andreev, O. A. et al., Mechanism and Uses of a Membrane Peptide That Targets Tumors and Other Acidic Tissues In Vivo, PNS, vol. 104, No. 9, pp. 7893-7898 (May 8, 2007).
(Continued)

*Primary Examiner* — Bethany P Barham
*Assistant Examiner* — Barbara S Frazier
(74) *Attorney, Agent, or Firm* — Buchanan Ingersoll & Rooney PC

(57) ABSTRACT

A method for treating tumor or inflammation in a patient in need thereof by administering a pH sensitive drug which includes a pH sensitive carrier including at least one amphipathic substance, and a physiologically active substance supported in the pH sensitive carrier to induce the pH sensitive carrier to develop a membrane disruptive function and to deliver the physiologically active substance to the
(Continued)

site. The pH sensitive carrier can include at least one of deoxycholic acid, cholic acid, ursodeoxycholic acid, chenodeoxycholic acid, hyodeoxycholic acid, C27 bile acid, glycodeoxycholic acid, glycyrrhizic acid, glycyrrhetinic acid and salts thereof, and the amphipathic substance can include at least one of a phosphatidylcholine having 10 to 12 carbon atoms, a polyoxyethylene sorbitan monofatty acid ester having 12 to 18 carbon atoms, a sorbitan fatty acid ester having 16 to 18 carbon atoms, glycerol monooleate, glycerol dilaurate, glycerol distearate, glycerol dioleate, polyoxyethylene castor oil and α-tocopherol.

10 Claims, 22 Drawing Sheets
(8 of 22 Drawing Sheet(s) Filed in Color)

Related U.S. Application Data application No. 13/907,301, filed on May 31, 2013, now Pat. No. 9,248,192.

(60) Provisional application No. 61/670,332, filed on Jul. 11, 2012.

(51) Int. Cl.
*A61K 9/127* (2006.01)
*A61K 38/00* (2006.01)
*A61K 38/02* (2006.01)
*A61K 47/14* (2017.01)
*A61K 47/28* (2006.01)
*A61K 47/10* (2017.01)

(52) U.S. Cl.
CPC ............ *A61K 38/02* (2013.01); *A61K 47/10* (2013.01); *A61K 47/14* (2013.01); *A61K 47/28* (2013.01)

(56) References Cited

U.S. PATENT DOCUMENTS

| | | | |
|---|---|---|---|
| 5,643,599 A | 7/1997 | Lee et al. | |
| 5,711,964 A | 1/1998 | Dattagupta et al. | |
| 5,739,271 A | 4/1998 | Sridhar et al. | |
| 5,756,352 A | 5/1998 | Sridhar et al. | |
| 5,759,445 A * | 6/1998 | Yamamoto ............ | G01N 33/92 252/408.1 |
| 5,759,519 A | 6/1998 | Sridhar et al. | |
| 5,851,548 A | 12/1998 | Dattagupta et al. | |
| 6,258,377 B1 | 7/2001 | New et al. | |
| 6,333,046 B1 | 12/2001 | Sakai et al. | |
| 6,352,996 B1 | 3/2002 | Cao et al. | |
| 6,630,169 B1 * | 10/2003 | Bot .................. | A61K 9/0043 424/489 |
| 2005/0232952 A1 | 10/2005 | Lambert et al. | |
| 2007/0298093 A1 | 12/2007 | Konur et al. | |

FOREIGN PATENT DOCUMENTS

| | | |
|---|---|---|
| JP | S52-57313 A | 5/1977 |
| JP | 63-201133 A | 8/1988 |
| JP | 4-360832 A | 12/1992 |
| JP | 11-507031 A | 6/1999 |
| JP | 2000-515130 A | 11/2000 |
| JP | 2001-515455 A | 9/2001 |
| JP | 2005-523295 A | 8/2005 |
| JP | 2006-34211 A | 2/2006 |
| JP | 2007-515451 A | 6/2007 |
| WO | WO 01/08663 A2 | 2/2001 |
| WO | WO 2008/040799 A2 | 4/2008 |

OTHER PUBLICATIONS

Simões, S. et al., "On the Formulation of pH-Sensitive Liposomes with Long Circulation Times", Elsevier, Advanced Drug Delivery Reviews 56, pp. 947-965 (2004).
International Search Report (Forms PCT/ISA/220 and PCT/ISA/210) and the Written Opinion of International Searching Authority (Form PCT/ISA/237) dated Jul. 16, 2013, by the International Bureau of WIPO in International Application No. PCT/JP2013/065126. (8 pages).
Li et al., "Effects of Phospholipid Chain Length, Concentration, Charge, and Vesicle Size on Pulmonary Insulin Absorption", Pharm Res., 13(1), pp. 76-79 (1996).
Written Opinion and Preliminary Report on Patentability issued in corresponding International Application No. PCT/JP2013/065126 dated Dec. 11, 2014 (12 pages).
Almog et al.: "Kinetic and Structural Aspects of Reconstitution of Phosphatidylcholine Vesicles by Dilution of Phosphatidylcholine-Sodium Cholate Mixed Micelles," Biochemisty, vol. 25, No. 9, May 1, 1986, pp. 2597-2605, XP55211260.
Lee et al.: "Recent progress in tumor pH targeting nanotechnology," Journal of Controlled Release, Elsevier, Amsterdam, NL, vol. 132, No. 3, Dec. 18, 2008, pp. 164-170, XP025714815.
Extended Search Report issued by the European Patent Office in corresponding European Patent Application No. 13797114.9 dated Oct. 1, 2015.
Office Action issued by the Russian Patent Office in corresponding Russian Patent Application No. 2014152695 dated Apr. 17, 2017 (12 pages including partial English translation).
Notification of Reasons for Refusal issued by the Japanese Patent Office in corresponding Japanese Patent Application No. 2014-518746 dated Aug. 8, 2017 (13 pages including partial English translation).
Dominska et al.: "Breaking down the barriers: siRNA delivery and endosome escape", Journal of Cell Science, 2010, vol. 123, pp. 1183-1189 (7 pages).
Karanth et al.: "pH-Sensitive liposomes-principle and application in cancer therapy", Journal of Pharmacy and Pharmacology, 2007, vol. 59 (4), pp. 469-483 (15 pages).
Office Action issued by the Canadian Intellectual Property Office in corresponding Canadian Patent Application No. 2,875,208 dated Mar. 13, 2017 (4 pages).

* cited by examiner

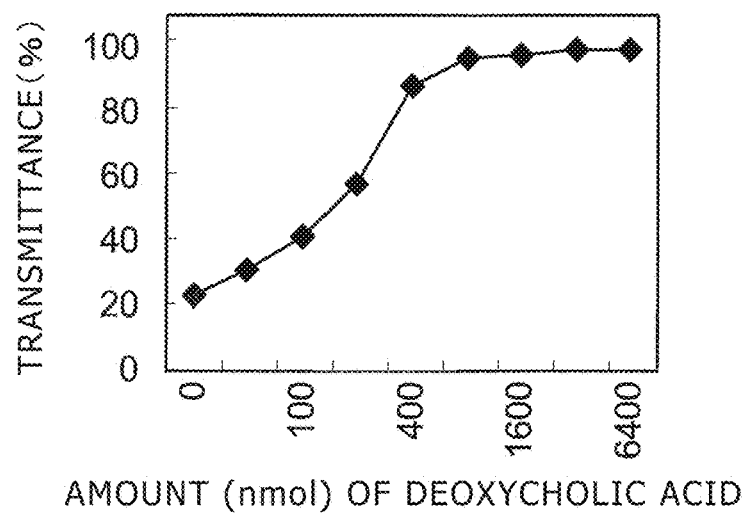
FIG.2C
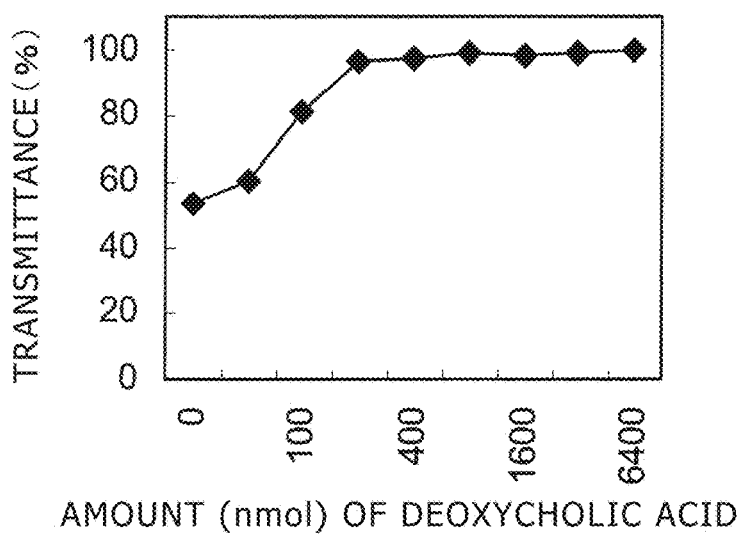
FIG.2D
FIG.3
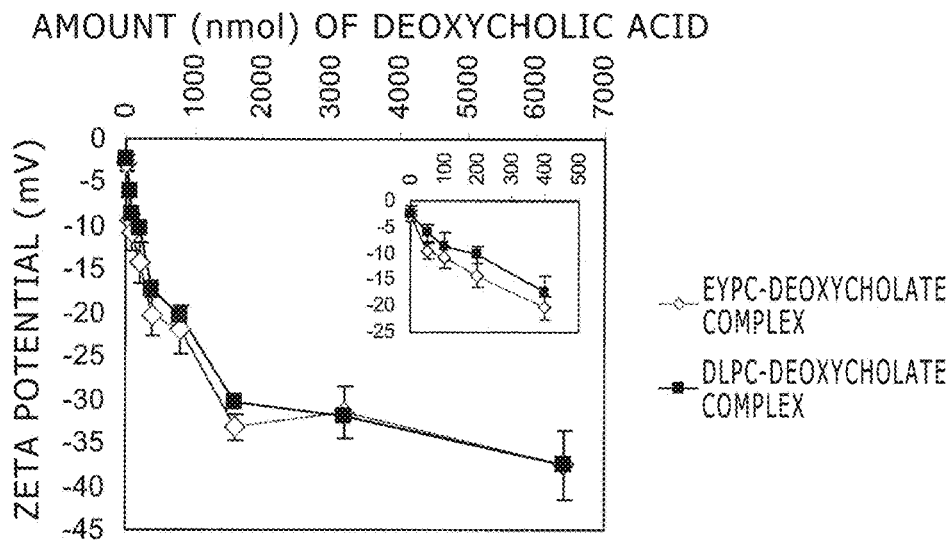

(A)

(B)

(A)

(B)

(A)

(B)

(A)

(B)

(A)

(B)

(A)

(B)

(A)

(B)

(C)

(D)

(E)

(F)

(G)

(H)

(I)

(J)

(K)

(L)

(M)

(N)

(O)

(P)

(Q)

(R)

(S)

(T)

(U)

(V)

(W)

(X)

(Y)

(Z)

(AA)

(AB)

PH SENSITIVE CARRIER AND PREPARATION METHOD THEREOF, AND PH SENSITIVE DRUG AND PH SENSITIVE DRUG COMPOSITION EACH CONTAINING THE CARRIER, AND METHOD FOR TREATING OR PREVENTING DISEASES USING THE SAME

RELATED APPLICATIONS

This application is a divisional of U.S. application Ser. No. 15/007,830 filed on Jan. 27, 2016, which is a continuation of U.S. application Ser. No. 13/907,301 filed on May 31, 2013, and is now U.S. Pat. No. 9,248,192, which claims priority to U.S. Application No. 61/670,332 filed on Jul. 11, 2012 and Japanese Patent Application No. 2012-124796 filed on May 31, 2012, the entire contents of which are incorporated herein by reference.

TECHNICAL FIELD

Disclosed are a pH sensitive carrier and a preparation method thereof, a pH sensitive drug and a pH sensitive drug composition each containing the carrier, and a method for treating or preventing a disease using the same. More particularly disclosed area pH sensitive carrier which is useful for DDS (Drug Delivery System) and is capable of developing a membrane disruptive function promoting effect in response to a weakly acidic environment, and a preparation method thereof, and a pH sensitive drug and a pH sensitive drug composition each containing the carrier, and a method for treating or preventing a disease using the same.

BACKGROUND DISCUSSION

In recent years, extensive studies have been made on DDS carriers (carriers) for delivering a physiologically active substance to an intended site in a required amount. Attention has now been paid to a stimuli responsive carrier from the standpoint of an improvement in accumulation and the selection of the delivery site, and many reports have been made on studies concerned with external stimulation with heat, a magnetic field or the like, and in vivo stimulation such as of molecular recognition, pH change, enzymatic reaction or the like. Among them, a carrier which is sensitive to a weakly acidic pH has been investigated for a long time.

For instance, as a pH sensitive carrier responsive to a weakly acidic environment, there are known pH sensitive liposomes wherein various types of pH sensitive elements such as PHC (Palmitoyl Homocysteine), oleic acid, CHEMS (Cholesteryl Hemisuccinate) and the like are added to liposomes containing PE (Phosphatidylethanolamine) (S. Simoes et al., Adv. Drug Deli. Rev. 2004 56 947-965 and the like). Recently, there have been reported studies, for the purpose of enhancing function, on novel synthetic materials such as PEAA (Poly(2-ethylacrylic Acid)), SucPG (Succinylated Poly(glycidol)) and the like, synthetic peptides such as GALA, pHLIP (pH Low Insertion Peptide) and the like, biodegradable materials such as PLGA (Poly(Lactic-co-glycolic Acid)) and the like, and VLP (Virus Like Particle) and Virosome using a pH sensitive viral component.

The pH sensitive carrier is expected to efficiently deliver a physiologically active substance to a site such as of a tumor or inflammation where a pH lowers in a living body (Reshetnyak et al., PNAC 2007 vol. 104, 19, 7893-7898) or to deliver to the cytosol by utilizing the acidification of vesicles after being taken up by cells.

With respect to the delivery to the cytosol by using the acidification of vesicles, it has been found that migration of a drug to the cytosol is facilitated by promoting membrane fusion of a carrier upon delivery to endosomes, and a DDS carrier of a peptide derivative having a pH sensitive site whose structure is changed in response to the pH, a membrane fusion site and a transmembrane site has been reported in Japanese Patent Laid-open No. 2006-34211.

Such a delivery of a physiologically active substance to vesicles is utilizable in various fields and is thus a technique that is in demand. For instance, delivery of RNA or DNA to the cytosol enables gene therapy, and it has been expected to induce CTL (Cytotoxic T Lymphocyte) by the delivery of an antigen to the cytosol. The cytosolic delivery of a low molecular weight anticancer agent has been reported as having an improved effect on activity, and its application to a novel type of drug for use as an intracellularly targeted drug has been considered. The cytosolic delivery of a physiologically active substance is a major problem to solve in these fields and is thus desirable.

In view of the fact that there is a successful case of delivering pHLIP having sensitivity to a pH of not higher than 6 to an acidosis site as described in Reshetnyak et al., PNAS 2007 vol. 104, 19, 7893-7898 or a pH arriving within endosomes in the vicinity of 4 as described in S. Simoes et al., Adv. Drug Deli. Rev. 2004 56 947-965, it is required that a pH-sensitive carrier have high sensitivity between neutral pH and a pH of 4. This is described in many documents. It is further important from the standpoint of practical use that the carrier is made of a safe material.

SUMMARY

Many pH sensitive liposomes and biodegradable materials have a problem in that they exhibit sensitivity at too low a pH or have only an inadequate function. Moreover, with respect to a method of directly modifying a pH sensitive material, there is a concern that the activity of a physiologically active substance can decrease. A novel type of synthetic material or a viral component would raise concerns from the standpoint of safety.

BRIEF DESCRIPTION OF THE DRAWINGS

The patent or application contains at least one drawing executed in color. Copies of this patent or patent application publication with color drawing(s) will be provided by the Office upon request and payment of the necessary fee.

FIG. 2C is a graph showing a transmittance of dispersions containing EYPC and deoxycholic acid.

FIG. 2D is a graph showing a transmittance of dispersions containing DLPC and deoxycholic acid.

FIG. 3 is a graph showing a zeta potential of a dispersion containing EYPC and deoxycholic acid in relation to the amount of deoxycholic acid.

DETAILED DESCRIPTION

Figure 1A:
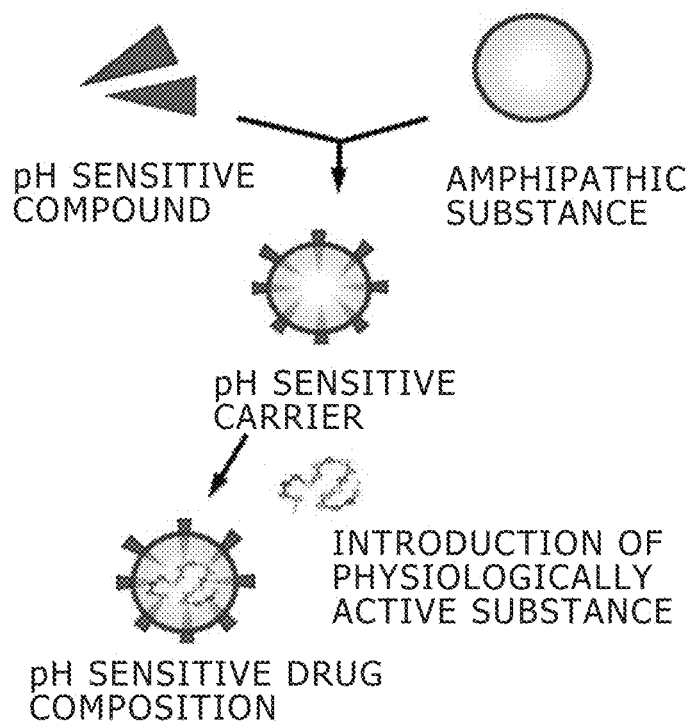
FIG. 1A is a schematic view of a drug including an illustrative pH sensitive carrier and a physiologically active substance supported with the carrier.

Accordingly, an illustrative aspect provides a pH sensitive carrier which can serve as a carrier for physiologically active substance and is able to develop a membrane disruptive function promoting effect in response to a weakly acidic environment and its preparation method, and also provides a pH sensitive drug and a pH sensitive drug composition each containing the carrier, and a method for treating or preventing a disease using the same.

Disclosed are the following illustrative aspects.

(1) a pH sensitive carrier which includes at least one pH sensitive compound selected from the group consisting of deoxycholic acid, cholic acid, ursodeoxycholic acid, chenodeoxycholic acid, hyodeoxycholic acid, C27 bile acid, glycodeoxycholic acid, glycyrrhizic acid, glycyrrhetinic acid and salts thereof and at least one amphipathic substance selected from the group consisting of a phosphatidylcholine having 10 to 12 carbon atoms, a polyoxyethylene sorbitan monofatty acid ester having 12 to 18 carbon atoms, a sorbitan fatty acid ester having 16 to 18 carbon atoms, glycerol monooleate, glycerol dilaurate, glycerol distearate, glycerol dioleate, polyoxyethylene castor oil and α-tocopherol and which is capable of developing a membrane disruptive function promoting effect.

(2) The pH sensitive carrier set forth in (1) above, wherein the pH sensitive compound and the amphipathic substance form micellar particles.

(3) The pH sensitive carrier set forth in (2) above, wherein the particle size is 10 to 200 nm.

(4) The pH sensitive carrier set forth in any one of (1) to (3) above, wherein the pH sensitive compound is present in an amount of not less than 10 moles per 100 moles of the amphipathic substance.

(5) The pH sensitive carrier set forth in any one of (1) to (4) above, wherein when a leakage of the pH sensitive compound alone in a leaching test is taken as La, a leakage of the amphipathic substance alone taken as Lb, a leakage of the pH sensitive carrier taken as Lc, leakages at a pH of 7.4, respectively, taken as $Lc_{7.4}$, $La_{7.4}$ and $Lb_{7.4}$, and leakages at a pH of 5.0 or 4.5, respectively, taken as $Lc_x$, $La_x$ and $Lb_x$, Δ represented by the following equation (1) is not smaller than 5 and Δ' represented by the following equation (2) is not smaller than 5.

$$\Delta = (Lc_x - Lc_{7.4}) - (La_x - La_{7.4}) \quad \text{Equation (1)}$$

$$\Delta' = Lc_x - (La_x + Lb_x) \quad \text{Equation (2)}$$

(6) A pH sensitive drug, wherein the pH sensitive carrier defined in any one of (1) to (5) above supports a physiologically active substance.

(7) The pH sensitive drug set forth in (6) above, wherein the physiologically active substance is made of a protein or a peptide.

(8) A pH sensitive drug composition including the pH sensitive carrier and the physiologically active substance, defined in any one of (1) to (5) above.

(9) The pH sensitive drug composition set forth in (8) above, wherein the physiologically active substance is a protein or a peptide.

(10) A method for preparing a pH sensitive carrier which is capable of developing a membrane disruptive function promoting effect, the method including associating at least one pH sensitive compound selected from the group consisting of deoxycholic acid, cholic acid, ursodeoxycholic acid, chenodeoxycholic acid, hyodeoxycholic acid, C27 bile acid, glycodesoxycholic acid, glycyrrhizic acid, glycyrrhetinic acid and salts thereof and at least one amphipathic substance selected from the group consisting of a phosphatidylcholine having 10 to 12 carbon atoms, a polyoxyethylene sorbitan monofatty acid ester having 12 to 18 carbon atoms, a sorbitan fatty acid ester having 16 to 18 carbon atoms, glycerol monooleate, glycerol dilaurate, glycerol distearate, glycerol dioleate, polyoxyethylene castor oil and α-tocopherol.

(11) A method for treating or preventing a disease, the method including collecting cells from a subject, culturing the collected cells in a medium containing the pH sensitive drug set forth in (6) or (7) above and/or the pH sensitive drug composition set forth in (8) or (9) above, and administering the thus cultured cells to the subject.

In an illustrative embodiment, provided is a pH sensitive carrier which includes at least one pH sensitive compound selected from the group consisting of deoxycholic acid, cholic acid, ursodeoxycholic acid, chenodeoxycholic acid, hyodeoxycholic acid, C27 bile acid, glycodesoxycholic acid, glycyrrhizic acid, glycyrrhetinic acid and salts thereof and at least one amphipathic substance selected from the group consisting of a phosphatidylcholine having 10 to 12 carbon atoms, a polyoxyethylene sorbitan monofatty acid ester having 12 to 18 carbon atoms, a sorbitan fatty acid ester having 16 to 18 carbon atoms, glycerol monooleate, glycerol dilaurate, glycerol distearate, glycerol dioleate, polyoxyethylene castor oil and α-tocopherol and is capable of developing a membrane disruptive function promoting effect. The pH sensitive carrier may be sometimes hereinafter referred to as "carrier," "associated product" or "complex." As used herein, the "number of carbon atoms" of the described amphipathic substance means the number of carbon atoms of a fatty acid moiety (acyl group) serving as the hydrophobic site of the amphipathic substance.

In an illustrative embodiment, there can be provided a pH sensitive carrier which is superior in safety and has superior pH sensitivity.

As used herein, the term "membrane disruptive function" means a function of causing leakage in a leaching test. The leaching test used in this specification is one wherein liposomes (dispersion) including an aqueous solution containing a quenching substance and a fluorescent substance, and a pH sensitive carrier or an evaluation sample dispersion such as of a pH sensitive compound alone or an amphipathic compound alone is added to an aqueous solution whose pH is adjusted to a given level, followed by incubating the aqueous solution at 37° C. for 90 minutes or 30 minutes and measuring the fluorescence of the aqueous solution. According to this method, a fluorescent substance dissolved or leached out from the liposomes can be measured, from which the liposome membrane disruptive function of the pH sensitive carrier can be confirmed. It will be noted that the leaching test will be described in more detail in examples appearing hereinafter.

As used herein, the term "to develop a membrane disruptive function promoting effect" means to satisfy both of requirements (1) and (2): (1) in the leaching test, a leakage at a given pH that is lower than a physiological pH increases compared to a leakage at the physiological pH and the increase is greater than the increase where the pH sensitive compound alone is subjected to the test; and (2) in the leaching test at a given pH less than the physiological pH, a leakage at the time when a pH sensitive compound and an amphipathic substance forms a complex (pH sensitive carrier) is greater than the sum of a leakage of the pH sensitive compound alone and a leakage of the amphipathic substance alone. More particularly, to develop a membrane disruptive function promoting effect means that in leaching tests at a pH of 7.4 and at a pH of 5.0 or 4.5, a leakage Lc of a pH sensitive carrier (a complex of a pH sensitive compound and an amphipathic substance) satisfies both the following relations with a leakage La of the pH sensitive compound alone and a leakage Lb of the amphipathic substance alone. More particularly, the above (1) is represented by the following formula (1) and the above (2) is represented by the following formula (2). It is to be noted that in the following formulas, leakages at a pH of 7.4 are, respectively, denoted by $Lc_{7.4}$, $La_{7.4}$ and $Lb_{7.4}$, and leakages at a pH of 5.0 or 4.5 are, respectively, denoted by $Lc_x$, $La_x$ and $Lb_x$.

$$\Delta = (Lc_x - Lc_{7.4}) - (La_x - La_{7.4}) > 0 \quad \text{Formula (1)}$$

$$\Delta' = Lc_x - (La_x + Lb_x) > 0 \quad \text{Formula (2)}$$

In the above formula (1), $\Delta$ should exceed 0 and is typically not less than 5, for example not less than 10 and for example not less than 30. In the above formula (2), $\Delta'$ typically exceeds 0, for example not less than 5, for example not less than 10, for example not less than 15.

An illustrative pH sensitive carrier is one whose $\Delta$ and $\Delta'$ are, respectively, not less than 5 in the above formulas (1) and (2) and which contains a bile acid and a lipid. Another illustrative pH sensitive carrier is one whose $\Delta$ and $\Delta'$ in the formulas (1) and (2) are, respectively, not less than 5 and which contains glycyrrhizic acid or glycyrrhetinic acid and a lipid.

As used herein, the term "physiological pH" means a pH in a normal tissue or normal body fluid. The physiological pH is generally at 7.4 and may differ, more or less (±0.10), depending on the normal tissue or normal body fluid. The term "a given pH less than a physiological pH" means a pH less than 7.4, for example a pH of not less than 3.0 to less than 7.4, for example a pH of not less than 4.0 to less than 7.3, for example a pH of not less than 4.5 to less than 7.0.

Although how the pH sensitive carrier develops a membrane disruptive function promoting effect is not clear, this is assumed in the following way. It will be noted that this theory should not be construed as any limitation.

It is considered that the pH sensitive carrier is formed by association of a pH sensitive compound and an amphipathic substance in an aqueous solution at a pH level not lower than a physiological pH.

In FIG. 1A, a pH sensitive carrier and a pH sensitive drug wherein the pH sensitive carrier supports a physiologically active substance therewith are schematically shown. As shown in FIG. 1A, it is considered that the pH sensitive carrier is formed by association of a pH sensitive compound with an amphipathic substance at a hydrophobic site thereof. The pH sensitive carrier can include a physiologically active substance therein. It will be noted that the form of the association of the pH sensitive carrier is based on assumption and thus, the pH sensitive carrier is not limited to this form of association. The form of support of the pH sensitive carrier is based on assumption and thus, the pH sensitive carrier should not be construed as limited to this form of support.

It is considered that the pH sensitive carrier has a membrane disruptive function promoting effect as a result that if an ambient environment becomes a pH lower than a physiological pH, the pH sensitive carrier changes in association form between the pH sensitive compound and the amphipathic substance. For instance, it is assumed that if the pH becomes lower than a physiological pH in a system where a pH sensitive carrier and a biological membrane (e.g., a cell membrane, a vesicular membrane or the like) exist, the association form of the pH sensitive carrier changes. After contact with the biological membrane, the structural change of the biological membrane is caused by the change of the association form. More particularly, the pH sensitive carrier causes the structural change of the biological membrane. This is considered as follows: when the pH changes to weak acidity, the pH sensitive compound in the pH sensitive carrier becomes unstable in the structure of the carrier, with the result that the pH sensitive carrier is rearranged with the biological membrane existing in the system, thereby developing the membrane disruptive function promoting effect. In other words, it is considered that the pH sensitive compound is a molecule that acts to change the solubility toward the hydrophobic association through protonation when the pH becomes weakly acidic. More particularly, the hydrophobic association involving the pH sensitive compound is in response to a weakly acidic environment and is able to develop the function. As used herein, the term "membrane disruption" refers to a change in such a membrane structure and may not always involve separation or decomposition of all of the membrane constituent components. Owing to the occurrence of such "membrane disruption, the components contained inside the biological membrane (e.g., endosome) leach to outside of the biological membrane.

The pH sensitive carrier typically is one whose leakage, determined by the leaching test, is less than 20% at a pH of 7.4 and is larger than 20% at a pH of 4.0. For example, the leakage in the leaching test is less than 20% at a pH of 6.5 and larger than 20% at a pH of 4.0. Moreover, the leakage at a pH of 7.4 or 6.5 can be not larger than 15%, for example not larger than 10%. The leakage at a pH of 4.0 is typically not less than 40%, for example not less than 50%. When the leakage of the pH sensitive carrier is set as defined above, the development of the membrane disruptive function promoting effect at a weakly acidic pH can be better shown.

The pH sensitive carrier is also able to develop a membrane fusion function promoting effect along with the membrane disruptive function promoting effect.

As used herein, the term "membrane fusion function" means a function of causing membrane fusion in a membrane fusion test. The membrane fusion test used herein is a test wherein a liposome (dispersion) incorporating two types of fluorescent substances in a bimolecular membrane, and a pH sensitive carrier or an evaluation sample dispersion such as of a pH sensitive compound alone, an amphipathic substance alone or the like are added to an aqueous solution adjusted to a given pH, and the resulting aqueous solution is incubated at 37° C. for 60 minutes, followed by measurement of the fluorescence of the aqueous solution. According to this method, variations in energy resonance transfer of the two types of fluorescent substances incorporated in the liposome can be measured, thus confirming the membrane fusion function of the pH sensitive carrier. It is to be noted that the membrane fusion test is described in detail in examples appearing hereinafter.

As used herein, the term "to develop a membrane fusion function promoting effect" means that, in the membrane fusion test, a fusion rate at a given pH less than a physiological pH increases compared to a fusion rate at the physiological pH and the increase is larger than compared to where a pH sensitive compound alone is used for the test. More particularly, to develop the membrane fusion function promoting effect means that in the membrane fusion tests at pHs of 7.4 and 5.0, a fusion rate Rc (%) of a pH sensitive carrier (a complex of a pH sensitive compound and an amphipathic substance) and a fusion rate Ra (%) of the pH sensitive compound alone satisfy the relationship of the following Formula (3). It will be noted that the fusion rates at a pH of 7.4 are, respectively, represented by $Rc_{7.4}$ and $Ra_{7.4}$ and the fusion rates at a pH of 5.0 are, respectively, represented by $Rc_x$ and $Ra_x$.

$$\Delta R = (Rc_x - Rc_{7.4}) - (Ra_x - Ra_{7.4}) > 0 \quad \text{Formula (3)}$$

In the formula (3), ΔR should exceed 0, for example not less than 2, for example not less than 5, for example not less than 10.

An illustrative pH sensitive carrier is one whose OR in the above formula (3) is not less than 2 and which contains a bile acid and a lipid.

The pH sensitive carrier develops the membrane fusion function promoting effect at a weakly acidic pH (at a given pH lower than a physiological pH). Although this mechanism is not fully understood, it is assumed that such a mechanism as set out with respect to the membrane disruptive function promoting effect is applied. It will be noted that this assumption should not be construed as a limitation.

In particular, it is assumed that the pH sensitive carrier changes in association form between the pH sensitive compound and the amphipathic substance if an ambient environment becomes less than the physiological pH, so that membrane fusion occurs due to the rearrangement with a biological membrane existing in the system. On this occasion, the rearrangement ascribed to the fusion occurs among affinity components themselves with no affinity for biological membrane, or low affinity components (e.g., a physiologically active substance) are excluded or released from the rearranged membrane.

Generally, an extracellular molecule is surrounded by an endosome that is a sort of biological membrane and taken up in a cell. Thereafter, the pH inside the endosome is lowered by the action of a proton pump. Moreover, the endosome fuses with a lysosome containing a hydrolase, so that the extracellular molecule is decomposed. Hence, most of the extracellular molecules are not delivered to within the cellular cytosol.

Figure 1B:
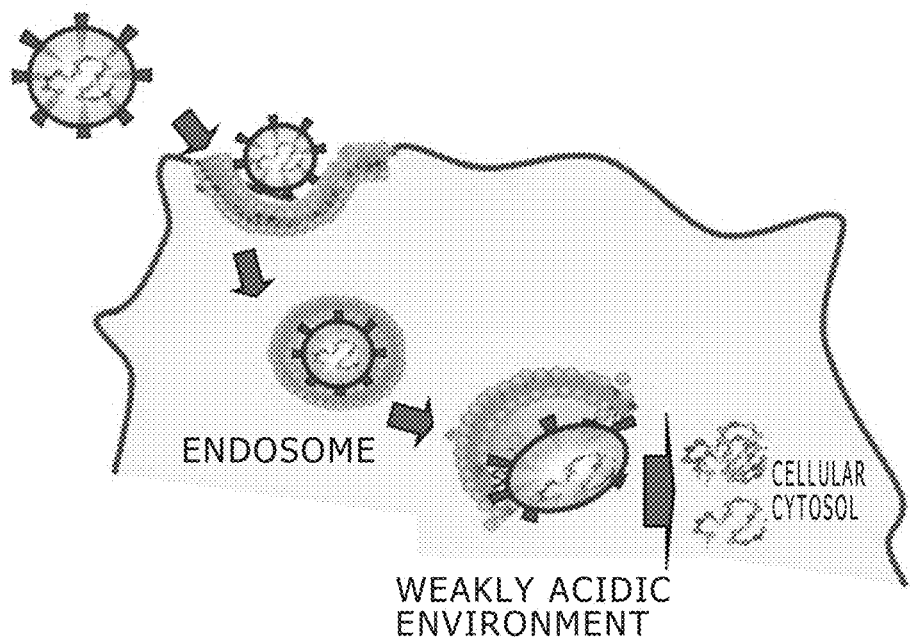
FIG. 1B is a schematic view showing delivery of a physiologically active substance supported with a pH sensitive carrier to cellular cytosol as a result of the development of membrane disruptive function promoting effect of the pH sensitive carrier in case where a pH sensitive drug is used.
Figure 1C:
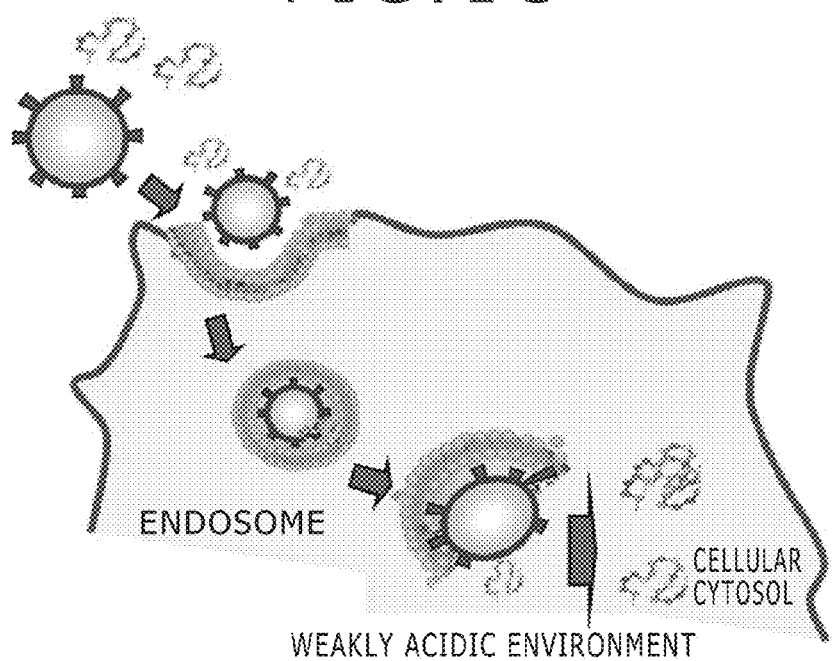
FIG. 1C is a schematic view showing delivery of a physiologically active substance mixed with a pH sensitive carrier to cellular cytosol as a result of the development of membrane disruptive function promoting effect of the pH sensitive carrier in the case where a pH sensitive drug composition is used.

In contrast thereto, the pH sensitive carrier (pH sensitive drug or pH sensitive drug composition) is surrounded by an endosome and taken up in a cell as shown in FIGS. 1B and 1C, thereby leading likewise to an environment where the pH is lower. In association with the lowering (acidification) of pH, the pH sensitive compound causes the pH sensitive carrier to be instabilized, so that membrane rearrangement between the endosome and the pH sensitive carrier occurs thereby causing the membrane disruptive function (sometimes, the membrane disruptive function occurring along with the membrane fusion function in some cases) caused by the pH sensitive carrier.

As exemplified in FIGS. 1B and 1C, the use of the pH sensitive carrier permits a physiologically active substance and the like to be delivered into the cellular cytosol. More particularly, when a pH sensitive drug is used, a physiologically active substance (FIG. 1B) included in the pH sensitive carrier, or a physiologically active substance (FIG. 1C) used along with the pH sensitive carrier with the case of using a pH sensitive drug composition is surrounded with an endosome along with the pH sensitive carrier and taken up in the endosome. When the pH inside the endosome is lowered, the pH sensitive compound causes the pH sensitive carrier to be unstable thereby causing the membrane rearrangement between the endosome and the pH sensitive carrier. As a consequence, the membrane disruption of the endosome with the pH sensitive carrier takes place. In this way, the physiologically active substance is released to the cellular cytosol. That is, delivery into the cellular cytosol can be realized without involving decomposition of the physiologically active substance.

An illustrative pH sensitive carrier can form a complex containing a pH sensitive compound and an amphipathic substance in an aqueous medium. The form of the complex is not critical, and the pH sensitive compound and the amphipathic substance may form a membrane or part or all of the pH sensitive compound may be embedded in the structure formed of the amphipathic substance through association. In the illustrative pH sensitive carrier, the pH sensitive compound and the amphipathic substance can form micellar particles, or a particulate carrier such as of liposome may be formed. Where the EPR (Enhanced Permeation and Retention) effect and endocytosis are taken into consideration, the micellar particles typically have a size of 10 to 200 nm. For example, the size is 10 to 100 nm. It will be noted that the micellar particle used herein means a particle formed as a result of a particulate association between the pH sensitive compound and the amphipathic substance by the hydrophobic interaction. Typically, particles of a monomolecular membrane structure are mentioned, but not including those forming a bimolecular lipid membrane structure (e.g., liposome). The particle size of the pH sensitive carrier indicated in this specification can be measured according to a dynamic light scattering method (Nano ZS 90, made by MALVERN Instruments Ltd).

It should be noted that it is sufficient that a pH sensitive carrier exists in an aqueous solution containing the pH sensitive carrier even if a pH sensitive compound or an amphipathic substance exists in free state without forming an associate.

The respective components of the pH sensitive carrier are now described.

Constituent Components of pH Sensitive Carrier
(pH Sensitive Compound)

As a pH sensitive, mention is made of at least one selected from the group consisting of deoxycholic acid, cholic acid, ursodeoxycholic acid, chenodeoxycholic acid, hyodeoxycholic acid, C27 bile acid, glycodeoxycholic acid, glycyrrhizic acid, glycyrrhetinic acid and salts thereof. The salts of the pH sensitive compound are not critical, for which mention is made of salts of alkali metals such as lithium, sodium, potassium and the like, salts of alkaline earth metals such as magnesium, calcium, barium and the like, and ammonium salts. These pH sensitive compounds may be used singly or in combination of two or more.

Illustrative pH sensitive compounds include deoxycholic acid, ursodeoxycholic acid, chenodeoxycholic acid, hyodeoxycholic acid, glycodesoxycholic acid, glycyrrhizic acid or salts thereof, of which deoxycholic acid, ursodeoxycholic acid, glycyrrhizic acid or salts thereof are specific examples.

Deoxycholic acid, cholic acid, ursodeoxycholic acid, chenodeoxycholic acid, hyodeoxycholic acid, C27 bile acid and glycodesoxycholic acid, which are illustrative examples, are generically called "bile acid". The bile acid has been known as a typical steroid derivative since before the 1920s and has been utilized in the field of bacteriology. The bile acid forms complexes with cholesterol, lipids and fat-soluble vitamins in the human body and has a role of supplementing absorption thereof. Moreover, because of the capability of forming complexes with lipids, proteins and hydrophobic materials in view of physicochemical properties of the bile acid, it has been long utilized for isolation and purification of proteins and also as a solubilizer or emulsifier. In recent years, attention has been paid to the use in a preparation process of vaccine and also to as an absorption enhancer for drug through a bile acid transporter. Sodium deoxycholate (also known as sodium desoxycholate) and ursodeoxycholic acid (also known as ursodesoxycholic acid) have been approved as a pharmaceutical additive capable of being injected to humans, respectively, and their superior safety performance has been recognized. Accordingly, deoxycholic acid, ursodeoxycholic acid or salts thereof (e.g., sodium salts) can be used as the pH sensitive compound.

The pH sensitive compound is typically present in an amount of not less than 10 moles per 100 moles of amphipathic substance. For example, it is present in an amount 10 to 640 moles, for example at 20 to 320 moles, for example at 20 to 160 moles per 100 moles of amphipathic substance.

Amphipathic Substance

The amphipathic substance includes at least one selected from the group consisting of a phosphatidylcholine having 10 to 12 carbon atoms, a polyoxyethylene sorbitan monofatty acid ester having 12 to 18 carbon atoms, a sorbitan fatty acid ester having 16 to 18 carbon atoms, glycerol monooleate, glycerol dilaurate, glycerol distearate, glycerol dioleate, polyoxyethylene castor oil and α-tocopherol. These amphipathic substances may be used singly or in combination of two or more. As used herein, the "number of carbon atoms" of amphipathic substance in the present specification means the number of carbon atoms of a fatty acid moiety (acyl group) serving as the hydrophobic site of the amphipathic substance.

As a phosphatidylcholine having 10 to 12 carbon atoms, a diacylphosphatidylcholine having a saturated acyl group can be used, for which mention is made, for example, of didecanoylphosphatidylcholine (DDPC: 1,2-didecanoyl-sn-glycero-3-phosphatidylcholine) and dilauroylphosphatidylchlorine (DLPC: 1,2-dilauroyl-sn-glycero-3-phosphatidylcholine). The phophatidylcholine may be either a naturally-derived one or a synthesized one obtained by known processes, or commercially available ones may also be used.

For a polyoxyethylene sorbitan monofatty acid ester having 12 to 18 carbon atoms, mention is made of a polyoxyethylene sorbitan monolauric acid ester (polyoxyethylene sorbitan monolaurate), polyoxyethylene sorbitan myristic acid ester (polyoxyethylene sorbitan monomyristate), polyoxyethylene sorbitan monopalmitic acid ester (polyoxyethylene sorbitan palmitate), polyoxyethylene sorbitan monostearic acid ester (polyoxyethylene sorbitan monostearate), polyoxyethylene sorbitan monooleic acid ester (polyoxyethylene sorbitan monooleate) and the like. Although the degree of polymerization of the polyoxyethylene is not critical, the degree of polymerization with respect to the total of polyethylene chains added to the sorbitan can be 10 to 200, for example 15 to 100, for example 20 to 50. The polyoxyethylene sorbitan monofatty acid ester may be either a synthesized one or a commercial product. Commercial products of the polyoxyethylene sorbitan monofatty acid ester can include, for example, those commercially sold under the designations of Tween 20 (polyoxyethylene sorbitan monolauric acid ester), Tween 40 (polyoxyethylene sorbitan monopalmitic acid ester), Tween 60 (polyoxyethylene sorbitan monostearic acid ester) and Tween 80 (polyoxyethylene sorbitan monooleic acid ester). Of these, polyoxyethylene sorbitan monofatty acid esters (Tween 40, Tween 60 and Tween 80) having 16 to 18 carbon atoms are specific examples.

As a sorbitan fatty acid ester having 16 to 18 carbon atoms, mention is made of sorbitan monofatty acid esters such as sorbitan monopalmitic acid ester (sorbitan monopalmitate), sorbitan monostearic acid ester (sorbitan monostearate), sorbitan monooleic acid ester (sorbitan monooleate) and the like, and sorbitan trifatty acid esters such as sorbitan tripalmitic acid ester (sorbitan tripalmitate), sorbitan tristearic acid ester (sorbitan tristearate), sorbitan trioleic acid ester (sorbitan trioleate) and the like. The sorbitan fatty acid ester used may be either a synthesized one or a commercial product. As a commercial product of the sorbitan fatty acid ester, there can be used, for example, those sold under the designations of SPAN 40 (sorbitan palmitic acid ester), SPAN 60 (sorbitan stearic acid ester), SPAN 80 (sorbitan oleic acid ester), SPAN 65 (sorbitan tristearic acid ester), and SPAN 85 (sorbitan trioleic acid ester). Of these, SPAN 80, SPAN 65 and SPA 85 are particular examples.

Glycerol monooleate (glyceryl monooleate), glycerol dilaurate (glyceryl dilaurate), glycerol distearate (glyceryl distearate) and glycerol dioleate (glyceryl dioleate) are acyl glycerols wherein one or two molecules of a fatty acid are ester-bound to glycerol provided that the sites at which the fatty acid is bound are not critical. For instance, with glycerol monooleate that is a monoacyl glycerol, the fatty acid may be bound to at the C1 position or C2 position of glycerin. With glycerol dilaurate, glycerol distearate and glycerol dioleate which are each a diacyl glycerol, the fatty acid may be ester bound to at the C1 and C2 positions or at the C1 and C3 positions of glycerin. As a glyceryl dilaurate, for example, α,α'-dilaurate which is substituted at the C1 and C3 positions can be used. As glycerol distearate or glycerol dioleate, a diacyl glycerol which is substituted at the C1 and C2 positions can be used. These glycerol derivatives may be synthesized ones or commercial products, respectively.

As a polyoxyethylene castor oil, mention is made of adducts of polyoxyethylenes to castor oil. The degree of polymerization of polyoxyethylene is not critical and can be 3 to 200, for example 5 to 100, for example 10 to 50. The polyoxyethylene castor oil may be a synthesized one or a commercial product.

For α-tocopherol, there may be used either naturally derived ones or ones prepared by known processes, and commercial products may also be used.

As these amphipathic substances, phosphatidylcholines having 10 to 12 carbon atoms can be used, of which dilauroylphosphatidylcholine (DLPC) having 12 carbon atoms are particular examples.
Combinations of the pH sensitive compound and the amphipathic substance can also be used.

The pH sensitive carrier is able to develop a membrane disruptive function promoting effect at a desired pH by the proper combination of a pH sensitive compound and an amphipathic substance. On this occasion, the pH at which the pH sensitive carrier commences to develop the membrane disruptive promoting effect differs depending on the combination of a pH sensitive compound and an amphipathic substance. This is considered for the following reasons: pKa differs depending on the type of pH sensitive compound and the manner of forming association with an amphipathic substance also differs depending on the combination of a pH sensitive compound and an amphipathic substance. Accordingly, when a combination of a pH sensitive compound and an amphipathic substance is appropriately changed, the proper choice of the pH at which the function can be developed is possible, thus enabling in vivo delivery and intracellular delivery to be designed in detail.

In the pH sensitive carrier, illustrative combinations of pH sensitive compounds and amphipathic substances include deoxycholic acid and DDPC, deoxycholic acid and DLPC, deoxycholic acid and Tween 20, deoxycholic acid and Tween 40, deoxycholic acid and Tween 60, deoxycholic acid and Tween 80, deoxycholic acid and SPAN 40, deoxycholic acid and SPAN 60, deoxycholic acid and SPAN 80, deoxycholic acid and SPAN 65, deoxycholic acid and SPAN 85, deoxycholic acid and α-tocopherol, deoxycholic acid and glycerol monooleate, deoxycholic acid and glycerol distearate, deoxycholic acid and glycerol dioleate, deoxycholic acid and glycerol dilaurate (α,α'-dilaurin), deoxycholic acid and polyoxyethylene castor oil, ursodeoxycholic acid and DDPC, ursodeoxycholic acid and DLPC, ursodeoxycholic acid and Tween 20, ursodeoxycholic acid and Tween 40, ursodeoxycholic acid and Tween 60, ursodeoxycholic acid and Tween 80, ursodeoxycholic acid and SPAN 40, ursodeoxycholic acid and SPAN 60, ursodeoxycholic acid and SPAN 80, ursodeoxycholic acid and SPAN 65, ursodeoxycholic acid and SPAN 85, ursodeoxycholic acid and α-tocopherol, ursodeoxycholic acid and glycerol monooleate, ursodeoxycholic acid and glycerol distearate, ursodeoxycholic acid and glycerol dioleate, ursodeoxycholic acid and glycerol dilaurate (α,α'-dilaurin), ursodeoxycholic acid and polyoxyethylene castor oil, glycyrrhizic acid and DDPC, glycyrrhizic acid and DLPC, glycyrrhizic acid and Tween 20, glycyrrhizic acid and Tween 40, glycyrrhizic acid and Tween 60, glycyrrhizic acid and Tween 80, glycyrrhizic acid and SPAN 40, glycyrrhizic acid and SPAN 60, glycyrrhizic acid and SPAN 80, glycyrrhizic acid and SPAN 65, glycyrrhizic acid and SPAN 85, glycyrrhizic acid and α-tocopherol, glycyrrhizic acid and glycerol monooleate, glycyrrhizic acid and glycerol distearate, glycyrrhizic acid and glycerol dioleate, glycyrrhizic acid and glycerol dilaurate (α,α'-dilaurin), and glycyrrhizic acid and polyoxyethylene castor oil.

More specifically, mention is made of deoxycholic acid and DDPC, deoxycholic acid and DLPC, deoxycholic acid and Tween 40, deoxycholic acid and Tween 60, deoxycholic acid and Tween 80, deoxycholic acid and SPAN 40, deoxycholic acid and SPAN 65, deoxycholic acid and SPAN 85, deoxycholic acid and α-tocopherol, deoxycholic acid and monoolein, deoxycholic acid and polyoxyethylene castor oil, ursodeoxycholic acid and DDPC, ursodeoxycholic acid and DLPC, ursodeoxycholic acid and Tween 40, ursodeoxycholic acid and Tween 60, ursodeoxycholic acid and Tween 80, ursodeoxycholic acid and SPAN 40, ursodeoxycholic acid and SPAN 65, ursodeoxycholic acid and SPAN 85, ursodeoxycholic acid and α-tocopherol, ursodeoxycholic acid and monoolein, ursodeoxycholic acid and polyoxyethylene castor oil, glycyrrhizic acid and DDPC, glycyrrhizic acid and DLPC, glycyrrhizic acid and Tween 40, glycyrrhizic acid and Tween 60, glycyrrhizic acid and Tween 80, glycyrrhizic acid and SPAN 40, glycyrrhizic acid and SPAN 65, glycyrrhizic acid and SPAN 85, glycyrrhizic acid and α-tocopherol, glycyrrhizic acid and monoolein, and glycyrrhizic acid and polyoxyethylene castor oil.

Aqueous Solvent

The pH sensitive carrier may be contained in an aqueous solution. It will be noted that an aqueous solution containing a pH sensitive carrier may also be hereinafter referred to as "carrier dispersion."

As a solvent of the aqueous solution containing a pH sensitive carrier, there is mentioned an aqueous solution containing a buffer, NaCl or a sugar such as glucose, sucrose or the like.

For the buffer, known buffers can be conveniently used so far as they are able to maintain the pH of an aqueous solution containing a pH sensitive carrier at a level no less than a physiological pH and no specific limitation is placed thereon. The buffers include, for example, a phosphate buffer, a citrate buffer, a citrate-phosphate buffer, a trishydroxymethylaminomethane-HCl buffer (Tris hydrochloride buffer), Good's buffers such as an MES buffer (2-morpholinoethanesulfonate buffer), a TES buffer (N-tris(hydroxymethyl)methyl-2-aminoethanesulfonate buffer), an acetate buffer, an MOPS buffer (3-morpholinopropanesulfonate buffer), an MOPS-NaOH buffer, an HEPES buffer (4-(2-hydroxyethyl)-1-piperazineethanesulfonate buffer), an HEPES-NaOH buffer and the like, amino acid buffers such as a glycine-hydrochloride buffer, a glycine-NaOH buffer, a glycylglcyine-NaOH buffer, a glycylglycine-KOH buffer and the like, boron buffers such as a Tris-borate buffer, a borate-NaOH buffer and a borate buffer, or an imidazole buffer. Of these, a phosphate buffer, a citrate buffer, a citrate-phosphate buffer, a Tris-hydrochloride buffer, an MES buffer, an acetate buffer and an HEPES-NaOH buffer are particular examples. The concentration of a buffer is not critical and can be 0.1 to 200 mM, for example 1 to 100 mM. It will be noted that the concentration of a buffer means a concentration (mM) of a buffer contained in an aqueous solution.

The concentration of NaCl or a sugar such as glucose, sucrose or the like is not critical and is typically 0.1 to 200 mM, for example 1 to 150 mM.

The concentration of the pH sensitive carrier in an aqueous solution is not critical and is such that a total molar concentration of a pH sensitive compound and an amphipathic substance is typically 0.73 μmols/liter to 7.4 mmols/ liter, for example 7.3 µmols/liter to 6.5 mmols/liter, for example 8.0 µmols/liter to 4.2 mmols/liter.

Other Components

The pH sensitive carrier may further contain other components, such as a stabilizer, in the pH sensitive carrier or aqueous solution containing the pH sensitive carrier. The content of these components is not critical unless the pH sensitive carrier is destroyed and is typically not larger than 150 mols, for example not larger than 66.4 mols per 100 mols of the amphipathic substance.

The stabilizer is not critical in type unless the pH sensitive carrier is destroyed and known stabilizers are usable including, for example: saturated or unsaturated alcohols having 4 to 20 carbon atoms such as 1-octanol, 1-dodecanol, 1-hexadodecanol, 1-eicosanol and the like; saturated or unsaturated fatty acids having 12 to 18 carbon atoms such as lauric acid, myristic acid, palmitic acid, stearic acid, oleic acid and the like; alkyl (alkyl having 1 to 3 carbon atoms) esters of saturated or unsaturated fatty acids having 8 to 18 carbon atoms such as methyl caprylate (methyl octanoate), methyl caprylate (ethyl octanoate), methyl laurate, ethyl laurate, ethyl myristate, ethyl palmitate, ethyl stearate, methyl oleate, ethyl oleate and the like; D(L)-amino acids such as D(L)-alanine, alginin, asparagine, aspartic acid, cysteine, glutamine, glycine, histidine, leucine, isoleucine, lysine, methionine, proline, serine, threonine, tryptophan, tyrosine, valin, phenylalanine and the like; amino acid triglycerides such as tricaproin, tricaprylin and the like; polyoxyethylene sorbitan trifatty acid esters having 12 to 18 carbon atoms (e.g., Tween 65, Tween 85) such as polyoxyethylene sorbitan tripalmitic acid ester, polyoxyethylene sorbitan trioleic acid ester and the like; polyoxyethylene alkyl esters having 12 to 18 carbon atoms (e.g., PEG-20 stearyl ether, PEG-23 lauryl ether) such as polyoxyethylene lauric acid ester, polyoxyethylene myristic acid ester, polyoxyethylene palmitic acid ester, polyoxyethylene stearic acid ester and the like; polyoxyalkylene hardened castor oils (e.g., PEG-10 hardened castor oil, PEG-40 hardened castor oil and PEG-60 hardened castor oil); glycerol esters of saturated or unsaturated monofatty acids having 8 to 18 carbon atoms such as caprylin (glycerol octenoate), glycerol monocaprylate, glycerol monolaurate, glycerol monomyristate, glycerol monopalmitate, glycerol monostearate, glycerol monooleate and the like; glycerol esters of difatty acids having 8 to 16 carbon atoms such as glycerol dioctanoate, glycerol dicaprylate, glycerol dilaurate, glycerol dimyristate, glycerol dipalmitate and the like; and α-tocopherol acetic ester, castor oil, soybean oil, cholesterol, squalene, squalane, lactose, ascorbyl palmitate, benzyl benzoate, methyl paraoxybenzoate, ethyl paraoxybenzoate, propyl paraoxybenzoate, butyl paraoxybenzoate and the like. As used herein, the "number of carbon atoms" means the number of carbon atoms of a fatty acid moiety (acyl group) serving as the hydrophobic site.

Method of Preparing a pH Sensitive Carrier

In a further illustrative aspect, there is provided a method for preparing a pH sensitive carrier capable of developing a membrane disruptive function promoting effect, which method including associating at least one pH sensitive compound selected from the group consisting of deoxycholic acid, cholic acid, ursodeoxycholic acid, chenodeoxycholic acid, hyodeoxycholic acid, C27 bile acid, glycodesoxycholic acid, glycyrrhizic acid, glycyrrhetinic acid and salts thereof and at least one amphipathic substance selected from the group consisting of a phosphatidylcholine having 10 to 12 carbon atoms, a polyoxyethylene sorbitan monofatty acid ester having 12 to 18 carbon atoms, a sorbitan fatty acid ester having 16 to 18 carbon atoms, glycerol monooleate, glycerol dilaurate, glycerol distearate, glycerol dioleate, polyoxyethylene castor oil and α-tocopherol.

For the association of the pH sensitive compound and the amphipathic substance, it is sufficient to bring the pH sensitive compound and the amphipathic substance into contact with each other in an aqueous solution. Thus, the pH sensitive carrier can be prepared by bringing the pH sensitive compound and the amphipathic substance into mutual contact in an aqueous solution. For example, an aqueous solution containing a pH sensitive compound and an amphipathic substance is prepared and is subsequently subjected to dispersion under vigorous agitation by use of an emulsifying machine, a vortex mixer, ultrasonic waves or the like, by which there can be obtained a pH sensitive carrier in the form of the pH sensitive compound and the amphipathic substance being associated.

For the preparation of an aqueous solution containing a pH sensitive compound and an amphipathic substance, no specific limitation is placed thereon so far as an associated product of the pH sensitive compound and the amphipathic substance is formed. For instance, mention is made of: (1) a method wherein an aqueous solution containing a pH sensitive compound and an aqueous solution containing an amphipathic substance are separately prepared, and these aqueous solutions are mixed, followed by dispersion under vigorous agitation by use of an emulsifying machine, a vortex mixer, ultrasonic waves or the like to obtain a pH sensitive carrier; and (2) a preparation method using the Bangham method known as a method of preparing a liposome. More specifically, according to the Bangham method, constituent components of the pH sensitive carrier such as a pH sensitive compound and an amphipathic substance are dissolved in an organic solvent (e.g., methanol or chloroform) in a glass container and the organic solvent is removed such as with a rotary evaporator to form a thin film on the walls of the glass container. Next, an aqueous solution is added to the glass container formed with the thin film, followed by swelling the thin film at a normal a temperature (5 to 35° C.) and shaking the glass container at a normal temperature (5 to 35° C.). On this occasion, while vigorously agitating by means of an emulsifying machine, a vortex mixer or ultrasonic waves, the thin film can be well dispersed in the aqueous solution. In the above preparation method (1), a pH sensitive compound may be mixed in an aqueous solution containing an amphipathic substance. It will be noted that a solvent for the aqueous solution may be such a solvent as used for the aqueous solution set out hereinbefore.

It will also be noted that as to the details of the Bangham method, reference can be made to known methods of preparing liposomes as described in "Liposomes" (edited by Shoushichi Nojima, Jyunzou Sunamoto and Keizou Inoue, and published by Nankoudou) and "Liposomes in Life Science" (edited by Hiroshi Terada and Tetsuro Yoshimura, and published by Springer-Verlag, Tokyo).

The manner of adding other components such as a stabilizer, which may be contained in a pH sensitive carrier or in an aqueous solution containing the pH sensitive carrier, is not critically limited. For instance, the components may be added to an aqueous solution containing a pH sensitive compound or an aqueous solution containing an amphipathic substance. Alternatively, when preparing a thin film, the components may be dissolved along with the constituent components of the pH sensitive carrier, after which using the resulting thin film containing these components, there can be obtained an aqueous solution containing a pH sensitive carrier.

The pH sensitive carrier obtained in a manner as stated above is able to develop such a membrane disruptive function promoting effect and can be conveniently used for DDS.

<pH Sensitive Drug and pH Sensitive Drug Composition>

According to an illustrative embodiment, there is provided a pH sensitive drug wherein a pH sensitive carrier supports at least one physiologically active substance therewith.

As used herein, the term "support" means a form of a physiologically active substance included in a carrier, a form of the substance inserted into the carrier, or a form of the substance bound directly or via a medium to the surface of the carrier. As used herein, the term "bound" means either chemically bound with covalent bond or ionic bond or physically bound with van der Waals bond or hydrophobic bond. The physiologically active substance may be either a hydrophilic substance or hydrophobic substance. If the physiologically active substance is made of a hydrophobic substance, the active substance is typically supported in the form of being included in a pH sensitive carrier or being inserted into the pH sensitive carrier. Where the physiologically active substance is hydrophilic in nature, the substance can be supported in the form of being bound directly or via a medium to the carrier surface.

The pH sensitive carrier is able to support a physiologically active substance. When the pH sensitive carrier develops the membrane disruptive function promoting effect in an environment of less than a physiological pH, the supported physiologically active substance can be delivered to a desired site. Although not clearly known, the mechanism for this is assumed in the following way (see FIG. 1B). It will be noted that no limitation should be based on the following assumption.

The pH sensitive drug wherein the pH sensitive carrier supports a physiologically active substance is taken up in cells via endocytosis thereby forming an endosome containing the pH sensitive drug. Thereafter, the interior of the endosome leads to an acidic environment. On this occasion, when the ambient environment of the pH sensitive drug arrives at less than a physiological pH (e.g., a pH of 6.5), the membrane disruptive function promoting effect of the pH sensitive carrier develops. More particularly, the constituent components of the pH sensitive carrier and the membrane components of the endosome are caused to be rearranged, so that the physiologically active substance supported with the pH sensitive carrier existing in the endosome migrates to the cellular cytosol. This enables the physiological substance to be directly delivered to a desired cellular cytosol and thus, it is considered that such a high pharmacological effect is shown.

According to another illustrative embodiment, there is also provided a pH sensitive drug composition including a pH sensitive carrier and at least one physiologically active substance. On this occasion, the physiologically active substance is present on outside (separately) of the pH sensitive carrier unlike the pH sensitive drug according to the above embodiment, and the physiologically active substance and the pH sensitive carrier are not bound directly or via a medium. More particularly, the pH sensitive drug composition according to this embodiment is formed of a pH sensitive carrier and a physiologically active substance being, respectively, mixed independently.

The pH sensitive drug composition wherein a pH sensitive carrier and a physiologically active substance are respectively mixed independently can deliver the physiologically active substance to a desired site after the pH sensitive carrier develops the membrane disruptive function promoting effect in an environment whose pH is less than a physiological pH. Although not clearly known, the development mechanism is assumed to be similar to the case of the pH sensitive drug wherein the pH sensitive carrier supports a physiologically active substance (see FIG. 1C). It is noted that no limitation should be based on the following assumption.

More particularly, the pH sensitive drug composition according to this illustrative embodiment is taken up in the cell by the endocytosis of the pH sensitive carrier by the cell. At this time, along with the pH sensitive carrier, a physiologically active substance is also taken up in the cell by the endocytosis of the pH sensitive carrier by the cell. As a consequence, endosomes independently containing the pH sensitive carrier and the physiologically active substance therein, respectively are formed. Thereafter, the inside of the endosomes is led to an acidic environment and the ambient environment arrives at less than a physiological pH (e.g., a pH of 6.5), whereupon the membrane disruptive function promoting effect of the pH sensitive carrier develops. In doing so, the physiologically active substance existing in the inside of the endosomes migrates to the cellular cytosol. In this way, the physiologically active substance can be delivered directly to a desired cellular cytosol.

The pH sensitive drug and pH sensitive drug composition is able to efficiently deliver a physiologically active substance to a site of living body whose pH becomes lowered due to tumor or inflammation. More particularly, the pH sensitive drug and pH sensitive drug composition can develop a membrane disruptive function promoting effect at a site where the pH becomes lower, so that the physiologically active substance can be selectively delivered to a treatment area such as of inflammation.

The type of physiologically active substance to be supported with the pH sensitive carrier used in the pH sensitive drug and pH sensitive drug composition is not critical in type. For instance, as a physiologically active substance, mention is made of a nucleic acid, a low molecular weight compound, a protein, and a peptide.

The nucleic acid includes one having a treating effect, such as siRNA, ODN (oligodeoxynucleotide), DNA or the like.

As a low molecular weight compound, mention is made of: antineoplastics such as mitomycin, docetaxel, methotrexate and the like; prodrugs such as 5-aminolevulinic acid, protoporphyrin IX and the like; anti-inflammatory agents such as ganciclovir, dexamethasone, ribavirin, vidarabine and the like; contrast agents such as DOTA(1,4,7,10-tetraazacyclotetradecane-N,N',N'',N'''-tetraacetic acid), DTPA (1,4,7,10-tetraazacyclodecane-N,N',N'',N'''-tetraacetic acid) and the like; and neuroprotectants such as edaravone and the like.

As a protein, mention is made of oxidoreductases such as SOD (superoxide dismutase), indophenoloxidase and the like; cytokines such as IL-10 and the like, growth factors such as b-FGF and the like, thrombolytic agents such as t-PA and the like, hormones such as erythropoietin and the like, and anti-cell proteins PSD (Postsynaptic density protein), FNK (Anticell death factor) and the like; and antibodies such as Fab (Fragment), IgG, IgE and the like.

As a peptide, mention is made of: peptide drugs such as cyclosporin A, JIP-1 (JNK-interacting protein 1) and the like.

Variations of the described embodiments are understood by those of ordinary skill in the relevant art.

The amount of the physiologically active substance is not critical and can be appropriately selected depending on the type of physiologically active substance.

For the method of supporting a physiologically active substance in the pH sensitive carrier, there can be used any of known methods depending on the type of physiologically active substance. Such methods are not critical. For a method of obtaining a form of inclusion in the carrier and a form of insertion into the carrier, mention is made of a method wherein after formation of a pH sensitive carrier according to the afore-stated method of preparing a pH sensitive carrier, the pH sensitive carrier is immersed in a solution containing a physiologically active substance to permit the physiologically active substance to be taken in the pH sensitive carrier and a method wherein a solution containing a physiologically active substance is charged into a container formed with a thin film according to the afore-stated method of preparing a pH sensitive carrier thereby causing the physiologically active substance to be included in the carrier. For a method of obtaining a form of binding directly or via a medium to the surface of the carrier, mention is made of a method wherein a pH sensitive compound or an amphipathic substance used as a constituent component of the pH sensitive carrier is introduced with a functional group capable of reaction with a desired type of physiologically active substance and is subsequently reacted with the physiologically active substance to obtain a pH sensitive carrier bound with the physiologically active substance. It will be noted that the binding with the physiologically active substance may be made either prior to the preparation of the pH sensitive carrier or after the preparation.

The pH sensitive carrier and the physiologically active substance can be mixed according to any of known methods determined depending on the type of physiologically active substance. Such methods are not critical, for which mention is made, for example, of a method wherein the carrier and a physiologically active substance are mixed with a medium such as an aqueous solvent, a diluent and the like.

The pH sensitive drug and the pH sensitive drug composition may further include other types of drug additives. Although the pH sensitive drug and pH sensitive drug composition may be in the form of solid preparations including tablets, powders, capsules and the like, liquid preparation such as injection preparations are preferred. The liquid preparation may be provided in the form of a dried product which can be regenerated with use of water or other appropriate diluent on use.

The tablet and capsule can be subjected to an enteric coating according to an ordinary procedure. The enteric coating may be one ordinarily employed in this field. The capsule may contain either a solid or a liquid therein.

Where the pH sensitive drug and the pH sensitive drug composition are in the form of a liquid preparation, the drug additives may include a solvent (e.g., a physiological saline solution, sterilized water, a buffer solution or the like), a membrane stabilizing agent (e.g. cholesterol or the like), a tonicity agent (e.g., sodium chloride, glucose, glycerin or the like), an antioxidant (e.g., tocopherol, ascorbic acid, glutathione or the like), a preservative (e.g., chlorobutanol, paraben or the like) and the like. The solvent may be one used for the preparation of the pH sensitive drug and pH sensitive drug composition.

Where the pH sensitive drug and the pH sensitive drug composition are in the form of a solid preparation, the drug additives may include an excipient (e.g., a sugar such as lactose, sucrose or the like, a starch such as corn starch, a cellulose such as crystalline cellulose, gum arabic, magnesium metasilicate aluminate, calcium phosphate or the like), a lubricant (e.g., magnesium stearate, talc, polyethylene glycol or the like), a binder (e.g., mannitol, a sugar such as sucrose, crystalline cellulose, polyvinylpyrrolidone, hydroxypropyl methylcellulose or the like), a disintegrant (e.g., a starch such as potato starch, a cellulose such as carboxymethylcellulose, crosslinked polyvinylpyrrolidone or the like), a colorant, a flavoring agent and the like.

The pH sensitive drug and pH sensitive drug composition can be prepared by mixing with the above-mentioned drug additives as they are or after freeze-drying. Where the pH sensitive drug and pH sensitive drug composition are freeze-dried, it is possible to add an appropriate type of diluent prior to the freeze-drying.

The administration form in case where the pH sensitive drug and the pH sensitive drug composition are used for treatment of a subject is not critical, for which mention is made, for example, of oral administration, and parenteral administration such as intravenous injection, intraarterial injection, subcutaneous injection, intracutaneous injection, intramuscular injection, intraspinal injection, percutaneous administration or percutaneous absorption. For example, where a peptide or protein is used as a physiologically active substance, administration via parenteral routes such as of subcutaneous injection, intracutaneous injection, intramuscular injection and intravenous injection is possible. It will be noted that with respect to the pH sensitive drug composition wherein a pH sensitive carrier and a physiologically active substance are respectively independently mixed, it is possible to administer it in the form of local administration, particularly, subcutaneous injection, intracutaneous administration or intramuscular administration.

When the external environment of the pH sensitive drug and the sensitive drug composition becomes lower than a physiological pH (e.g., pH 6.5) after administration to a subject, the membrane disruptive function promoting effect, or the membrane disruptive function promoting effect and the membrane fusion function promoting effect are developed, thus enabling a physiologically active substance to be specifically released in an efficient manner.

Thus, according to an illustrative embodiment, there is provided a method for treating or preventing a disease including orally or perorally administering an effective amount of the above pH sensitive drug or pH sensitive drug composition to a subject requiring the treatment or prevention.

The subject can be a mammal, for example a human being.

As a disease, mention is made of, for example, cancers such as prostate cancer, lung cancer, colon cancer, liver cancer, stomach cancer, brain cancer, breast cancer and the like, infection diseases such as HIV (Human Immunodeficiency Virus), hepatitis C, hepatitis B and the like, and central neurological diseases such as Alzheimer's disease, Parkinson's disease and the like.

More particularly, according to an illustrative embodiment, there is provided a method for treating or preventing a disease.

Variations of the described embodiments are understood by those of ordinary skill in the relevant art.

In an illustrative embodiment, the pH sensitive drug and the pH sensitive drug composition can allow a physiologically active substance to be directly transported to cells by culture. That is, according to this embodiment, there is provided a culture method for transporting a physiologically active substance to cells.

The culture method includes the step of culturing cells in a medium containing a pH sensitive drug and/or a pH sensitive drug composition.

The pH sensitive drug and the pH sensitive drug composition are, respectively, those set out above. More particularly, there can be mentioned a pH sensitive drug wherein a pH sensitive carrier supports at least one physiologically active substance and a pH sensitive drug composition which independently contains a pH sensitive carrier and at least one physiologically active substance therein. These may be used singly or in combination.

The medium is not critical and those known in the art may be used. In particular, mention is made of MEM, DMEM, RPMI and the like.

The amount of a pH sensitive drug and/or a pH sensitive drug composition in the medium is not critical and the total molar concentration of a pH sensitive composition and an amphipathic substance is typically 0.73 μmols/liter to 7.4 mmols/liter, for example 7.3 μmols/liter to 6.5 mmols/liter, for example 8.0 μmols/liter to 4.2 mmols/liter.

The pH of the medium is typically not less than 7.0, for example 7.2 to 7.8. If the pH of the medium is not less than 7.0, a pH sensitive compound used as a constituent of the pH sensitive carrier can be favorably prevented from becoming unstable in the medium.

The types of cells are not critical and mention is made of cells collected from a subject, established cultured cells and the like.

On this occasion, specific examples of the cells collected from a subject or established cultured cells include dendritic cells, NK (natural killer) cells, T-lymphocyte cells, B-lymphocyte cells and lymphocyte cells.

Of the above cells, it is possible to use cells collected from a subject. For example, dendritic cells, NK cells, T cells and lymphocyte cells collected from a subject can be used.

Where cells collected from a subject are used, there can be obtained cells of the subject through blood drawing, biopsy or the like. Accordingly, the culture method according to this embodiment may further include the step of collecting cells from a subject.

It will be noted that the cultured cells may be administered to a subject. In doing so, the disease of the subject can be treated or prevented. Hence, according to this embodiment, there is provided a method for treating or preventing a disease.

In a further illustrative embodiment, the treating or preventing method includes the steps of collecting cells from a subject, culturing the collected cells in a medium containing a pH sensitive drug and/or a pH sensitive drug composition, and administering the cultured cells to the subject.

In this way, a disease can be treated or prevented. The disease is one as mentioned hereinabove.

Examples

Illustrative examples are hereafter provided which should not be construed as limiting.
Starting Materials In the examples, the following compounds were used. Where the name of reagent and the name of product are the same, the name of product is omitted.

EYPC (non-hydrogenated egg yolk phosphatidylcholine: COATSOME NC-50, made by NOF Corporation)

HSPC (soybean phosphatidylcholine: COATSOME NC-21, made by NOF Corporation)

DDPC (1,2-decanoyl-sn-glycero-3-phosphatidylcholine: COATSOME MC-1010, made by NOF Corporation)

DLPC (1,2-dilauroyl-sn-glycero-3-phosphatidylcholine: COATSOME MC-1212, made by NOF Corporation)

DMPC (1,2-dimystiroyl-sn-glycero-3-phosphatidylcholine: COATSOME MC-4040, made by NOF Corporation)

DPPC (1,2-dipalmitoyl-sn-glycero-3-phosphatidylcholine: COATSOME MC-6060, made by NOF Corporation)

DSPC (1,2-distearoyl-sn-glycero-3-phosphatidylcholine: COATSOME MC-8080, made by NOF Corporation)

DOPC (1,2-dioleoyl-sn-glycero-3-phosphatidylcholine: COATSOME MC 8181, made by NOF Corporation)

POPC (1-palmitoyl-2-oleoyl-sn-3-phosphatidylcholine: COATSOME MC 6081, made by NOF Corporation)

DLPE (1,2-dilauroyl-sn-glycero-3-phosphoethanolamine: COATSOME ME 2020, made by NOF Corporation)

DMPE (1,2-dimyristoyl-sn-glycero-3-phosphoethanolamine: COATSOME ME 4040, made by NOF Corporation)

DSPE (1,2-distearoyl-sn-glycero-3-phosphoethanolamine: COATSOME ME 8080, made by NOF Corporation)

DOPE (1,2-dioleoyl-sn-glycero-3-phosphoethanolamine: COATSOME ME 8181, made by NOF Corporation)

Chems (Cholesteryl hemisuccinate: made by Nacalai Tesque Co., Ltd.)

NBD-PE (1,2-dioleoyl-sn-glycero-3-phosphoethanolamine-N-(7-nitro-2-1,3-benzoxadiazol-4-yl)ammonium: made by Avanti Polar Lipids, Inc.

Rh-PE (1,2-dioleoyl-sn-glycero-3-phoshoethanolamine-N-(lissamine rhodamine B sulfonyl)ammonium: Avanti Polar Lipids, Inc.)

Sodium deoxycholate (Nacalai Tesque Co., Ltd.)

Sodium cholate (Nacalai Tesque Co., Ltd.)

Sodium ursodeoxycholate (Tokyo Chemical Industry Co., Ltd.)

Chenodeoxycholic acid (Tokyo Chemical Industry Co., Ltd.)

Hyodeoxycholic acid (Tokyo Chemical Industry Co., Ltd.)

Methyl cholate (Tokyo Chemical Industry Co., Ltd.)

Sodium dehydrocholate (Tokyo Chemical Industry Co., Ltd.)

Lithocholic acid (Nacalai Tesque Co., Ltd.)

Sodium glycocholate (Tokyo Chemical Industry Co., Ltd.)

Sodium taurocholate (Nacalai Tesque Co., Ltd.)

Sodium glycodeoxycholate (Nacalai Tesque Co., Ltd.)

Sodium taurodeoxycholate (Nacalai Tesque Co., Ltd.)

Sodium glycoursodeoxycholate (Nacalai Tesque Co., Ltd.)

Sodium tauroursodeoxycholate (Nacalai Tesque Co., Ltd.)

C27 bile acid ($3\alpha$, $7\alpha$, $12\alpha$-Trihydroxycholestanoic acid: Avanti Polar Lipids, Inc.)

$5\beta$-Cholanic acid (Sigma-Aldrich Co., LLC)

Monoammonium glycyrrhizinate (Tokyo Chemical Industry Co., Ltd.)

Glycyrrhizic acid (Nagara Science Co., Ltd.)

Sodium saccharin (Wako Pure Chemical Industries, Ltd.)

Methanol (Nacalai Tesque Co., Ltd.)

Chloroform (Wako Pure Chemical Industries, Ltd.)

Acetic acid (Wako Pure Chemical Industries, Ltd.)

Sodium acetate (Kanto Chemical Co., Inc.)
MES-Na (Merck & Co., Inc.)
HEPES-Na (Nacalai Tesque Co., Ltd.)
Sodium chloride (Kanto Chemical Co., Inc.)
Pyranine (Tokyo Chemical Industry Co., Ltd.)
DPX (p-xylene-bis-pyridinium bromide: Molecular Probes Inc.)
PBS (Phosphate Buffered Salts: PBS Tablets, made by Takara Bio Inc.)
Polyoxyethylene sorbitan monofatty acid esters (Tween 20, 40, 60, 80, 65, 85: made by Tokyo Chemical Industry Co., Ltd.)
PEG-20-stearyl ether (polyoxyethylene 20-stearyl ester: made by Wako Pure Chemical Industries, Ltd.)
PEG-23-lauryl ether (polyoxyethylene 23-lauryl ester: made by Wako Pure Chemical Industries, Ltd.)
Sorbitan fatty acid esters (SPAN 20: sorbitan monolaurate, made by Nacalai Tesque Co., Ltd., SPAN 40, 60: made by Tokyo Chemical Industry Co., Ltd., SPAN 80: sorbitan monooleate, made by Nacalai Tesque Co., Ltd., 65: sorbitan tristearate, made by Wako Pure Chemical Industries, Ltd., SPAN 85: made by Tokyo Chemical Industry Co., Ltd.)
Glycerol monocaprate (Monocaprin, made by Tokyo Chemical Industry Co., Ltd.)
Glycerol monocaprylate (Monocaprylin, made by Tokyo Chemical Industry Co., Ltd.)
Glycerol monolaurate (Monolaurin, made by Tokyo Chemical Industry Co., Ltd.)
Glycerol monomyristate (Monomyristin, made by Tokyo Chemical Industry Co., Ltd.)
Glycerol monopalmitate (Monopalmitin, made by Tokyo Chemical Industry Co., Ltd.)
Glycerol monostearate (Monostearin, made by Tokyo Chemical Industry Co., Ltd.)
Glycerol monooleate (Monoolein, made by Tokyo Chemical Industry Co., Ltd.)
Glycerol dilaurate ($\alpha,\alpha$ Dilaurin, made by Tokyo Chemical Industry Co., Ltd.)
Glycerol distearate (made by Wako Pure Chemical Industries, Ltd.)
Glycerol dioleate (made by Wako Pure Chemical Industries, Ltd.)
Polyoxyethylene castor oil (Polyoxyethylene 10 castor oil, made by Wako Pure Chemical Industries, Ltd.)
Polyoxyethylene hardened castor oil (10: polyoxyethylene 10 hardened castor oil, made by Wako Pure Chemical Industries, Ltd., 40: Uniox HC-40, made by NOF Corporation, 60: Uniox HC-60, made by NOF Corporation)
1-Butanol (made by Nacalai Tesque Co., Ltd.)
1-Octanol (made by Nacalai Tesque Co., Ltd.)
1-Dodecanol (made by Tokyo Chemical Industry Co., Ltd.)
1-Hexadecanol (made by Nacalai Tesque Co., Ltd.)
1-Eicosanol (made by Tokyo Chemical Industry Co., Ltd.)
Lauric acid (made by Nacalai Tesque Co., Ltd.)
Sodium oleate (made by Nacalai Tesque Co., Ltd.)
Ethyl octenoate (made by Nacalai Tesque Co., Ltd.)
Ethyl laurate (made by Tokyo Chemical Industry Co., Ltd.)
Ethyl oleate (made by Nacalai Tesque Co., Ltd.)
Lactose (made by Nacalai Tesque Co., Ltd.)
L-leucine (made by Nacalai Tesque Co., Ltd.)
L-histidine (made by Nacalai Tesque Co., Ltd.)
Soybean oil (soybean oil, made by Nacalai Tesque Co., Ltd.)
Squalene (made by Nacalai Tesque Co., Ltd.)
Squalene (made by Nacalai Tesque Co., Ltd.)
$\alpha$-Tocopherol (DL-$\alpha$-tocopherol, made by Nacalai Tesque Co., Ltd.)
Tocopherol acetate (DL-$\alpha$-tocopherol acetate, made by Nacalai Tesque Co., Ltd.)
Benzyl benzoate (made by Nacalai Tesque Co., Ltd.)
Benzyl paraoxybenzoate (made by Tokyo Chemical Industry Co., Ltd.)
Ascorbyl palmitate (made by LKT Laboratories, Inc.)
Gum arabic (gum arabic powder, made by Nacalai Tesque Co., Ltd.)
Gelatin (gelatin purified powder, made by Nacalai Tesque Co., Ltd.)
Cyclodextrin (made by Nacalai Tesque Co., Ltd.)
Methylcellulose (made by Nacalai Tesque Co., Ltd.)
Mineral oil (made by Nacalai Tesque Co., Ltd.)
Paraffin (made by Nacalai Tesque Co., Ltd.)
Sodium hydroxide aqueous solution (0.1 mol/liter: made by Nacalai Tesque Co., Ltd.)
Hydrochloric acid (0.1 mol/liter 1 mol/liter: made by Nacalai Tesque Co., Ltd.)
Triton-X100 (Triton X100, made by Wako Pure Chemical Industries, Ltd.)
Model peptide: OVA257-264 (SIINFEKL, prepared by commission to PH Japan Co., Ltd.)
Fluorescence-labeled peptide: OVA257-264-Rh (prepared by commission to PH Japan Co., Ltd.)
Model protein: OVA (Sigma-Aldrich Inc.)
Trypsin (made by Life Technologies Inc.)
EDTA (ethylenediamine tetraacetate, made by Nacalai Tesque Co., Ltd.)
$\beta$-gal ($\beta$-D-galactosidase, made by Wako Pure Chemical Industries, Ltd.)
FBS (Fetal bovine serum: made by Kokusan Chemical Co., Ltd.)
MEM (Minimum Essential Medium: Eagle's MEM and L-glutamine-containing solution, made by Nacalai Tesque Co., Ltd.)
DMEM without Phenol Red (solution of 4.5 g/l of Dulbecco's Modified Eagle Medium (DMEM) without containing glucose, L-glutamine, pyruvic acid and phenol red)
DMEN (Dulbecco's Modified Eagle Medium, made by Nacalai Tesque Co., Ltd.)
Chloroquine diphosphate (made by Nacalai Tesque Co., Ltd.)
IsoFlow (made by Beckman Coulter Inc.)
Preparation of Samples
Preparation of pH Sensitive Carriers
1000 nmol of an amphipathic substance dissolved in methanol (or chloroform) and a pH sensitive compound or candidate compound dissolved in methanol (or chloroform) were mixed in a 10 mL eggplant flask and converted to a thin film by means of a rotary evaporator (BuCHI). It will be noted that the ratio between the amphipathic substance and the pH sensitive compound or candidate compound was so set as to provide desired ratios (molar ratios of 100:10, 100:20, 100:640, etc.). Where a plurality of amphipathic substances were used, the amphipathic substances were so controlled in total amount to have the number of moles desired (1000 nmol). 1 mL of an MES buffer (MES: 25 mM, NaCl: 125 mM, pH 7.4) was added to the resulting thin film, followed by dispersion by one-minute irradiation with ultrasonic waves at a normal temperature by use of an ultrasonic irradiator (USC-J) to obtain an aqueous solution of an intended pH sensitive carrier (a dispersion of the carrier).

Preparation of Carriers for Comparison
(EYPC Alone and DLPC Alone)

1000 nmol of EYPC or DLPC dissolved in chloroform was placed in a 10 mL eggplant flask, followed by conversion to a thin film by means of a rotary evaporator (BuCHI). 1 mL of an MES buffer (MWS: 25 mM, NaCl: 125 mM, pH 7.4) was added to the resulting thin film, followed by dispersion by one-minute irradiation with ultrasonic waves at a normal temperature by use of a ultrasonic irradiator (USC-J) to obtain a dispersion of EYPC alone or DLPC alone.

Carriers Containing Macromolecular Materials

In a similar way as in the preparation procedure of the pH sensitive carrier, a thin film of a pH sensitive compound and a macromolecular material was prepared to provide a carrier. The macromolecular material, such as gum arabic, gelatin, methylcellulose, mineral oil or paraffin, was used in amounts of ⅕ times, one time and five times the weight of the 1600 nmol of the pH sensitive compound.

(pH Sensitive Liposomes)

In a similar way as in the preparation procedure of the pH sensitive carrier, a thin film of DOPE and Chems or oleic acid was prepared to provide a liposome. It will be noted that the DOPE-Chems (DOPE:Chems=3:2 (by molar ratio)) and the DOPE-oleic acid ((DOPE:oleic acid=7:3 (by molar ratio)), which were, respectively, a pH sensitive liposome, were prepared using 1000 nmol of DOPE, a given amount of Chems or oleic acid and 1 mL of an MES buffer (MES: 25 mM, NaCl: 125 mM, pH 7.4).

Preparation of a peptide-containing carrier and a protein-containing carrier 0 to 1536 μg of OVA257-264 (SIINFEKL) model peptide or an OVA model protein per 1000 nmol of an amphipathic substance was weighed and dissolved in 1 mL of an MES buffer (MES: 25 mM, NaCl: 125 mM, pH 7.4). These solutions were used to prepare the respective carriers, from which there was obtained a dispersion containing the peptide or protein.

With the case using an OVA257-264-Rh fluorescence-labeled peptide, preparation was made using 140 μg of the fluorescence-labeled peptide per 1000 nmol of the amphipathic substance, and with the case using β-gal, 1.4 mg of β-gal per 1000 nmol of the amphipathic substance was used for the preparation.

Measuring Method

Measurement of Transmittance

250 μL of a carrier dispersion was added to 250 μL of an MES buffer (MES: 25 mM, NaCl: 125 mM, pH 7.4) to provide a solution for measurement. Using UV-2450, a transmittance at 500 nm was measured at a normal temperature.

Measurement of Zeta Potential and Particle Size

For the measurement of the zeta potential, 20 to 50 μL of a carrier dispersion was added to 1.0 mL of a HEPES buffer (HEPES: 1.0 mM) whose pH was adjusted to 7.4 to provide a solution for the measurement. The measurement was carried out plural times using Nano ZS 90 and the resulting values of zeta potential were averaged to obtain a zeta potential of the carrier particles.

Measurement of Particle Size and Polydispersity Index

For the measurement of the particle size and polydispersity index (PDI: Polydispersity Index), an appropriate amount of a carrier dispersion was added to an MES buffer (MES: 25 mM, NaCl: 125 mM, pH 7.4) to provide a solution for measurement. The measurement was carried out plural times by use of Nano ZS 90 and the values of Z-average (radius) obtained by dynamic light scattering measurement were averaged and its double value was provided as a Diameter (diameter or particle size). The value of PDI was determined by averaging the values of PDI obtained by plural measurements.

Leaching Test: Measurement of a Leakage (Leaching Rate)

The leakage (leaching rate) was determined according to the method described by K. Kono et al., Bioconjugate Chem., 2008 19 1040-1048 and evaluated using an EYPC liposome including Pyranine serving as a fluorescent substance and DPX serving as a quencher.

3000 nmol of EYPC dissolved in chloroform was measured and placed in a 10 mL eggplant flask and converted to a thin film by use of a rotary evaporator (BuCHI). 500 μL of a Pyranine solution (Pyranine: 35 mM, DPX: 50 mM, MES: 25 mM, pH 7.4) was added, followed by dispersion with use of an ultrasonic irradiator (USC-J) and passage through a polycarbonate film having a pore size of 100 nm by use of an extruder to obtain a uniform particle size. Using an MES buffer (MES: 25 mM, NaCl: 125 mM, pH 7.4) and a G100 column, an outer water layer was substituted to obtain a dispersion of EYPC liposomes including the fluorescent substance. The concentration of the choline group of the phospholipid was determined by use of the phospholipid C test Wako and was adjusted by use of an MES buffer (MES: 25 mM, NaCl: 125 mM, pH 7.4) in such a way as to obtain 1.0 mmol/L of the phospholipid. 20 μL of the EYPC liposome dispersion whose concentration had been adjusted, and 20 μL of an evaluation sample dispersion such as of a carrier or a pH sensitive compound alone, an amphipathic substance alone or the like were charged into 2960 μL of the respective MES buffers (MES: 25 mM, NaCl: 125 mM) which were prepared to have different pHs. After incubation at 37° C. for 30 minutes or 90 minutes (in examples, the results of 90 minutes were shown unless otherwise indicated), fluorescences at Ex 416 and Em 512 nm were observed by use of spectrophotometer FP-6500 to monitor the leakage. The DOPE-Chems and DOPE-oleic acid were, respectively, measured in an acetic acid buffer (acetic acid: 25 mM, NaCl: 125 mM).

With respect to other samples, measurement at a pH of 4.0 to 3.0 was carried out by use of an acetic acid buffer.

It will be noted that the leakage was calculated in such a way that in case where the EYPC liposome dispersion alone was used, it was taken as 0% and a value obtained in case where 30 μL of a 10-fold diluted Triton-X100 was added was taken as 100%.

More particularly, the leakage was calculated according to the following equation. In the following equation, a measured fluorescence intensity is represented by L, a fluorescence intensity of a dispersion alone of EYPC liposomes including a fluorescent substance is represented by $L_0$, and a fluorescence intensity in case where Triton-X100 was added is represented by $L_{100}$.

$$\text{Leakage (\%)} = (L-L_0)/(L_{100}-L_0) \times 100$$

Fusion Test: Measurement of Fusion (Membrane Fusion)

The fusion (membrane fusion) was carried out according to the method described by K. Kono et al., Biomaterials 2008 29 4029-4036 and evaluated by use of FRET (Fluorescence Resonance Energy Transfer). For the fluorescent labeling, NBD-PE and Rh-PE were used.

A thin film of EYPC (1000 nmol of EYPC) containing 0.6 mol % of NBD-PE and Rh-PR relative to EYPC was prepared and added to 1 mL of an MES buffer (MES: 25 mM, NaCl: 125 mM, pH 7.4), followed by dispersion with use of a ultrasonic irradiator (USC-J) and passage through a polycarbonate film having a pore size of 100 nm by use of an extruder to obtain a double fluorescence-labeled EYPC liposome dispersion. 20 µL of the double fluorescence-labeled EYPC liposome dispersion and 20 µL of an evaluation sample dispersion such as of a carrier or a pH sensitive compound alone, an amphipathic compound alone or the like were charged into 2960 µL of MES buffers (MES: 25 mM, NaCl: 125 mM) which were adjusted to different pHs and incubated at 37° C. for 60 minutes, followed by measurement of fluorescent spectra at 500 nm to 620 nm by means of excitation light of 450 nm by use of a spectrophotometer (EP-6500) to obtain a fluorescent intensity ratio between 520 nm and 580 nm.

The fusion rate was calculated such that the fluorescent intensity ratio in case where the double fluorescence-labeled EYPC liposome dispersion obtained above and an amphipathic substance were incubated was taken as 0% and the ratio in case where the double fluorescence-labeled EYPC liposome dispersion and a dispersion of a pH sensitive carrier or an amphipathic substance were subjected to methanol treatment was taken as 100%. The methanol treatment was carried out in such a way that both of the double fluorescence-labeled EYPC liposome dispersion and an evaluation sample dispersion such as of a pH sensitive carrier or an amphipathic compound alone, an amphipathic compound alone or the like were dissolved in methanol and converted to a thin film by use of a rotary evaporator (BuCHI), followed by dispersion by use of 3.0 mL of an MES buffer (MES: 25 mM, NaCl: 125 mM) and an ultrasonic irradiator (USC-J).

More particularly, the fusion rate was calculated according to the following equation. It will be noted that in the following equation, a fluorescence intensity ratio obtained by the measurement is represented by $R$, a fluorescence intensity ratio obtained where the double fluorescence-labeled EYPC liposome dispersion and an amphipathic substance were incubated is represented by $R_0$ and a fluorescence intensity ratio obtained where double fluorescence-labeled EYPC liposome dispersion and an evaluation sample dispersion such as of a carrier, or a pH sensitive compound alone, an amphipathic compound alone or the like were subjected to methanol treatment is represented by $R_{100}$.

Fusion rate (%)=$(R-R_0)/(R_{100}-R_0)\times 100$

Confirmation of Membrane Fusion Against Cell Membrane

It was confirmed by use of HeLa cells that a pH sensitive carrier induced membrane fusion with an actual cell membrane.

On the day before administration of a pH sensitive carrier, HeLa cells were spread on a matsunami glass bottom dish and cultured with 10% FBS-containing DMEM. On this occasion, the culture was carried out by use of an incubator (MCO20AIC) set at 5% $CO_2$ and 37° C. After the incubation, the cells were washed with 10% FBS-containing DMEM. Next, 2.0 mL of DMEM whose pH was adjusted to 7.4 by use of a sodium hydroxide aqueous solution or hydrochloric acid and which contained 25 mM of Hepes and 50 µM of chloroquine diphosphate was added to the cells, followed by one hour pre-incubation.

It will be noted that in case where a test was carried out at a pH of 5.3, 2.0 mL of DMEM whose pH was adjusted to 5.3 by use of a sodium hydroxide aqueous solution or hydrochloric acid and which contained 25 mM of MES and 50 µM of chloroquine diphosphate was added to the cells, followed by one hour pre-incubation. After the pre-incubation, 100 µL of a dispersion of 0.6 mol %, relative to an amphipathic substance, of an Rh-PE fluorescence-labeled pH sensitive carrier was added to a medium adjusted to a given pH, followed by two hours of incubation. The cells were rinsed at least three times with phenol red-free DMEM and observed through a fluorescence microscope (Axiovert 200M—soft: Axio vision 3.0—light source: Fluo Arc). It is to be noted that the fluorescence intensity of the cells was evaluated by use of a flow cytometer (Cytomics FC500, soft: CXP version 2) after the rinsed cells had been harvested with PBS containing 0.025 wt % of trypsin and 0.01 wt % of EDTA.

Evaluation of Cytosolic Delivery Using a Fluorescence-Labeled Peptide

OVA-257-264-Rh was chosen as a model peptide. 140 µg/ml of a fluorescence-labeled peptide solution was prepared by use of PBS passed through a 0.22 µm filter and used for the preparation of a carrier. Cells used were RAW cells, and culture was carried out by use of an incubator (MCO20AIC) set at 5% $CO_2$ and 37° C. The RAW cells were spread on a matsunami glass bottom dish on the day before the charge of the carrier and cultured in a 10% FBS-containing MEM medium.

After rinsing the cells with PBS, the medium was substituted with 1900 µL of a fresh 10% FBS-containing MEM medium, into which 100 µL of the respective samples was charged. Incubation was continued over 16 to 20 hours and the cells were rinsed at least three times with PBS. Thereafter, 2 mL of a fresh 10% FBS-containing MEM medium was added, following by three hours post-incubation. The cells were rinsed with PBS, followed by substitution with a DMEM-without-Phenol-Red medium and observation of the cells through a fluorescence microscope Axiovert 200M—soft: Axio vision 3.0—light source: Fluo Arc (Cytosolic Delivery of β-Gal)

Using PBS passed through a 0.22 µm filter, there was prepared a 1.4 mg/mL of β-gal solution. A mixed thin film made up of 1000 nmol of DLPC and 1600 nmol of deoxycholic acid or ursodeoxycholic acid was dispersed in the thus prepared β-gal solution to prepare a β-gal-containing carrier. On the day before charge, the RAW cells were spread on a matsunami glass bottom dish and cultured, and the cells were rinsed with PBS immediately before charge. The culture was carried out by use of an incubator (MCO 20 AIC) set at 5% $CO_2$ and 37° C. and a 10% FBS-containing MEM medium. After substitution with 1900 µL of a fresh 10% FBS-containing MEM medium, 100 µL of the respective samples was charged, followed by 16 to 20 hours incubation. The cells were rinsed at least three times with PBS. Thereafter, 2 mL of a fresh 10% FBS-containing MEM medium was added, following by three hours post-incubation. The cells were rinsed with PBS, followed by staining the cells with use of a β-Galactosidase Staining Kit (purchased from Takara Bio Inc.), and observing the cells through a microscope (Axiovert 200M—soft: Axio vision 3.0). The staining was carried out in accordance with the recommendation of the kit.

Evaluation of Cytosolic Delivery in the Case where a pH Sensitive Carrier and a Physiologically Active Substance were, Respectively Used Independently On the previous day, RAW cells were spread on a matsunami glass bottom dish and cultured with 10% FBS-containing MEM. After rinsing with PBS, MEM was added, followed by a one hour incubation. 1900 µL of MEM containing fluorescence-labeled peptide-FITC or fluorescence-labeled OVA-FITC at a concentration of 30 µg/mL was prepared and substituted with the culture medium. Moreover, a solution of 100 µL of a pH sensitive carrier was added, followed by 16 to 20 hours of incubation in the culture medium in such a state that both were mixed. It was already confirmed that the fluorescence-labeled peptide- FITC and fluorescence-labeled OVA-FITC were each not supported with the pH sensitive carrier in a mixed state with a pH sensitive carrier-containing solution. After rinsing with PBS and three hours post-incubation with 2 mL of fresh MEM, the cells were rinsed with PBS, followed by substitution with phenol red-free DMEM and observation through a fluorescence microscope. The culture was carried out by use of an incubator (MCO20AIC) set at 5% $CO_2$ and 37° C. and the cells were observed through a fluorescence microscope (Axiovert 200M—soft: Axio vision 3.0—light source: Fluo Arc).

(1) Complexing of Deoxycholic Acid

Initially, complexing of deoxycholic acid and amphipathic substances was evaluated.

Figure 2A:
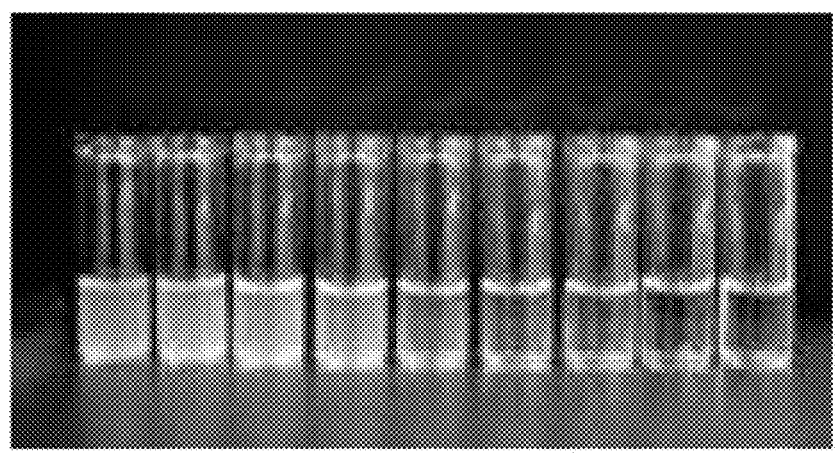
FIG. 2A is a photograph of dispersions of deoxycholic acid and EYPC (Egg Yolk Phosphatidylcholine) wherein deoxycholic acid is contained at different concentrations.
Figure 2B:
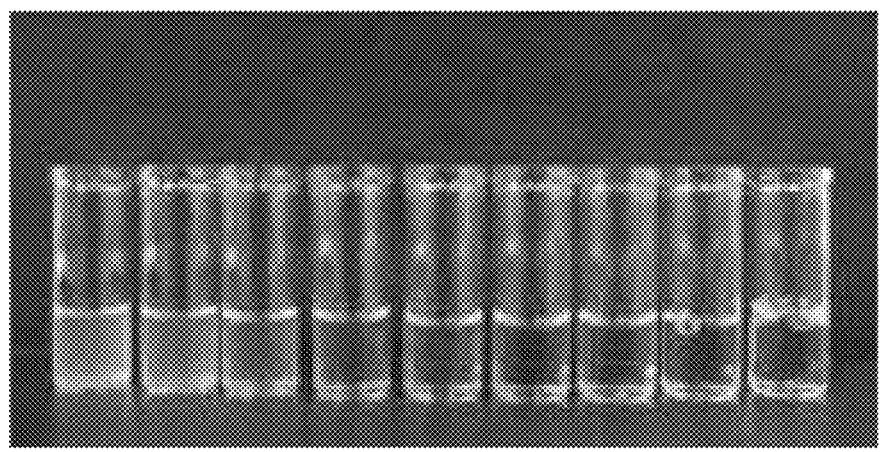
FIG. 2B is a photograph of dispersions of deoxycholic acid and DLPC (Dilauroyl Phosphatidylcholine) wherein deoxycholic acid is contained at different concentrations.

According to the preparation of the foregoing pH sensitive carrier, mixed thin films of 1000 nmol of EYPC or DLPC and different amounts (0 to 6400 nmol) of deoxycholic acid were prepared, to which 1 mL of an MES buffer with a pH of 7.4 was added and irradiated with ultrasonic waves, thereby preparing deoxycholate complexed dispersions. A photograph of the dispersions containing EYPC and deoxycholic acid wherein deoxycholic acid was contained in different amounts is shown in FIG. 2A and a photograph of the dispersions containing DLPC and deoxycholic acid wherein deoxycholic acid was contained in different amounts is shown in FIG. 2B. It will be noted that FIGS. 2A and 2B, respectively, show dispersions of 1000 nmol of the lipids containing, as viewed from the left side thereof, 0 nmol, 50 nmol, 100 nmol, 200 nmol, 400 nmol, 800 nmol, 1600 nmol, 3200 nmol and 6400 nmol of deoxycholic acid. In either lipid of EYPC or DLPC, a dispersion of the lipid alone became clouded, whereas the solutions of complexed deoxylate were found to become clearer depending on the amount of the acid being complexed.

The transmittance of the respective dispersions at 500 nm was measured, resulting in a tendency similar to that obtained by visual observation. FIG. 2C shows the results of measurement of a transmittance of dispersions containing EYPC and deoxycholic acid and FIG. 2D shows the results of measurement of a transmittance of dispersions containing DLPC and deoxycholic acid. These results suggest the formation of complexes (associated products) of deoxycholic acid and the lipids. The complex of deoxycholic acid and a lipid may sometimes hereinafter referred to as "lipid-deoxycholate complex."

Next, the zeta potential of these dispersions was checked. In FIG. 3, there are shown the results of measurement of a zeta potential of a dispersion containing EYPC and deoxycholic acid (i.e. EYPC-deoxycholate complex in the figure) and a dispersion containing DLPC and deoxycholic acid (i.e. DLPC-deoxycholate complex in the figure) relative to the amount of deoxycholic acid. It will be noted that the results of FIG. 3 show an average value of five different measurements and ± is SD (standard deviation).

Both types of dispersions had the values negatively lowered in association with the complexing of deoxycholic acid. This means the complexing of deoxycholic acid having a negative charge with the lipid and indicates the formation of a mixed complex of deoxycholic acid and the lipid. In the case using either of the lipids, the zeta potential showed a value of about −30 mV in an amount of 1600 nmol of deoxycholic acid being complexed and the zeta potential value did not lower appreciably in larger amounts used for the complexing. Thus, it is considered that deoxycholic acid is so complexed as to substantially cover the surface of the resulting complex therewith in the amount indicated above.

(2) Complex Structure

According to the preparation of the pH sensitive carrier, a fluorescent substance-holding test (a test of dispersing a thin film by use of a Pyranine solution) of the complex prepared from 1600 nmol of deoxycholic acid relative to 1000 nmol of DLPC was carried out, revealing that the fluorescent substance was not held by the complex. Since the complex could not hold the fluorescent substance, it was suggested that the complex did not have a hollow structure, but was in micellar form (data not shown).

Next, the particle size of different types of complexes obtained according to the preparation of the pH sensitive carrier was measured. The results of measuring the particle size by the dynamic light scattering method revealed that the particle size (Diameter) of the EYPC-deoxycholate complex (EYPC:deoxycholic acid=1000 nmol:1600 nmol) was at about 73 nm and the particle size (Diameter) of the DLPC-deoxycholate complex (DLPC:deoxycholic acid=1000 nmol:1600 nmol) was at about 43 nm (Table 1). The polydispersity indices (PDI) of these complexes were, respectively, values as small as 0.26 and 0.07, demonstrating that the complexes of deoxycholic acid and the lipids were in the form of small-sized, uniform particles, respectively.

TABLE 1

| | Particle size and PDIs | |
|---|---|---|
| | Diameter (nm) | PDI |
| EYPC only | 411 ± 10.6 | 0.48 ± 0.03 |
| DLPC only | 306 ± 5.6 | 0.47 ± 0.03 |
| EYPC-deoxycholate | 73.1 ± 0.5 | 0.26 ± 0.01 |
| DLPC-deoxycholate | 43.1 ± 0.5 | 0.07 ± 0.01 |

The values are each an average value of five different measurements, and ± indicates SD.
EYPC only: EYPC alone
DLPC only: DLPC alone
EYPC-deoxycholate: EYPC-deoxycholate complex
DLPC-deoxycholic acid: DLPC-deoxycholate complex (3) pH Sensitivity
(Leaching Test)

Figure 4:
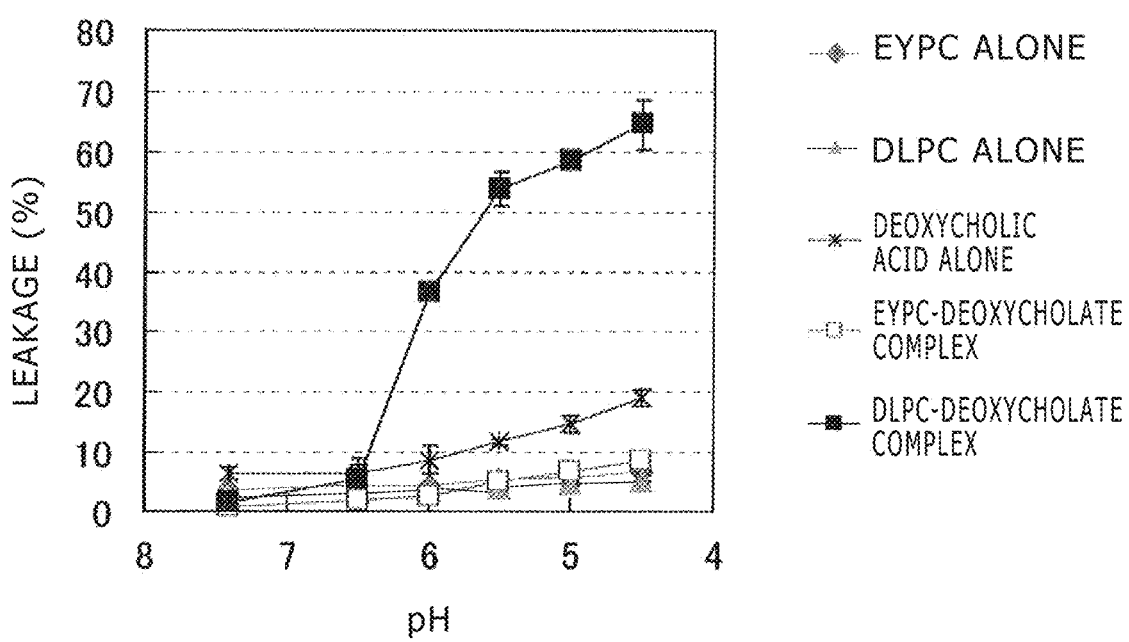
FIG. 4 is a graph showing leakages of EYPC alone, DLPC alone, deoxycholic acid alone, EYPC-deoxycholate complex and DLPC-deoxycholate complex at different pHs.

The pH sensitivities of EYPC alone, DLPC alone, EYPC-deoxycholate complex and DLPC-deoxycholate acid complex were checked. The test was carried out in such a way that a complex was prepared according to the foregoing preparation method of carrier using 1000 nmol of a lipid (EYPC or DLPC) and 1600 nmol of deoxycholic acid, followed by incubation with EYPC liposome which is a model of biological membrane according to the foregoing method for the leaching test (unless otherwise indicated, the leaching test was one resulting from 90 minutes incubation herein and whenever it appears hereinafter). FIG. 4 shows the results of measurement of the leakages of EYPC alone, DLPC alone, deoxycholic acid alone, EYPC-deoxycholate complex and DLPC-deoxycholate complex at pHs of 7.4, 6.5, 6.0, 5.5, 5.0 and 4.5. The plots in FIG. 4 are, respectively, an average value of three different measurements, and ± is SD.

EYPC alone, DLPC alone and the EYPC-deoxycholate complex did not cause the leakage of the fluorescent substance at any of pHs of from 7.4 to 4.5 and thus, showed no pH sensitivity, whereas the DLPC-deoxycholate complex caused a greater degree of leakage than deoxycholic acid alone at a pH not higher than 6.5. Thus, it was clarified that the DLPC-deoxycholate complex developed a pH sensitive, membrane disruptive function promoting effect.

According to this test, it was revealed that there could be obtained complexes obtained from the combinations of deoxycholic acid and appropriate types of amphipathic substances and capable of developing the function in response to a weakly acidic environment. The pH for the development of the effect was at not higher than 6.5 and was in a pH range enough for practical use. Since no leakage was caused at a pH in the physiological environment, the pH sensitivity was such that the function was well controlled in on-off fashion.

(Membrane Fusion Test)

Figure 5:
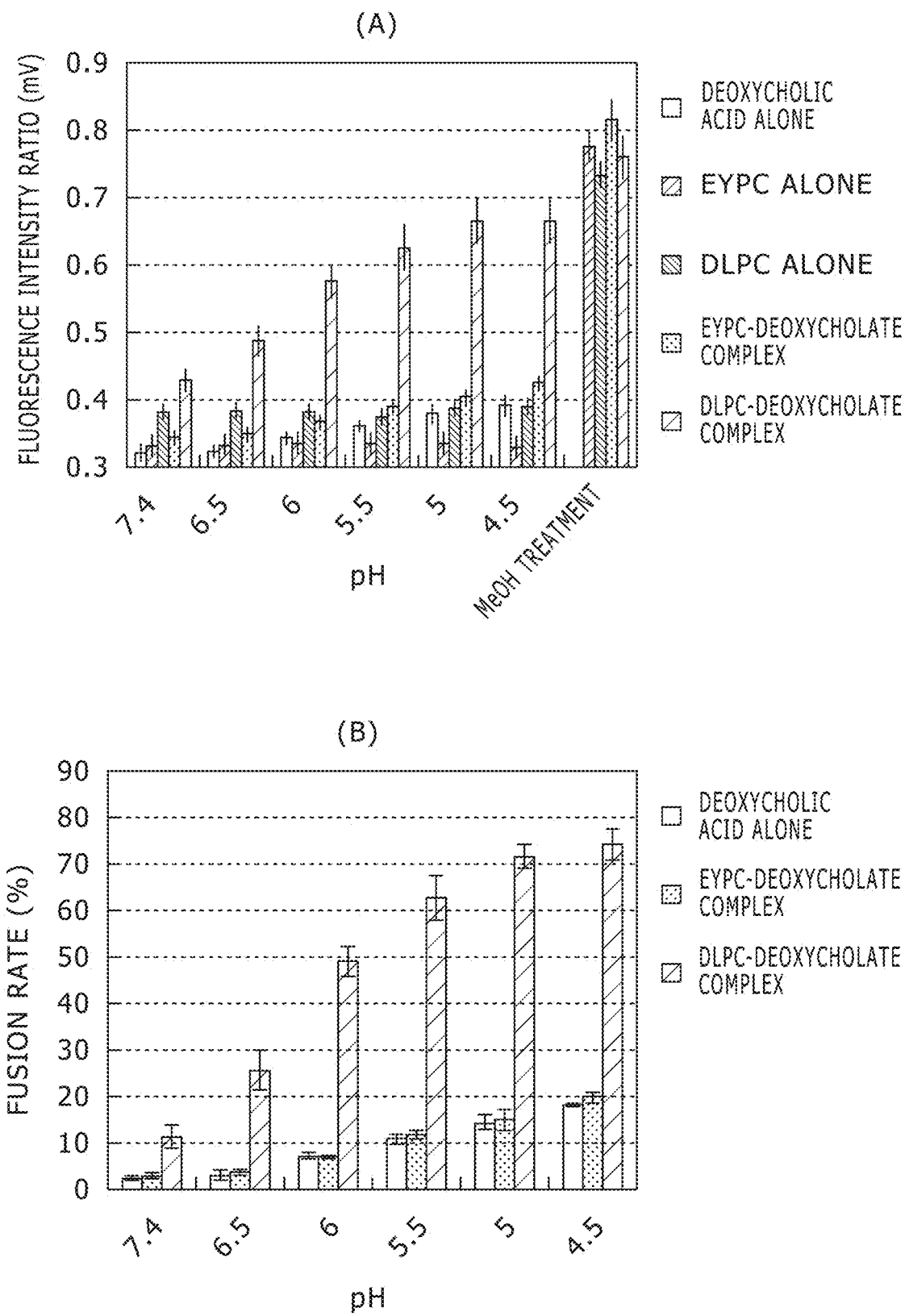
FIG. 5(A) is a graph showing fluorescent intensity ratios of the dispersions of EYPC alone, DLPC alone, deoxycholic acid alone, EYPC-deoxycholate complex and DLPC-deoxycholate complex at different pHs in case of incubation with a double fluorescence-labeled liposome.
FIG. 5(B) is a graph showing fusion rates of deoxycholic acid alone, EYPC-deoxycholate complex and DLPC-deoxycholate complex.

For delivering a physiologically active substance to cellular cytosol, it is desirable to have the function of membrane fusion in a weakly acidic environment. According to the method for the foregoing membrane fusion test, a double fluorescence-labeled EYPC liposome and the carrier (complex) prepared by use of 1000 nmol of a lipid (EYPC or DLPC) and 1600 nmol of deoxycholic acid were subjected to 60 minutes incubation at 37° C. at different pHs to check the fusion of both. FIG. 5(A) is a graph showing fluorescence intensity ratios of EYPC alone, DLPC alone, deoxycholic acid alone, EYPC-deoxycholate complex and DLPC-deoxycholate complex at pHs of 7.4, 6.5, 6.0, 5.5, 5.0 and 4.5. FIG. 5(B) is a graph showing, at the same pHs as indicated above, fusion rates of deoxycholic acid alone, EYPC-deoxycholate complex and DLPC-deoxycholate complex. The fusion rate of 0% is a fluorescence intensity ratio in case where DLPC alone or EYPC alone was added to the double fluorescence-labeled liposome and 100% indicates a value obtained by subjecting the respective samples to methanol treatment. The value of deoxycholic acid alone was calculated using a value of the double fluorescence-labeled liposome taken as 0% and a value of methanol-treated EYPC-deoxycholic acid taken as 100%. It will be noted that the plots in FIGS. 5(A) and 5(B) are each an average value of three different measurements, and ± is SD.

From the results of FIG. 5(A), it will be seen that the DLPC-deoxycholate complex increased the fluorescence intensity ratio in association with the lowering of pH and caused the fusion with the double fluorescence-labeled EYPC liposome. The evaluation of these fusion rates revealed that the DLPC-deoxycholate complex developed a membrane fusion function promoting effect in a weakly acidic environment (FIG. 5(B)). The DLPC-deoxycholate complex developed both the membrane disruptive function promoting effect and the membrane fusion function promoting effect. In view of this, it is considered that both effects are derived from the same phenomena, with the possibility that a carrier capable of developing the membrane disruptive function promoting effect also develops the membrane fusion function promoting effect.

It will be noted that the fluorescence intensity ratio at a pH of 5.0 indicated a value of about 80% of the sample subjected to methanol treatment (FIG. 5(A)). The methanol-treated sample is in a state of complete fusion between the double fluorescence-labeled liposome and the carrier, suggesting that the EYPC liposome of the biological membrane model and the prepared carrier are fused in high efficiency. Thus, highly efficient delivery of a physiologically active substance will be expected.

(4) Comparison with Ordinary pH Sensitive Liposomes

Figure 6:
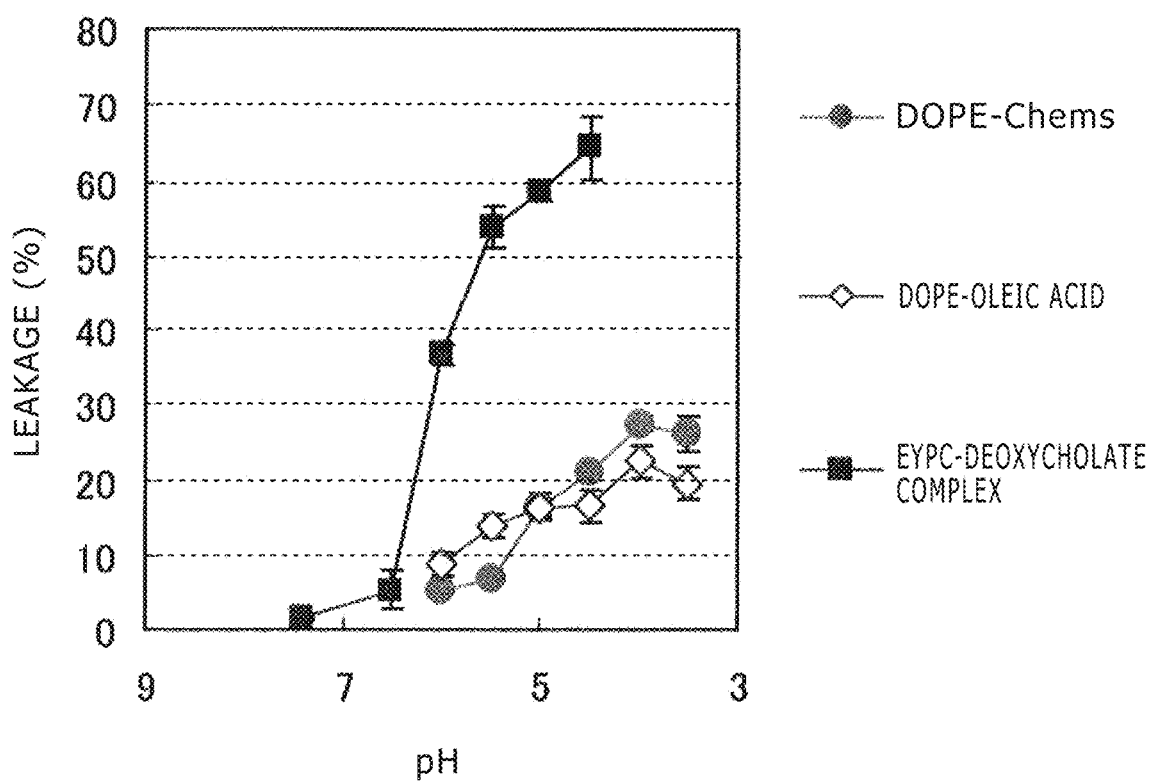
FIG. 6 is a graph showing leakages of DOPE (Dioleoyl Phosphatidylethanolamine)-Chems liposome, DOPE-oleic acid liposome and DLPC-deoxycholate complex relative to the pH.

In order to confirm the degree of pH sensitivity and leaching strength, comparison with DOPE-Chems liposome (DOPE:Chems=3:2 (by molar ratio)) and DOPE-oleic acid liposome (DOPE:oleic acid=7:3 (by molar ratio)), both of which are well known as a pH sensitive liposome, was carried out according to the leaching test. A dispersion containing a DOPE-Chems liposome or DOPE-oleic acid liposome in an amount corresponding to 20 nmol of DOPE was used for measurement. FIG. 6 is a graph showing the leakages of the DOPE-Chems liposome, DOPE-oleic acid liposome and DLPC-deoxycholate complex at different pHs. The plots of FIG. 6 are each an average of three measurements and ± is SD.

With respect to the DOPE-Chems liposome and the DOPE-oleic acid liposome, leakage started to occur at a pH of not higher than 6.0 and a leakage of 20 to 30%, which was maximum in value, was indicated at a pH of 3.5. On the other hand, the pH sensitive carrier (DLPC-deoxycholate complex) commenced to induce leakage from a pH of 6.5 and its leakage of over 60% was obtained.

The leakage of the DLPC-deoxycholate complex was higher than those of the existing pH sensitive liposomes, revealing that the illustrative pH sensitive carrier (DLPC-deoxycholate complex) has a strong effect of instabilizing and disrupting the membrane. It has been shown that the pH at which the effect is developed is closer to neutral and thus, the carrier is highly sensitive to a weakly acidic environment.

(5) Investigation of the Complexing Amount of Deoxycholic Acid

In order to check the complexing amount of deoxycholic acid necessary for the development of the effect, different amounts of deoxycholic acid were used for the preparation of pH sensitive carriers to evaluate the development of the membrane fusion function promoting effect according to the membrane fusion test.

Figure 7:
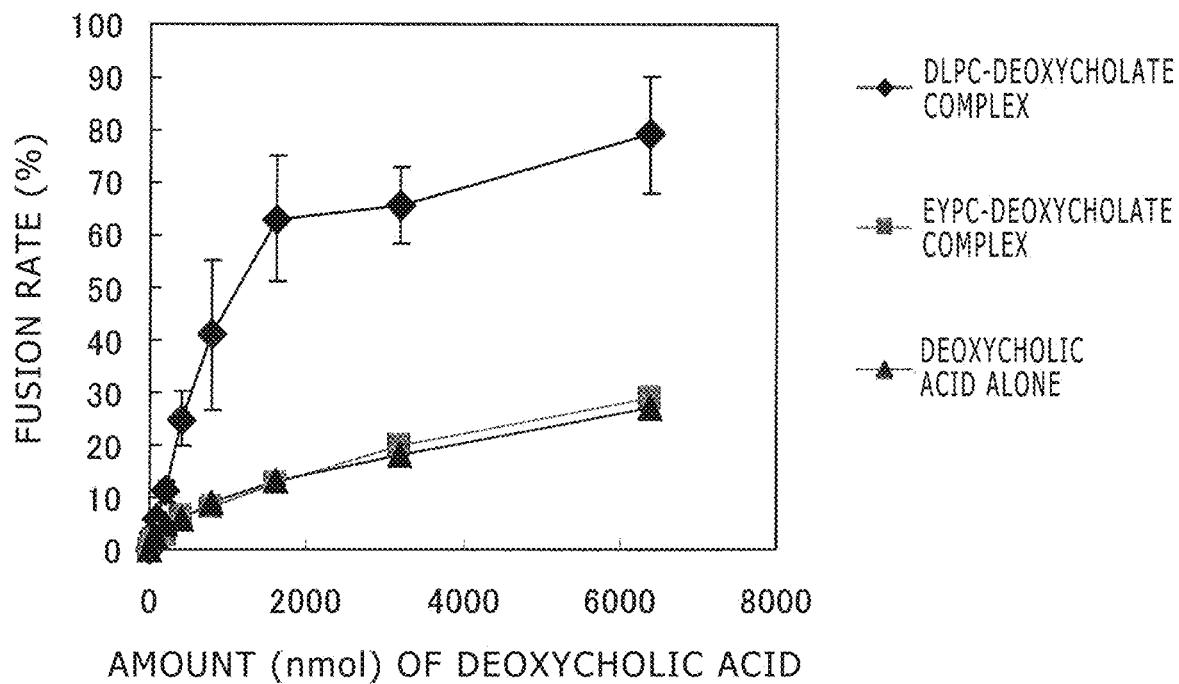
FIGS. 7(A) and 7(B) are, respectively, a graph showing fusion rates of deoxycholic acid alone, EYPC-deoxycholate complex and DLPC-deoxycholate complex in relation to the amount of deoxycholic acid.
Figure 7:
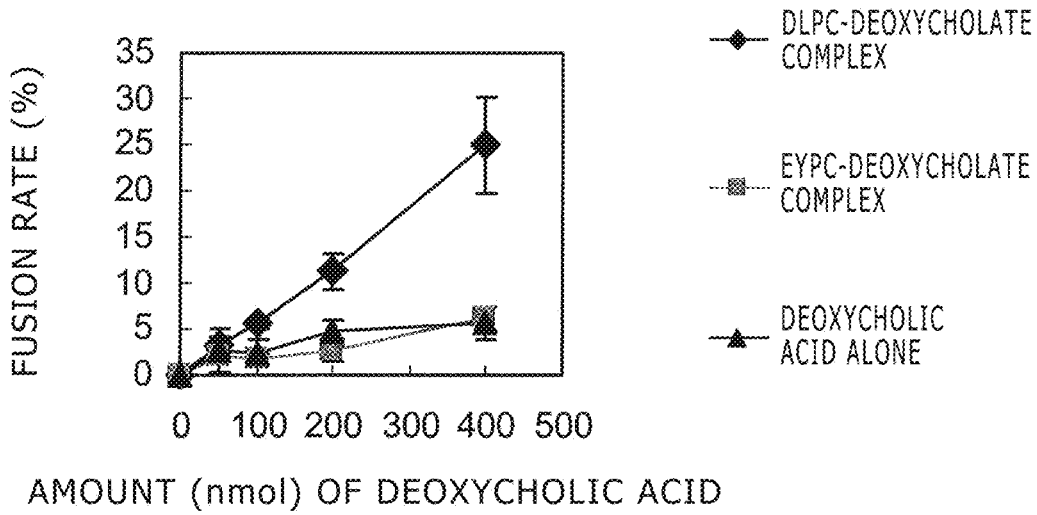

Measurement was repeated three times to calculate an average value and SD. The value of deoxycholic acid alone was calculated by using a value of a methanol-treated EYPC-deoxycholate complex. FIGS. 7(A) and 7(B), respectively, show a fusion rate of each of deoxycholic acid alone, EYPC-deoxycholate complex and DLPC-deoxycholate complex relative to the amount of deoxycholic acid.

From FIGS. 7(A) and 7(B), it can be understood that the prepared carriers exhibit a larger value than deoxycholic acid alone in a complexing amount of not less than 100 nmol and are able to develop the membrane fusion function promoting effect. It can also be understood that the development of the membrane fusion function promoting effect can be obtained by complexing 100 to 6400 nmol of deoxycholic acid with 1000 nmol of the lipid.

It will be noted that the fusion rate of the EYPC-deoxycholate complex is substantially the same value as with deoxycholic acid alone, thus showing that the EPYC-deoxycholate complex has not acquired the membrane fusion function promoting effect as a result of complexing with the pH sensitive compound.

(6) Influence of Lipid Structure

From the above investigation, it has been made clear that when deoxycholic acid and an appropriate type of lipid (amphipathic substance) are combined, there can be obtained a carrier that is able to develop the membrane disruptive function promoting effect and the membrane fusion function promoting effect in a weakly acidic environment. For the purpose of elucidating the type of lipid capable of yielding these properties, a number of carriers were prepared with lipids having a variety of structures and subjected to the leaching test or membrane fusion test.

As to the lipid structure, the influences of the length of the acyl group (10 to 18 carbon atoms) of diacylphosphatidylcholines and the unsaturated bond of the acyl group of diacylphosphatidylcholines were checked. The respective carriers were prepared using 1000 nmol of lipids and 1600 nmol of deoxycholic acid. Measurement was repeated three times, from which an average value and SD were calculated, respectively. It will be noted that the "number of carbon atoms" of amphipathic substance means the number of carbon atoms of a fatty acid moiety (acyl group) serving as the hydrophobic site of the amphipathic substance.

Figure 8:
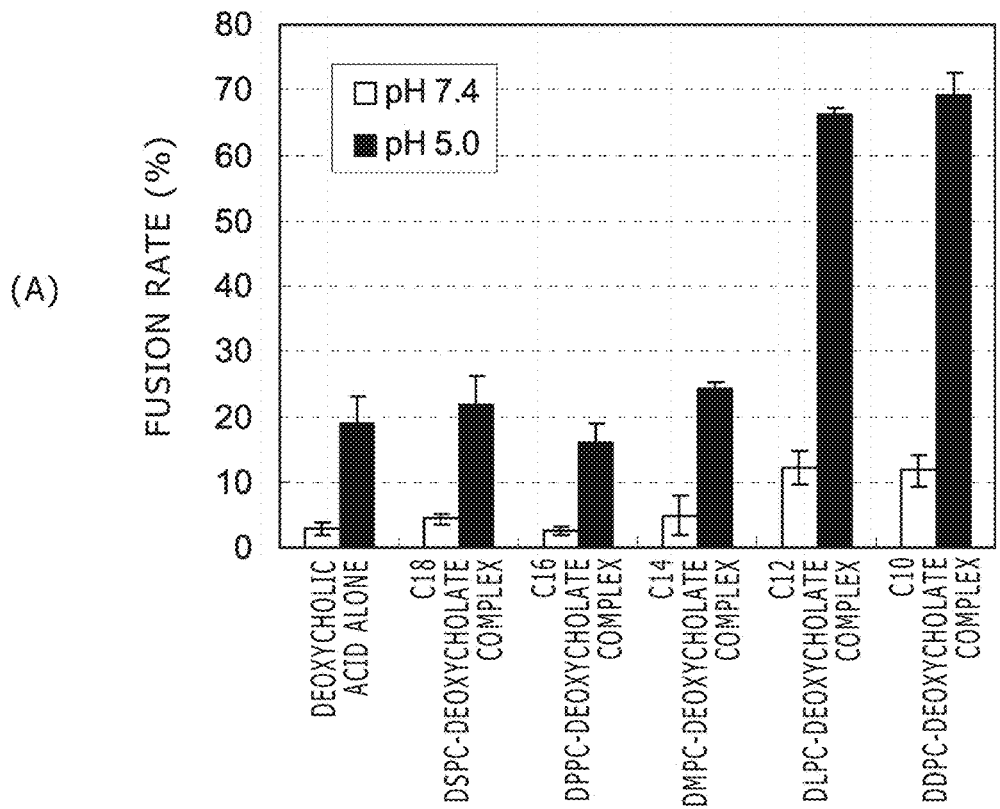
FIG. 8(A) is a graph showing fusion rates of deoxycholic acid alone, DSPC (Distearoyl Phosphatidylcholine)-deoxycholate complex, DPPC (Dipalmitoyl Phosphatidylcholine)-deoxycholate complex, DMPC (Dimyristoyl Phosphatidylcholine)-deoxycholic acid complex, DLPC-deoxycholate complex and DDPC (Didecanoyl Phosphatidylcholine)-deoxycholate complex.
FIG. 8(B) is a graph showing fusion rates of deoxycholic acid alone, HSPC (Hydrogenated Soybean Phosphatidylcholine)-deoxycholate complex, DOPC (Dioleoyl Phosphatidylcholine)-deoxycholate complex and POPC (1-Palmitoyl 2-Oleoyl Phosphatidylcholine)-deoxycholate complex.
Figure 8:
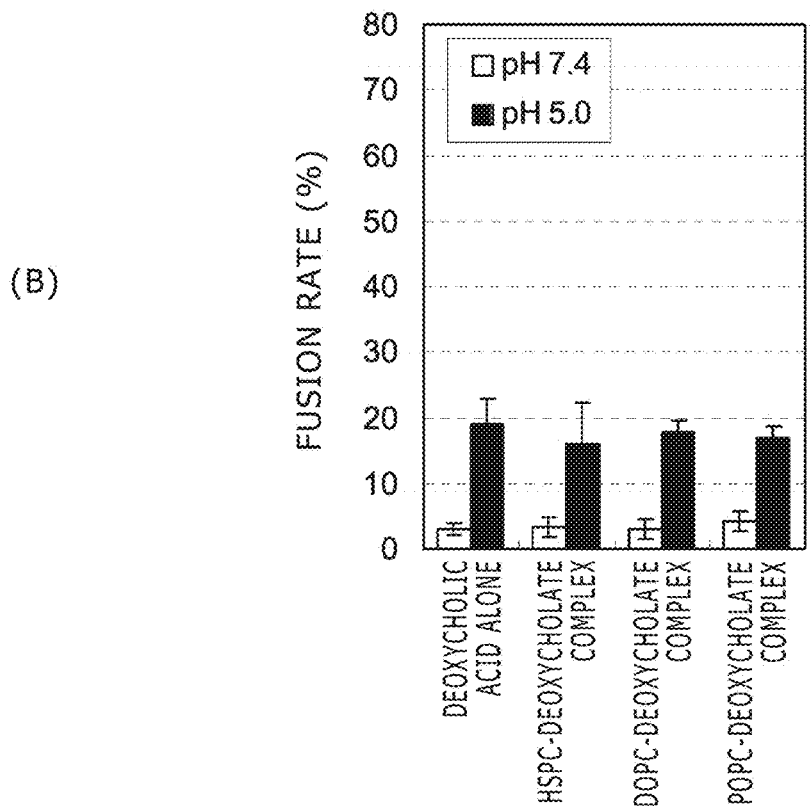

FIG. 8(A) shows the fusion rate of each of deoxycholic acid alone, DSPC-deoxycholate complex, DPPC-deoxycholate complex, DMPC-deoxycholate complex, DLPC-deoxycholate complex and DDPC-deoxycholate complex. FIG. 8(B) shows the fusion rate of each of deoxycholic acid alone, HSPC-deoxycholate complex, DOPC-deoxycholate complex and POPC-deoxycholate complex.

From FIG. 8(A), it will be seen the carriers using DSPC, DPPC and DMPC have similar values to deoxycholic acid alone and no effect was thus shown, whereas DLPC and DDPC showed the effect. It is considered that the carbon length of the lipids provides an influence and the development of the effect is obtained when using lipids having a short carbon chain. A lipid having a short carbon chain is likely to generate a flip flop that is the inversion motion of the molecule in the membrane, and this nature is considered to influence the development.

As to the influence of the unsaturated bond, the carriers using POPC having one unsaturated bond and DOPC having two unsaturated bonds in the chain with 18 carbon atoms did not develop any effect (FIG. 8(B)). Thus, it is shown that the unsaturated bond does not provide an appreciable influence on the development of the effect.

Next, the influence of the head structure of lipid on the development of the effect was checked. Carriers were prepared using 1000 nmol of lipids and 1600 nmol of deoxycholic acid, respectively. Measurement was repeated three times, from which an average value and SD were calculated, respectively.

Figure 9:
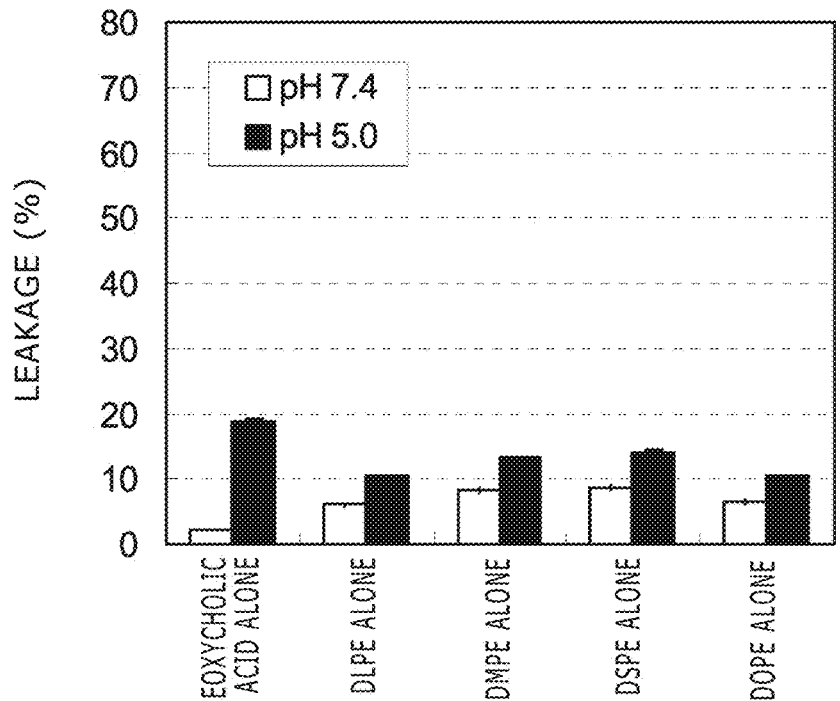
FIG. 9(A) is a graph showing leakages of deoxycholic acid alone, DLPE (Dilauroyl Phosphatidylethanolamine) alone, DMPE (Dimyristoyl Phosphatidylethanolamine) alone, DSPE (Distearoyl Phosphatidylethanolamine) alone and DOPE alone.
FIG. 9(B) is a graph showing leakages of deoxycholic acid alone, DLPE-deoxycholate complex, DMPE-deoxycholate complex, DSPE-deoxycholate complex and DOPE-deoxycholate complex.
Figure 9:
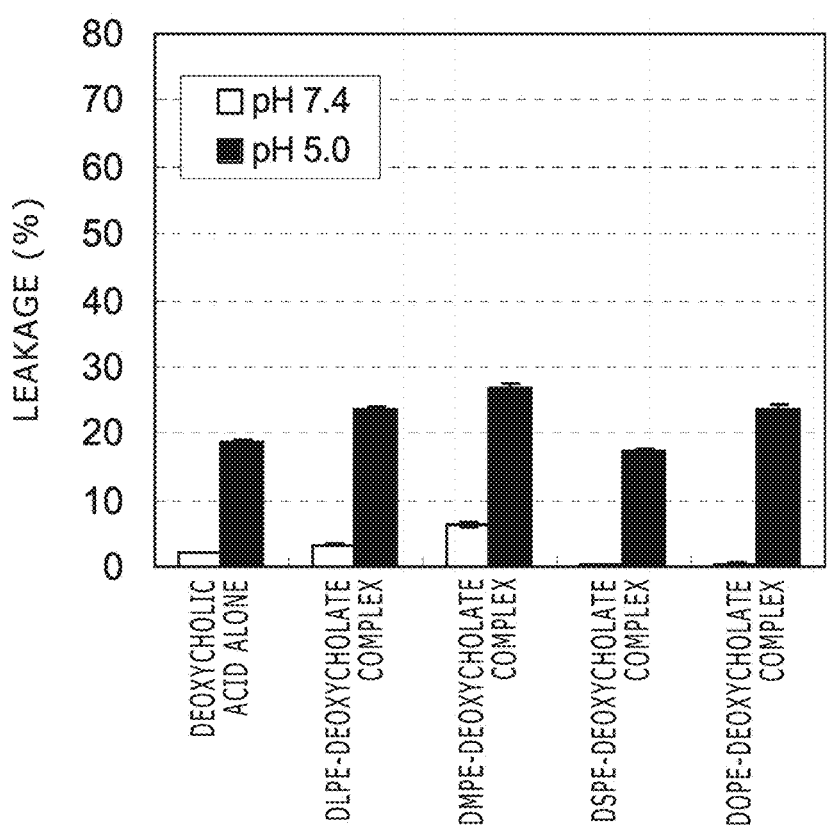

FIG. 9(A) is a graph showing the leakage of each of deoxycholic acid alone, DLPE alone, DMPE alone, DSPE alone and DOPE alone, and FIG. 9(B) is a graph showing the leakage of each of deoxycholic acid alone, DLPE-deoxycholate complex, DMPE-deoxycholate complex, DSPE-deoxycholate complex and DOPE-deoxycholate complex.

None of the lipids having PE resulted in the development of the effect, revealing that the choline group is preferred as the head structure (FIGS. 9(A) and 9(B)).

From the above results, it has been demonstrated that for an amphipathic substance capable of yielding the development of the effect, it is preferred to use unsaturated or saturated lipids having a choline group as a head structure and having a chain of 10 to 12 carbon atoms.

(7) Investigation of Other Types of Amphipathic Substances

Substances other than lipid have been utilized for the delivery of the physiologically active substance. Moreover, it is known that deoxycholic acid forms complexes with hydrophobic substances other than a lipid, with the possibility that there can be obtained carriers having functions in association with a variety of substances. To this end, a variety of substances and deoxycholic acid were complexed to prepare carriers, which were evaluated by the leaching test. Since deoxycholic acid alone invites an increasing leakage by the action of its surface activity, screening was carried out in such a way that a substance that is able to yield the development of the effect is defined to satisfy both of the requirements: (1) in the leaching test, a leakage at a given pH of less than a physiological pH increases over a leakage at the physiological pH and its increase increment is larger than an increase increment obtained in case where a pH sensitive compound alone is used for the test; and (2) in a leaching test at a given pH less than the physiological pH, a leakage at the time when a complex (pH sensitive carrier) is formed from a pH sensitive compound and an amphipathic substance is larger than the sum of a leakage of the pH sensitive compound alone and a leakage of the amphipathic substance alone.

It will be noted that to satisfy (1) and (2) above means to satisfy both of the following relations of leakage Lc of a pH sensitive carrier (complex of a pH sensitive compound and an amphipathic substance), La of the pH sensitive compound alone and Lb of the amphipathic substance. More particularly, (1) above is represented by the following formula (1), and (2) above is represented by the following formula (2). In the following formulas, leakages at a pH of 7.4 are, respectively, represented by $Lc_{7.4}$, $La_{7.4}$ and $Lb_{7.4}$, and leakages at a pH of 5.0 or 4.5 are, respectively, represented by $Lc_x$, $La_x$ and $Lb_x$.

$$\Delta = (Lc_x - Lc_{7.4}) - (La_x - La_{7.4}) > 0 \qquad \text{Formula (1)}$$

$$\Delta' = Lc_x - (La_x + Lb_x) > 0 \qquad \text{Formula (2)}$$

The results are shown in Tables 2 to 7. It will be noted that the respective values indicated in Tables 2 to 7 are an average value of three measurements and ± is SD.

Figure 10:
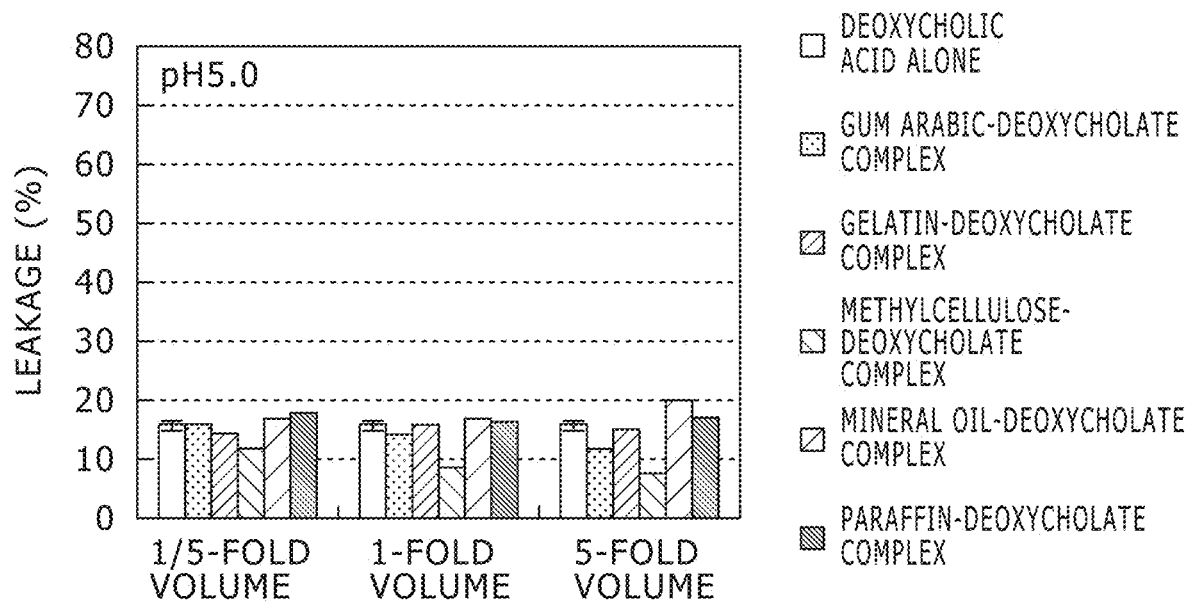
FIG. 10 is a graph showing leakages of complexes of deoxycholic acid with macromolecular materials at a pH of 5.0.

Furthermore, 1600 nmol (663 μg) of deoxycholic acid and different weights of macromolecular materials were used to prepare particles, followed by evaluating the occurrence of leakage at a pH of 5.0. In FIG. 10, there are shown the results of leakage of the complexes of deoxycholic acid and macromolecular materials at a pH of 5.0. It will be noted that the values in FIG. 10 are those values of one measurement, respectively.

TABLE 2

Functional evaluation of particles prepared using a variety of amphipathic substances

| Hydrophobic material | | Deoxycholate complexed particle Leakage (%) | Hydrophobic material only Leakage (%) |
|---|---|---|---|
| Deoxycholate only | pH 7.4 | 1.0 ± 0.2 | — |
| | pH 5.0 | 14.6 ± 0.6 | — |
| Tween 20 | pH 7.4 | 61.5 ± 2.1 | 59.5 ± 1.8 |
| | pH 5.0 | 80.2 ± 3.4 | 61.9 ± 0.5 |
| Tween 40 | pH 7.4 | 8.9 ± 0.2 | 7.9 ± 0.5 |
| | pH 5.0 | 40.0 ± 0.3 | 9.8 ± 0.7 |
| Tween 60 | pH 7.4 | 2.9 ± 0.1 | 2.4 ± 0.2 |
| | pH 5.0 | 29.6 ± 0.5 | 6.3 ± 0.2 |
| Tween 80 | pH 7.4 | 7.0 ± 0.8 | 7.3 ± 0.1 |
| | pH 5.0 | 35.7 ± 1.0 | 10.8 ± 0.4 |
| Tween 65 | pH 7.4 | 7.5 ± 0.4 | 7.1 ± 0.7 |
| | pH 5.0 | 16.4 ± 0.6 | 8.3 ± 0.7 |
| Tween 85 | pH 7.4 | 5.8 ± 0.2 | 5.1 ± 0.7 |
| | pH 5.0 | 15.1 ± 0.6 | 6.3 ± 0.2 |
| PEG 20 stearyl ether | pH 7.4 | 69.5 ± 3.8 | 70.3 ± 2.2 |
| | pH 5.0 | 78.3 ± 0.7 | 72.0 ± 3.1 |
| PEG 23 lauryl ether | pH 7.4 | 2.9 ± 0.2 | 2.0 ± 0.1 |
| | pH 5.0 | 13.3 ± 0.4 | 4.7 ± 0.6 |

TABLE 3

Functional evaluation of particles prepared using a variety of amphipathic substances

| Hydrophobic material | | Deoxycholate complexed particle Leakage (%) | Hydrophobic material only Leakage (%) |
|---|---|---|---|
| Castor oil | pH 7.4 | 2.2 ± 0.4 | 4.4 ± 0.6 |
| | pH 5.0 | 14.5 ± 0.2 | 7.3 ± 0.3 |

TABLE 3-continued

Functional evaluation of particles prepared using a variety of amphipathic substances

| Hydrophobic material | | Deoxycholate complexed particle Leakage (%) | Hydrophobic material only Leakage (%) |
|---|---|---|---|
| PEG10-castor oil | pH 7.4 | 2.3 ± 0.3 | 1.2 ± 0.7 |
| | pH 5.0 | 26.0 ± 0.4 | 3.4 ± 0.6 |
| PEG10-hardened castor oil | pH 7.4 | 0.7 ± 0.4 | 0.3 ± 0.2 |
| | pH 5.0 | 14.6 ± 1.1 | 2.9 ± 0.2 |
| PEG40-hardened castor oil | pH 7.4 | 0.1 ± 0.1 | 0.6 ± 0.3 |
| | pH 5.0 | 6.0 ± 0.5 | 3.1 ± 0.5 |
| PEG60-hardened castor oil | pH 7.4 | 1.0 ± 0.6 | 0.7 ± 0.6 |
| | pH 5.0 | 5.3 ± 0.8 | 2.5 ± 0.6 |
| SPAN 20 | pH 7.4 | 4.9 ± 0.3 | 5.7 ± 0.7 |
| | pH 5.0 | 21.0 ± 0.6 | 10.1 ± 0.4 |
| SPAN 40 | pH 7.4 | 24.0 ± 1.9 | 14.9 ± 0.8 |
| | pH 5.0 | 50.4 ± 3.7 | 20.8 ± 1.4 |
| SPAN 60 | pH 7.4 | 5.1 ± 0.4 | 7.9 ± 0.3 |
| | pH 5.0 | 36.0 ± 1.4 | 17.5 ± 0.4 |
| SPAN 80 | pH 7.4 | 3.9 ± 0.1 | 5.1 ± 0.5 |
| | pH 5.0 | 27.8 ± 0.7 | 10.0 ± 0.7 |

TABLE 4

Functional evaluation of particles prepared using a variety of amphipathic substances

| Hydrophobic material | | Deoxycholate complexed particle Leakage (%) | Hydrophobic material only Leakage (%) |
|---|---|---|---|
| Ethyl oleate | pH 7.4 | 4.6 ± 0.3 | 7.9 ± 0.2 |
| | pH 5.0 | 22.1 ± 0.1 | 11.2 ± 1.3 |
| Ethyl octanoate | pH 7.4 | 3.0 ± 0.3 | 9.0 ± 1.0 |
| | pH 5.0 | 19.3 ± 1.2 | 11.1 ± 1.1 |
| Ethyl laurate | pH 7.4 | 5.0 ± 0.5 | 8.7 ± 0.9 |
| | pH 5.0 | 23.2 ± 5.5 | 11.9 ± 1.2 |
| L-Phenyl-alanine | pH 7.4 | 3.4 ± 0.5 | 7.9 ± 0.5 |
| | pH 5.0 | 18.8 ± 1.0 | 10.7 ± 0.4 |
| L-Leucine | pH 7.4 | 1.2 ± 0.8 | 7.3 ± 0.2 |
| | pH 5.0 | 17.6 ± 0.5 | 13.2 ± 3.7 |
| L-Histidine | pH 7.4 | 0.5 ± 0.1 | 6.7 ± 0.4 |
| | pH 5.0 | 15.2 ± 0.9 | 8.9 ± 0.5 |
| Soybean oil | pH 7.4 | 2.1 ± 0.3 | 7.2 ± 0.1 |
| | pH 5.0 | 17.6 ± 0.3 | 9.3 ± 0.2 |
| Tricaproin | pH 7.4 | 3.0 ± 0.9 | 6.9 ± 0.9 |
| | pH 5.0 | 17.6 ± 3.4 | 8.4 ± 0.9 |
| Tricaprylin | pH 7.4 | 1.6 ± 0.4 | 6.8 ± 0.9 |
| | pH 5.0 | 16.4 ± 1.9 | 9.0 ± 1.1 |

TABLE 5

Functional evaluation of particles prepared using a variety of amphipathic substances

| Hydrophobic material | | Deoxycholate complexed particle Leakage (%) | Hydrophobic material only Leakage (%) |
|---|---|---|---|
| SPAN 65 | pH 7.4 | 3.0 ± 0.2 | 4.2 ± 0.4 |
| | pH 5.0 | 46.6 ± 1.5 | 13.0 ± 0.3 |
| SPAN 85 | pH 7.4 | 7.0 ± 0.6 | 5.2 ± 0.4 |
| | pH 5.0 | 78.7 ± 1.2 | 17.7 ± 1.2 |
| 1-Butanol | pH 7.4 | 2.7 ± 0.7 | 8.8 ± 0.1 |
| | pH 5.0 | 18.6 ± 0.7 | 11.1 ± 0.5 |
| 1-Octanol | pH 7.4 | 3.0 ± 0.7 | 9.0 ± 0.3 |
| | pH 5.0 | 19.2 ± 1.2 | 11.7 ± 0.1 |

TABLE 5-continued

Functional evaluation of particles prepared using a variety of amphipathic substances

| Hydrophobic material | | Deoxycholate complexed particle Leakage (%) | Hydrophobic material only Leakage (%) |
|---|---|---|---|
| 1-Dodecanol | pH 7.4 | 2.7 ± 0.7 | 7.9 ± 0.2 |
| | pH 5.0 | 14.1 ± 0.6 | 9.1 ± 0.8 |
| 1-Hexa-dodecanol | pH 7.4 | 6.9 ± 0.3 | 9.0 ± 0.9 |
| | pH 5.0 | 24.0 ± 1.0 | 11.0 ± 0.5 |
| 1-Eicosanol | pH 7.4 | 2.8 ± 0.3 | 7.6 ± 0.4 |
| | pH 5.0 | 20.8 ± 2.1 | 8.6 ± 0.5 |
| Lauric acid | pH 7.4 | 1.8 ± 0.2 | 6.2 ± 0.4 |
| | pH 5.0 | 17.0 ± 1.0 | 14.2 ± 0.4 |
| Oleic acid | pH 7.4 | 4.0 ± 0.5 | 2.2 ± 0.1 |
| | pH 5.0 | 87.2 ± 5.9 | 76.0 ± 2.3 |

TABLE 6

Functional evaluation of particles prepared using a variety of amphipathic substances

| Hydrophobic material | | Deoxycholate complexed particle Leakage (%) | Hydrophobic material only Leakage (%) |
|---|---|---|---|
| Benzyl benzoate | pH 7.4 | 0.6 ± 0.1 | 7.3 ± 2.0 |
| | pH 5.0 | 11.8 ± 1.0 | 9.7 ± 0.5 |
| Propyl para-oxybenzoate | pH 7.4 | 0.5 ± 0.1 | 5.4 ± 0.2 |
| | pH 5.0 | 14.0 ± 0.4 | 7.9 ± 0.1 |
| Ascorbyl palmitate | pH 7.4 | 0.5 ± 0.4 | 1.7 ± 0.1 |
| | pH 5.0 | 11.7 ± 0.7 | 9.9 ± 1.0 |
| Cyclodextrin | pH 7.4 | 1.6 ± 0.2 | 6.3 ± 0.6 |
| | pH 5.0 | 16.4 ± 0.9 | 9.0 ± 0.7 |
| Cholesterol | pH 7.4 | 1.9 ± 0.2 | 4.8 ± 0.1 |
| | pH 5.0 | 15.0 ± 0.2 | 7.6 ± 0.5 |
| Lactose | pH 7.4 | 1.3 ± 0.1 | 6.1 ± 0.2 |
| | pH 5.0 | 18.3 ± 0.4 | 8.9 ± 0.2 |
| Squalene | pH 7.4 | 1.3 ± 0.2 | 5.4 ± 0.4 |
| | pH 5.0 | 18.6 ± 1.4 | 9.0 ± 0.5 |
| Squalane | pH 7.4 | 0.9 ± 0.2 | 7.8 ± 0.6 |
| | pH 5.0 | 20.9 ± 0.7 | 9.4 ± 0.5 |
| α-Tocopherol | pH 7.4 | 5.7 ± 0.8 | 5.4 ± 0.2 |
| | pH 5.0 | 39.5 ± 6.4 | 8.8 ± 0.6 |
| α-Tocopherol acetate | pH 7.4 | 1.0 ± 0.3 | 5.9 ± 0.2 |
| | pH 5.0 | 18.0 ± 1.0 | 7.0 ± 2.1 |

TABLE 7

Functional evaluation of particles prepared using a variety of amphipathic substances

| Hydrophobic material | | Deoxycholate complexed particle Leakage (%) | Hydrophobic material only Leakage (%) |
|---|---|---|---|
| Monocaprin | pH 7.4 | 1.2 ± 0.6 | 4.0 ± 2.6 |
| | pH 5.0 | 13.9 ± 0.8 | 8.1 ± 0.2 |
| Monocaprylin | pH 7.4 | 0.8 ± 0.5 | 4.9 ± 1.8 |
| | pH 5.0 | 14.6 ± 0.7 | 8.5 ± 0.4 |
| Monolaurin | pH 7.4 | 3.1 ± 0.5 | 3.6 ± 0.3 |
| | pH 5.0 | 14.3 ± 0.6 | 5.6 ± 0.4 |
| Monomyristin | pH 7.4 | 4.0 ± 0.6 | 3.8 ± 0.3 |
| | pH 5.0 | 13.5 ± 0.4 | 5.4 ± 0.1 |
| Monopalmitin | pH 7.4 | 6.9 ± 0.6 | 7.8 ± 2.5 |
| | pH 5.0 | 19.3 ± 0.4 | 8.1 ± 0.7 |
| Monostearin | pH 7.4 | 7.0 ± 0.6 | 7.9 ± 1.0 |
| | pH 5.0 | 23.8 ± 0.8 | 9.6 ± 0.6 |
| Monoolein | pH 7.4 | 38.4 ± 3.0 | 6.3 ± 0.4 |
| | pH 5.0 | 71.3 ± 2.1 | 8.3 ± 0.4 |

TABLE 7-continued

Functional evaluation of particles prepared using a variety of amphipathic substances

| Hydrophobic material | | Deoxycholate complexed particle Leakage (%) | Hydrophobic material only Leakage (%) |
|---|---|---|---|
| Glycerol distearate | pH 7.4 | 6.2 ± 0.3 | 8.0 ± 0.2 |
| | pH 5.0 | 28.4 ± 1.6 | 11.0 ± 1.4 |
| Glycerol dioleate | pH 7.4 | 8.0 ± 0.4 | 7.2 ± 0.5 |
| | pH 5.0 | 24.1 ± 0.7 | 7.4 ± 0.6 |
| α,α Dilaurin | pH 7.4 | 11.0 ± 1.6 | 7.6 ± 1.0 |
| | pH 5.0 | 25.3 ± 1.1 | 7.4 ± 0.6 |

From the above investigation, it has been shown that appropriate substances are those including: Tween 20, Tween 40, Tween 60 and Tween 80, which are polyoxyethylene sorbitan monofatty acid esters having 12 to 18 carbon atoms; SPAN 40, SPAN 60, SPAN 80, SPAN 65 and SPAN 85, which are sorbitan fatty acid esters having 16 to 18 carbon atoms; glycerol derivatives such as glycol monooleate (monoolein in the table), glycerol distearate, glycerol dioleate and glycerol dilaurate (α,α dilaurin); PEG-10-castor oil which is polyoxyethylene castor oil; and α-tocopherol. It will be noted that the "number of carbon atoms" of the amphipathic substance means the number of carbon atoms of a fatty acid moiety (acyl group) serving as the hydrophobic site of the amphipathic substance.

(8) Investigation of the Ratio of Amphipathic Substance

The investigation of (7) above revealed amphipathic substances which are capable of bringing about the development of the effect and those substances which are not. Next, it was checked what ratio of a substance capable of bringing about the development of the effect was necessary to realize the development of the effect. EYPC was chosen as a substance not bringing about the development of the effect and DLPC or SPAN 85 was mixed with EYPC at different ratios to make a total of 1000 nmol and carriers made of a plurality of amphipathic substances were prepared.

DLPC or SPAN 85 was mixed with EYPC at different ratios to make a total of 1000 nmol, followed by complexing with 1600 nmol of deoxycholic acid to prepare carriers. The respective carriers were subjected to a leaching test at pHs of 7.4 and 5.0 to check the effect development.

Figure 11:
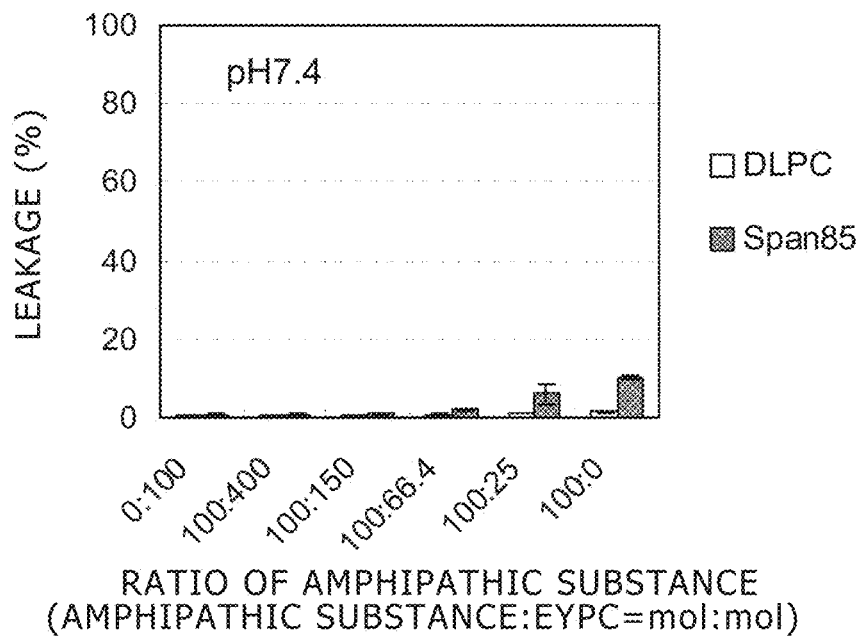
FIG. 11 is a graph showing leakages of complexes of EYPC, deoxycholic acid and DLPC or SPAN 85 at a pH of 7.4 in (A) and a pH of 5.0 in (B).
Figure 11:
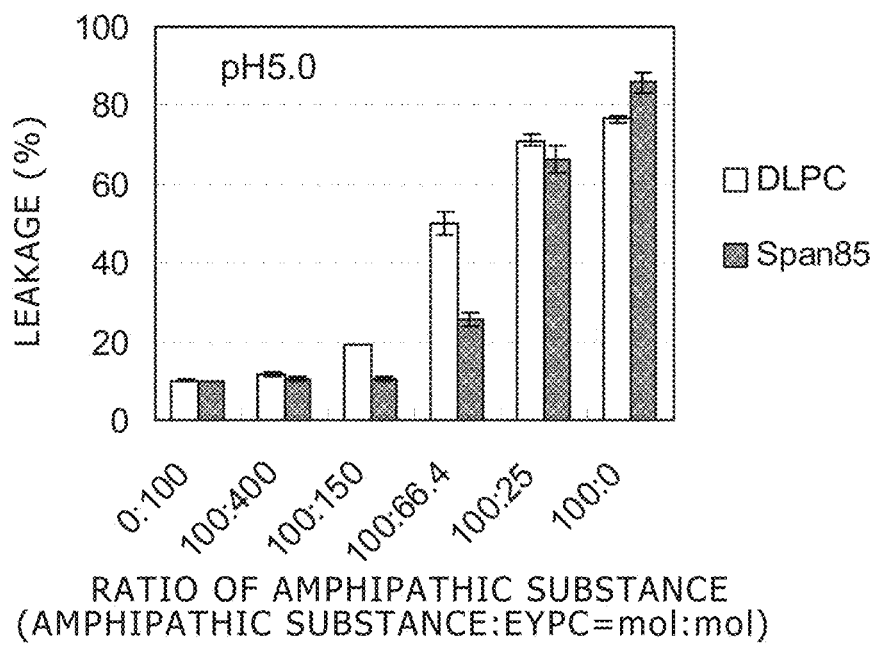

FIG. 11 shows the leakage of each of the complexes of EYPC, deoxycholic acid and DLPC or SPAN 85 at a pH of 7.4 in (A) and at a pH of 5.0 in (B). The respective values in FIGS. 11(A) and (B) are an average value of three different measurements and ± is SD.

When the ratio of DLPC or SPAN 85:EYPC (mol:mol) is within the range of 100:150 to 100:0, the pH sensitive leakage was confirmed (FIGS. 11(A) and (B)). It was thus revealed that in order to obtain a pH sensitive carrier capable of developing the effect in a weakly acidic environment as a result of complexing with deoxycholic acid, the ratio of an appropriate type of amphipathic substance was desirably within such a range as indicated above.

(9) Research of pH Sensitive Compounds Other than Deoxycholic Acid

From the above results, it was found that deoxycholic acid affected the state of hydrophobic association in a weakly acidic environment. Thus, it will be expected that molecules having structures analogous to deoxycholic acid likewise can provide a pH sensitive carrier. Then, there were selected, as an analogous molecule of deoxycholic acid, a variety of bile acids, glycyrrhizic acid and glycyrrhetinic acid, followed by carrying out a leaching test and a membrane fusion test of complexes of the above acids and DLPC to check whether they could be usable as a pH sensitive compound.

1000 nmol of DLPC and 1600 nmol of a variety of acids (hereinafter referred to as candidate compounds) were used to prepare carriers.

Figure 12:
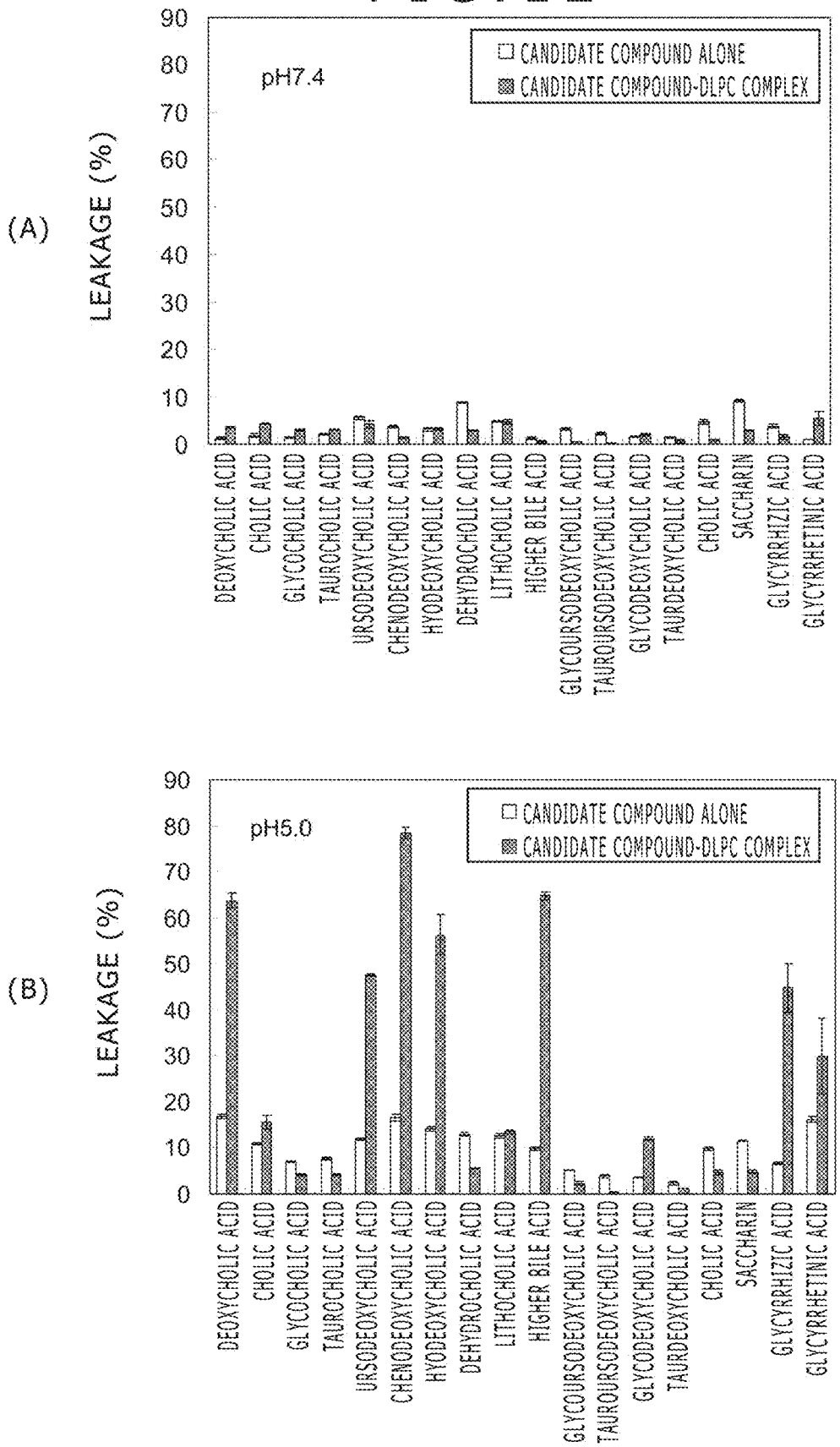
FIG. 12 is a graph showing leakages of complexes of DLPC and various types of candidate compounds at a pH of 7.4 in (A) and a pH of 5.0 in (B).

FIG. 12 shows leakages of complexes of DLPC and a variety of candidate compounds at a pH of 7.4 in (A) and a pH of 5.0 in (B). The respective values in FIG. 12 are an average value of three different measurements and ± is SD.

Figure 13:
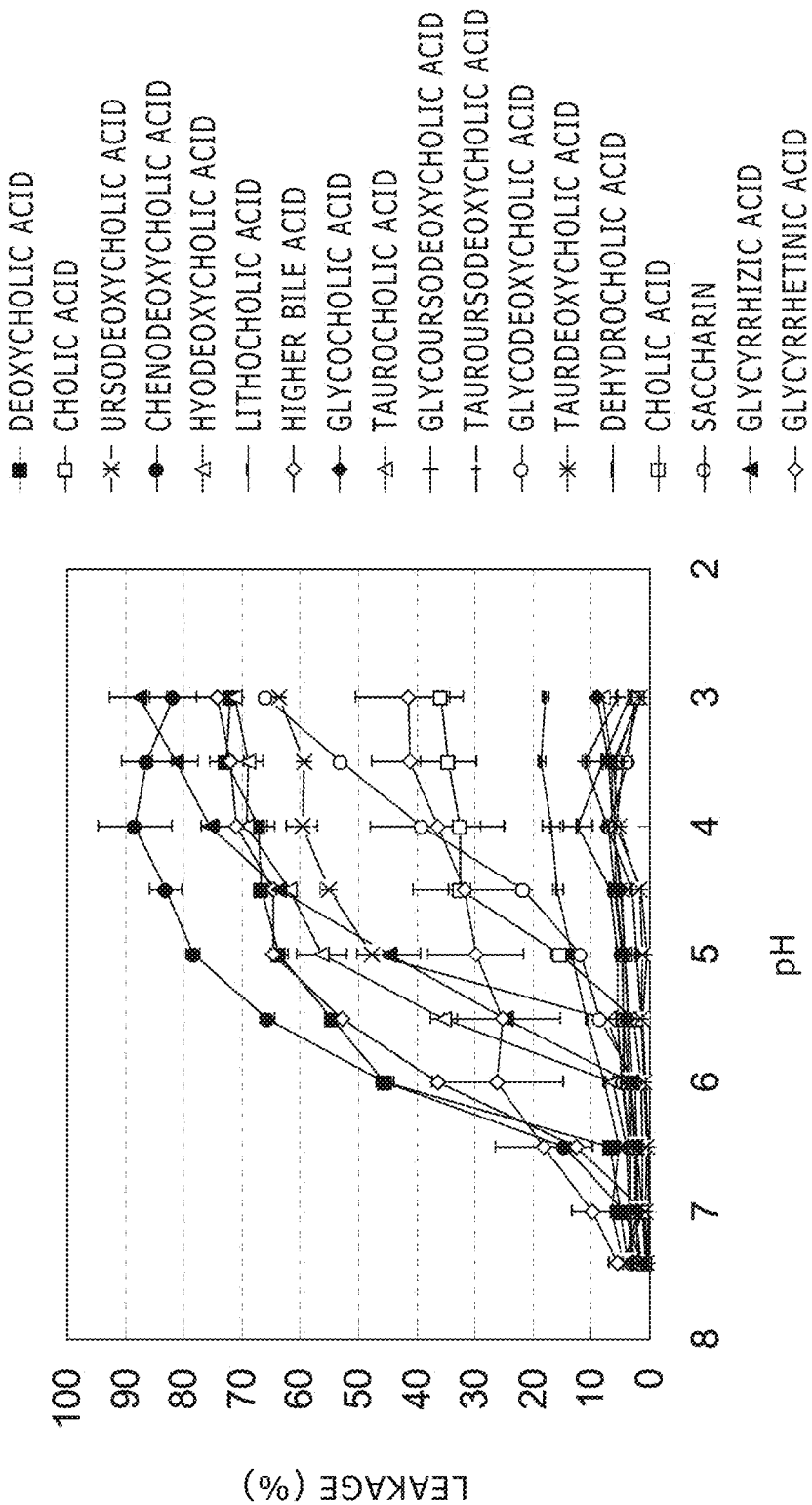
FIG. 13 is a graph showing leakages of complexes of DLPC and various types of candidate compounds relative to the pH.

In FIG. 13, there is shown a graph showing leakages of complexes of DLPC and a variety of candidate compounds at different pHs. The respective values in FIG. 13 are an average value of three different measurements and ± is SD.

Figure 14:
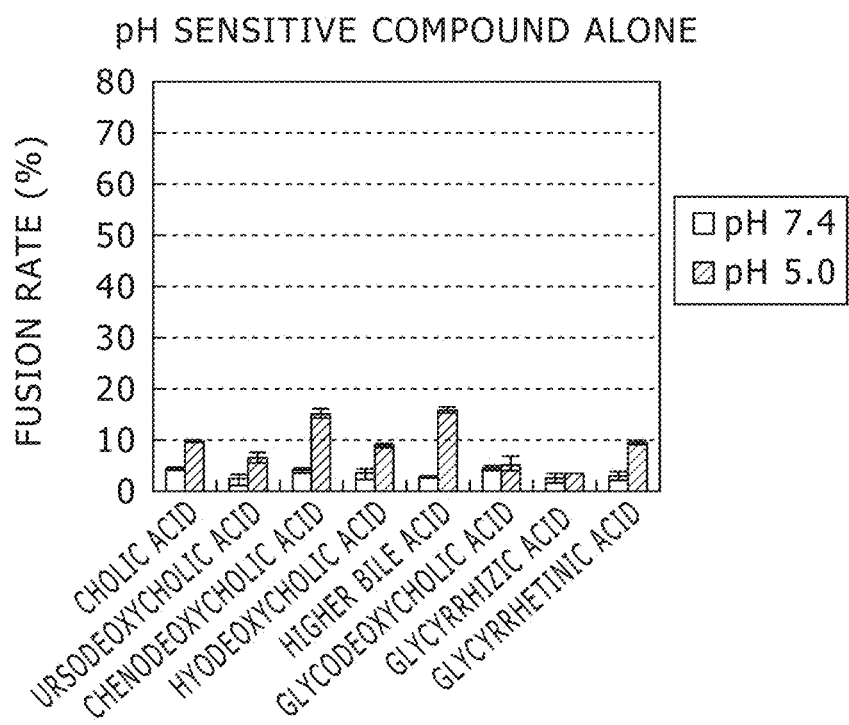
FIG. 14 is a graph showing fusion rates of various types of pH sensitive compounds when used alone in (A) and complexes of DLPC and various types of pH sensitive compounds in (B).
Figure 14:
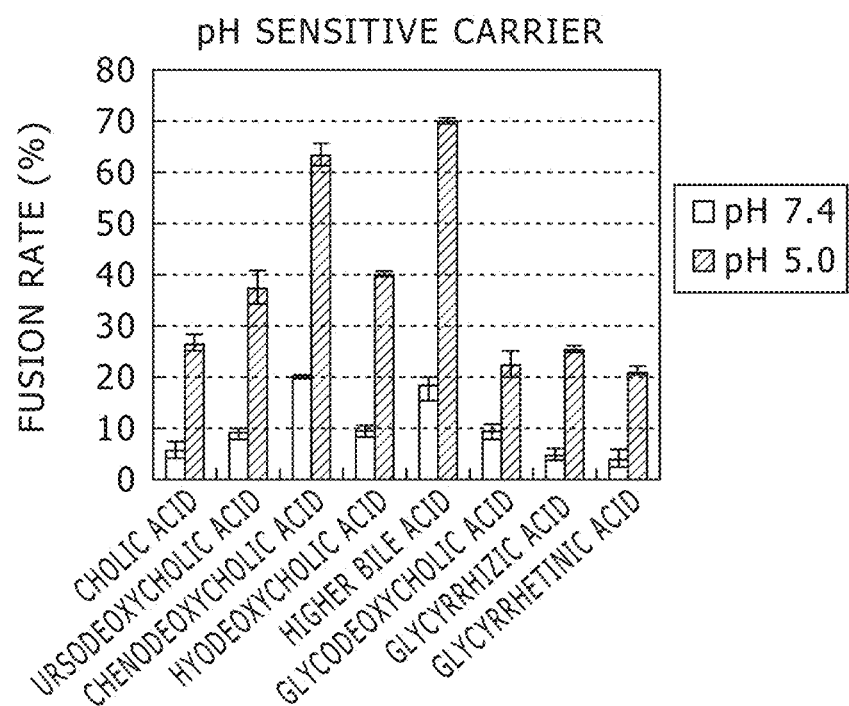

FIG. 14 shows the fusion rates of (A) a variety of pH sensitive compounds alone and (B) complexes of DLPC and a variety of pH sensitive compounds at a pH of 7.4 and a pH of 5.0. The respective values are an average value of three different measurements and ± is SD.

The carriers prepared from all the candidate compounds did not cause leakage at a pH of 7.4, whereas at a pH of 5.0, the carriers prepared by use of deoxycholic acid, cholic acid, ursodeoxycholic acid, chenodeoxycholic acid, hyodeoxycholic acid, C27 bile acid (trihydroxycholestanoic acid), glycodeoxycholic acid, glycyrrhizic acid and glycyrrhetinic acid significantly caused a greater leakage than with the cases wherein the candidate compounds alone were added, thereby showing a membrane disruptive function promoting effect (FIGS. 12(A) and (B)). It was confirmed that these carriers also had a pH sensitive membrane fusion function promoting effect (FIGS. 14(A) and (B)). In view of the results in FIGS. 5(A) and 5(B), it was shown that the illustrative carriers developed the fusion function promoting effect along with the membrane disruptive function promoting effect.

When the pH profile of these carriers was checked, it was found that the pH at which leakage started differed depending on the type of molecule used (FIG. 13). It is theorized that the pKa differs and the manner of forming association with an amphipathic substance differs, both depending on the type of molecule. These results reveal that it is possible to select in detail a pH at which the effect develops. Thus, it can be expected to enable detailed settings of in vivo delivery and intracellular delivery. According to this test, it was elucidated that these pH sensitive carriers had the effects at a pH of 7 to 3.

(10) Investigation of the Combinations of pH Sensitive Compounds and Amphipathic Substances The presence or absence of the effect development was confirmed and checked with respect to many combinations of the compounds (pH sensitive compounds) having analogous structures to deoxycholic acid and determined in FIGS. 12(A) and (B), FIG. 13 and FIGS. 14(A) and (B) to yield the development of the effect and the amphipathic substances determined by the screening in Tables 2 to 7 and in FIG. 10 to bring about the development of the effect.

Carriers were prepared using 1000 nmol of an amphipathic substance and 100 nmol of a pH sensitive compound, or 1000 nmol of an amphipathic substance and 6400 nmol of a pH sensitive compound. In Tables 8 and 9, there are shown the results of the leaching test of a variety of complexes of pH sensitive compounds and amphipathic substances.

TABLE 8

Evaluation of functional carriers obtained by combinations of pH sensitive compounds (100 nmol) and amphipathic substances (1000 nmol) (leaching test) (n = 1 in the test)

| | Deoxycholic acid | | Cholic acid | | Ursodeoxy-cholic acid | | Chenoxy-cholic acid | | Hyodeoxy-cholic acid | | Glycodeoxy-cholic acid | | Glycyrrhizic acid | |
|---|---|---|---|---|---|---|---|---|---|---|---|---|---|---|
| | $\Delta$ | $\Delta'$ | $\Delta$ | $\Delta'$ | $\Delta$ | $\Delta'$ | $\Delta$ | $\Delta'$ | $\Delta$ | $\Delta'$ | $\Delta$ | $\Delta'$ | $\Delta$ | $\Delta'$ |
| DLPC | 1.3 | 3.1 | 1.4 | 2.8 | 1.2 | 2.3 | 3.6 | 3.8 | 0.9 | 1.1 | 1.0 | 0.1 | 4.9 | 3.9 |
| DDPC | 49.4 | 45.9 | 12.8 | 7.7 | 9.4 | 5.3 | 51.2 | 47.7 | 27.8 | 23.8 | 12.6 | 8.7 | 58.6 | 42.9 |
| Tween 20 | 1.3 | 13.8 | 2.9 | 14.4 | 2.8 | 21.5 | 5.2 | 20.7 | 5.3 | 13.5 | 2.0 | 7.6 | 12.8 | 17.5 |
| Tween 40 | 1.3 | 10.8 | 3.0 | 10.0 | 2.1 | 8.0 | 1.8 | 8.0 | 1.3 | 4.4 | 0.6 | 5.4 | 5.0 | 7.9 |
| Tween 60 | 2.1 | 4.9 | 2.2 | 4.3 | 2.5 | 4.0 | 2.4 | 4.3 | 0.6 | 2.5 | 1.2 | 3.4 | 6.9 | 4.9 |
| Tween 80 | 1.0 | 6.4 | 1.7 | 6.8 | 2.3 | 1.7 | 2.1 | 3.5 | 1.2 | 1.9 | 1.2 | 4.2 | 11.7 | 5.5 |
| PEG 10 castor oil | 1.0 | 3.4 | 2.9 | 2.9 | 3.7 | 4.4 | 2.2 | 5.4 | 1.5 | 2.3 | 0.9 | 2.0 | 3.6 | 11.0 |
| SPAN 40 | 7.5 | 16.7 | 7.5 | 18.7 | 6.4 | 16.9 | 7.8 | 17.3 | 3.8 | 7.2 | 7.3 | 12.3 | 3.0 | 6.8 |
| SPAN 60 | 12.6 | 15.8 | 18.4 | 15.5 | 11.9 | 15.2 | 14.1 | 13.4 | 10.4 | 11.4 | 13.6 | 13.5 | 3.7 | 8.1 |
| SPAN 80 | 8.8 | 13.1 | 6.0 | 5.6 | 1.5 | 3.4 | 3.0 | 5.5 | 2.8 | 3.3 | 18.6 | 22.9 | 3.9 | 10.0 |
| SPAN 65 | 3.3 | 3.1 | 4.4 | 3.9 | 16.2 | 13.6 | 6.7 | 6.3 | 12.8 | 11.0 | 4.4 | 1.5 | 2.4 | 0.8 |
| SPAN 85 | 10.4 | 10.4 | 6.4 | 6.2 | 4.2 | 5.1 | 5.6 | 7.0 | 2.9 | 3.6 | 1.3 | 2.9 | 1.5 | 2.8 |
| α-Tocopherol | 10.4 | 23.5 | 4.0 | 20.2 | 3.1 | 4.5 | 3.3 | 6.3 | 1.7 | 4.3 | 1.7 | 5.1 | 2.1 | 4.8 |
| Monoolein | 4.0 | 4.6 | 2.8 | 3.7 | 1.8 | 3.3 | 2.4 | 3.4 | 0.4 | 2.0 | 11.6 | 17.0 | 3.5 | 2.8 |
| Glycerol distearate | 2.5 | 4.6 | 2.4 | 4.1 | 3.2 | 4.7 | 2.9 | 4.8 | 3.2 | 3.9 | 4.2 | 3.0 | 1.8 | 2.6 |
| Glycerol dioleate | 5.0 | 4.9 | 3.0 | 4.4 | 2.1 | 3.5 | 3.4 | 3.5 | 2.6 | 1.5 | 3.8 | 3.0 | 3.7 | 2.6 |
| α,α dilaurin | 4.1 | 10.2 | 3.6 | 5.9 | 1.5 | 3.2 | 2.3 | 3.1 | 1.2 | 0.6 | 3.8 | 4.8 | 2.0 | 1.4 |

$\Delta = (Lc_{4.5} - Lc_{7.4}) - (La_{4.5} - La_{7.4})$
$\Delta' = Lc_{4.5} - (La_{4.5} + Lb_{4.5})$
$Lc_{pH}$: a leakage of a complex of a pH sensitive compound and an amphipathic substance at a given pH
$La_{pH}$: a leakage of a pH sensitive compound alone at a given pH
$Lb_{pH}$: a leakage of an amphipathic substance at a given pH

TABLE 9

Evaluation of functional carriers obtained by combinations of pH sensitive compounds (6400 nmol) and amphipathic substances (1000 nmol) (leaching test) (n = 1 in the test)

| | Deoxycholic acid | | Cholic acid | | Ursodeoxy-cholic acid | | Chenoxy-cholic acid | | Hyodeoxy-cholic acid | | Glycodeoxy-cholic acid | | Glycyrrhizic acid | |
|---|---|---|---|---|---|---|---|---|---|---|---|---|---|---|
| | $\Delta$ | $\Delta'$ | $\Delta$ | $\Delta'$ | $\Delta$ | $\Delta'$ | $\Delta$ | $\Delta'$ | $\Delta$ | $\Delta'$ | $\Delta$ | $\Delta'$ | $\Delta$ | $\Delta'$ |
| DLPC | 71.5 | 80.4 | 44.3 | 49.3 | 64.2 | 57.8 | 46.2 | 62.0 | 8.0 | 11.7 | 49.9 | 52.2 | 62.5 | 61.0 |
| DDPC | 25.2 | 54.4 | 34.1 | 67.1 | 35.5 | 60.9 | *5.3 | 9.9 | 34.3 | 63.9 | 41.7 | 64.7 | 43.4 | 66.6 |
| Tween 20 | 2.5 | 21.6 | 7.2 | 14.2 | 16.8 | 22.6 | *3.7 | 17.6 | 16.9 | 32.8 | 9.0 | 28.0 | 15.0 | 26.8 |
| Tween 40 | 47.8 | 51.9 | 16.3 | 27.3 | 46.5 | 45.3 | 14.7 | 57.8 | 70.4 | 78.0 | 5.5 | 16.6 | 31.9 | 36.6 |
| Tween 60 | 65.2 | 67.6 | 3.0 | 7.2 | 46.9 | 43.2 | 31.2 | 59.2 | 85.1 | 90.8 | 4.3 | 7.8 | 55.2 | 57.1 |
| Tween 80 | 58.0 | 63.4 | 10.6 | 16.9 | 50.6 | 43.3 | 22.9 | 52.4 | 77.2 | 83.5 | 8.6 | 15.0 | 49.4 | 49.6 |
| PEG 10 castor oil | 74.1 | 77.3 | 4.5 | 12.8 | 12.6 | 7.4 | 36.3 | 56.5 | 57.5 | 61.6 | 4.9 | 7.6 | 24.7 | 24.0 |
| SPAN 40 | 75.1 | 70.2 | 13.5 | 40.2 | 8.6 | 3.5 | 38.9 | 52.3 | 2.2 | 13.9 | 16.7 | 11.0 | 4.4 | 6.7 |
| SPAN 60 | 74.9 | 70.0 | 34.1 | 39.9 | 16.5 | 6.3 | 33.8 | 47.5 | 7.5 | 10.5 | 13.1 | 8.0 | 8.3 | 3.1 |
| SPAN 80 | 72.8 | 71.7 | 31.2 | 60.2 | 9.2 | 2.4 | 32.0 | 47.0 | 25.9 | 27.2 | 6.2 | 2.0 | 6.6 | 4.0 |
| SPAN 65 | 72.6 | 66.1 | 33.8 | 35.7 | 38.0 | 24.6 | 27.3 | 49.2 | 6.7 | 4.3 | 12.5 | 6.3 | 17.4 | 8.3 |
| SPAN 85 | 73.8 | 70.9 | 48.2 | 56.6 | 13.1 | 4.5 | 31.9 | 43.4 | 33.0 | 33.5 | 6.6 | 2.9 | 22.8 | 16.9 |
| α-Tocopherol | 69.8 | 69.0 | 7.9 | 27.2 | 5.0 | 1.1 | 6.2 | 16.0 | 22.4 | 22.7 | 5.7 | 2.2 | 7.1 | 7.0 |
| Monoolein | 40.7 | 59.0 | 31.0 | 39.5 | 9.7 | 2.4 | 16.9 | 42.8 | 34.7 | 37.4 | 2.0 | 11.3 | 8.2 | 36.7 |
| Glycerol distearate | 78.1 | 73.3 | 10.9 | 18.2 | 22.0 | 14.0 | 32.3 | 57.5 | 3.9 | 7.4 | 6.2 | 1.4 | 49.0 | 42.2 |
| Glycerol dioleate | 75.6 | 72.4 | 8.4 | 28.6 | 11.8 | 2.0 | 31.3 | 41.0 | 29.7 | 30.0 | 10.5 | 6.0 | 6.5 | 1.3 |
| α,α dilaurin | 61.7 | 61.0 | 15.9 | 42.7 | 12.7 | 2.3 | 29.5 | 43.3 | 38.8 | 44.2 | 16.7 | 18.9 | 50.6 | 57.9 |

$\Delta = (Lc_{4.5} - Lc_{7.4}) - (La_{4.5} - La_{7.4})$
$\Delta' = Lc_{4.5} - (La_{4.5} + Lb_{4.5})$
$Lc_{pH}$: a leakage of a complex of a pH sensitive compound and an amphipathic substance at a given pH
$La_{pH}$: a leakage of a pH sensitive compound alone at a given pH
$Lb_{pH}$: a leakage of an amphipathic substance at a given pH
As to the combinations marked by *, the results of the test based on 30 minutes incubation are shown.

From Tables 8 and 9, it has been found that for any of the combinations, Δ and Δ', which are indices for having a significant effect, provide plus values, respectively, the carriers obtained from the combinations of Tables 8 and 9 have a pH sensitive function.

(11) Confirmation of Membrane Fusion Against Cell Membrane

From the results of the foregoing (3), (5), (6), (9) and the like, it has been shown that an illustrative pH sensitive carrier develops the membrane disruptive function promoting effect and membrane fusion function promoting effect in a weakly acidic environment. Fusion between a pH sensitive carrier and a cell membrane was confirmed. In more detail, a fluorescence-labeled pH sensitive carrier and HeLa cells were subjected to short time incubation in media adjusted to pHs of 7.4 and 5.3, respectively, and staining of a cell surface membrane was checked thereby confirming the fusion between the pH sensitive carrier and the cell membrane.

Figure 15:
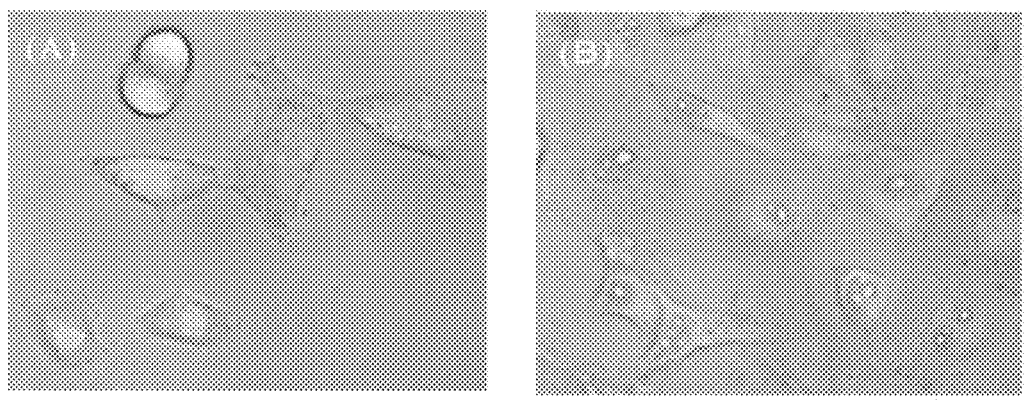
FIG. 15 is a micrograph obtained in case where a fluorescence-labeled DLPC-deoxycholate complex and HeLa cell are incubated in media of a pH of 7.4 in (A) and a pH of 5.3 in (B), and also shows a fluorescence intensity of the cells evaluated by use of a flow site meter in (C).
Figure 15:
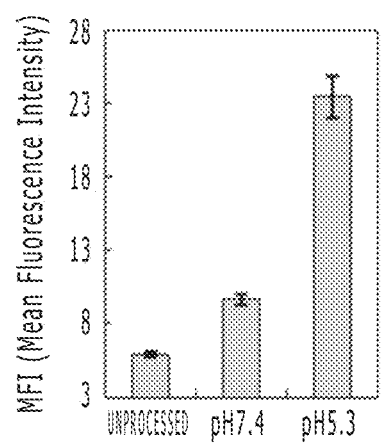

As a result, the fluorescence was observed as a point of origin or in a region close to the nucleus at a pH of 7.4 (FIG. 15(A)). This indicates that the pH sensitive carrier is taken up by the cells and exists in the endosome and lysosome. It will be noted that a similar image as observed as with the case of a fluorescence-labeled amphipathic substance alone (data not shown).

On the other hand, there was observed an image wherein the shape of fluorescence and the shape of the cell coincided with each other in the entire visual field at a pH of 5.3 (FIG. 15(B)). It is theorized that the fluorescence-labeled pH sensitive carrier underwent membrane fusion with the cell membrane on the cell surface, for which the fluorescence spread in the form of cell.

From the above results, it has been revealed that the pH sensitive carrier develops a membrane fusion function promoting effect a weakly acidic environment in the medium and undergoes membrane fusion with the cell membrane on the cell surface.

When the cell fluorescence intensity was evaluated by use of a flow cytometer, the incubated cells showed a great fluorescence intensity at a pH of 5.3 (FIG. 15(C)). It is considered that the results rely on the fluorescence-labeled pH sensitive carrier undergoing membrane fusion in large amounts. Thus, it has been shown that the pH sensitive carrier is able to undergo membrane fusion with an actual cell membrane in an efficient manner.

(12) Influence of the Incorporation of a Peptide and a Protein on the Effect Development It has been investigated to incorporate a peptide or a protein having physiological activity through hydrophobic association for use as DDS. This seems to be a promising method of the present carrier. Hence, influences of the incorporation of physiologically active substances on the effect development of the carrier were checked using OVA 257-264 (SIINFEKL, purchased from PH Japan) as a model peptide and OVA (purchased from Sigma-Aldrich Co. LLC.) as a model protein.

Initially, in order to evaluate the incorporation of the physiologically active substance, the particle size and polydispersity index (PDI) of a carrier where the peptide or protein (192 μg) was incorporated in a DLPC-deoxycholate complex (1000 nmol:1600 nmol) were measured (Table 10).

Figure 16:
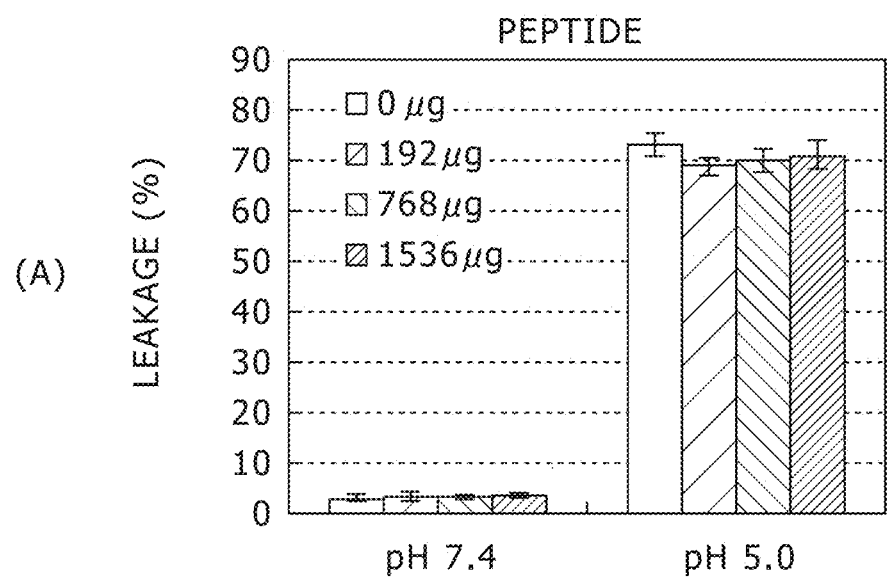
FIG. 16 is a graph showing leakages of carriers incorporating a peptide in (A) and a protein in (B) at pHs of 7.4 and 5.0, respectively.
Figure 16:
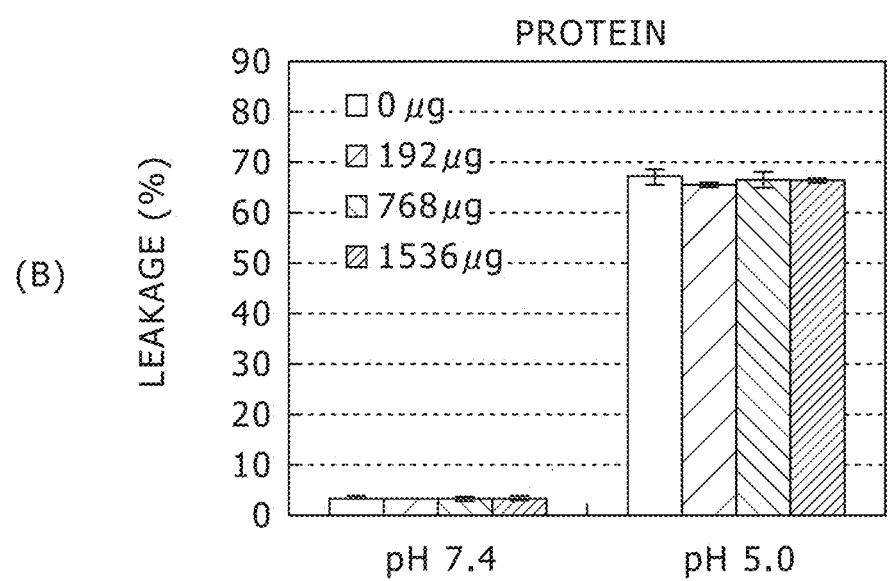

Next, the leakages of the carriers incorporated with different amounts of peptide (A) or protein (B) relative to 1000 nmol of DLPC and 1600 nmol of deoxycholate acid were determined. In FIG. 16, the results of leakages of (A) peptide and (B) protein-containing carriers at pHs of 7.4 and 5.0 are shown. The values in FIG. 16 are each an average value of three different measurements and ± is SD.

Figure 17:
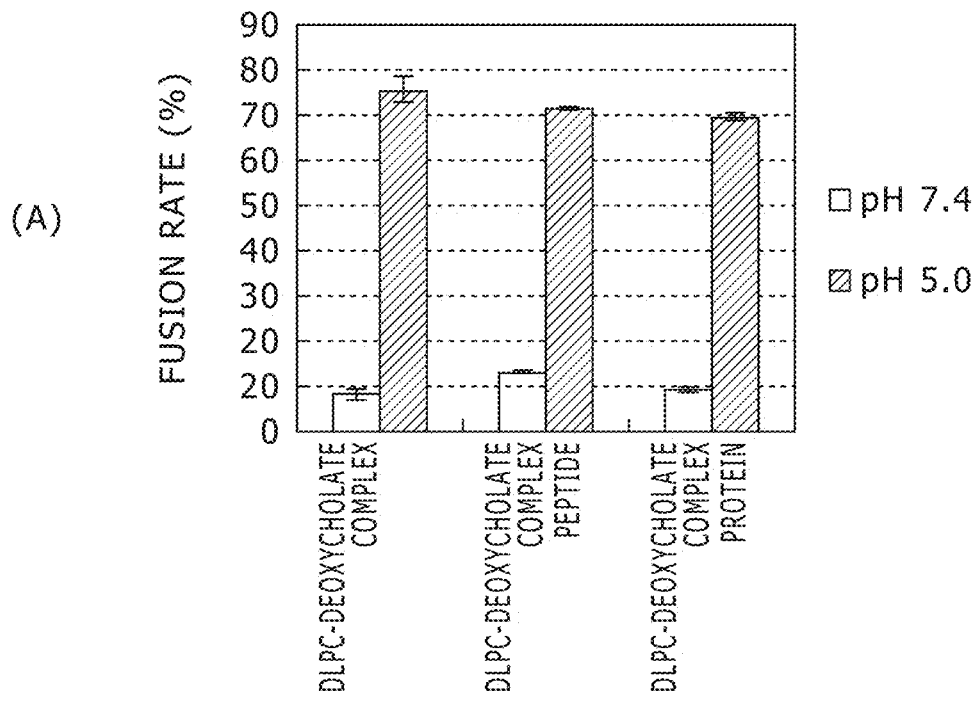
FIG. 17 is a graph showing fusion rates of DLPC-deoxycholate complexes in (A) and DLPC-ursodeoxycholate complexes in (B), both incorporated with a peptide and a protein, respectively, at pHs of 7.4 and 5.0.
Figure 17:
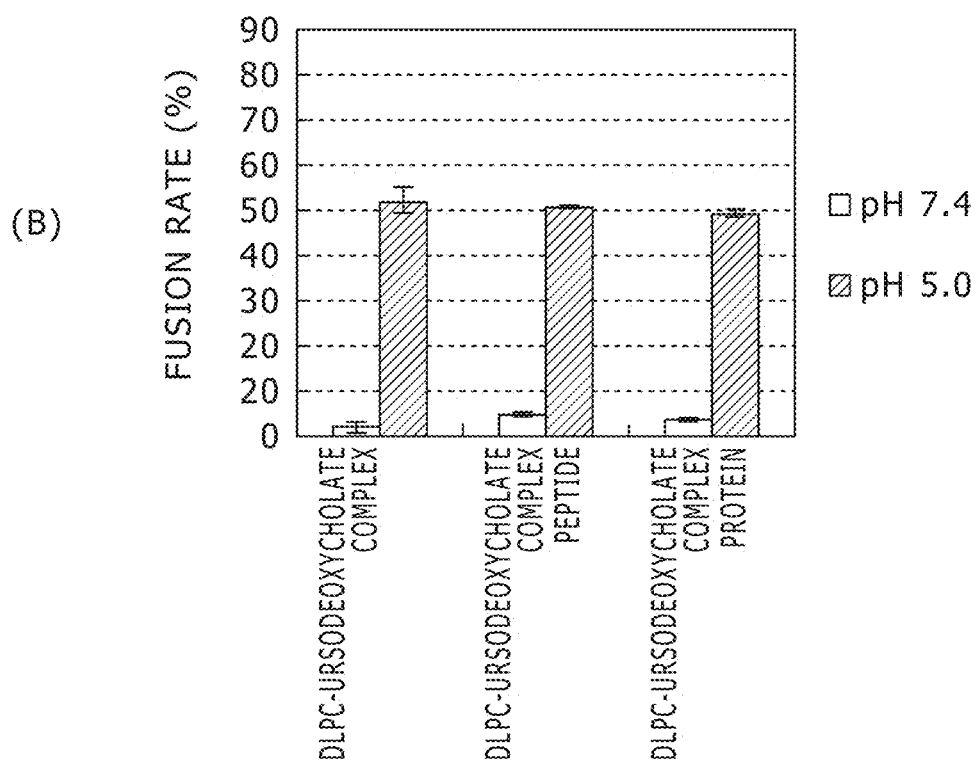

Moreover, the fusion rate of each of the carriers incorporated with 768 μg of the peptide or protein relative to 1000 nmol of DLPC and 1600 nmol of (A) deoxycholic acid or (B) ursodeoxycholic acid was checked. In FIG. 17, there are shown the results of the fusion rates of (A) deoxycholic acid and (B) ursodeoxycholic acid at pHs of 7.4 and 5.0. The values in FIGS. 17(A) and (B) are each an average value of three different measurements and ± is SD.

TABLE 10

| Particle size and PDIs. | | |
|---|---|---|
| DLPC-deoxy | Diameter (nm) | PDI |
| Micelle only | 43.3 ± 0.3 | 0.09 ± 0.01 |
| peptide | 56.0 ± 0.9 | 0.21 ± 0.01 |
| OVA-protein | 71.6 ± 0.5 | 0.04 ± 0.02 |

The value is an average as a result of five measurements and ± is SD.
Micelle only: DLPC-deoxycholate complex alone
peptide: peptide-containing DLPC-deoxycholate complex
OVA-protein: OVA-containing DLPC-deoxycholate complex The incorporation of the peptide or protein in the carrier had a tendency to slightly increase the particle size of the carrier (Table 10). Thus, it was suggested that these substances were incorporated in the carrier. On the other hand, as to the leakage being caused, the values were the same as those obtained in the case of no incorporation in any amounts of the peptide or protein (FIGS. 16(A) and (B)) and it was shown that no lowering of the effect of the carrier was caused owing to the incorporation of the peptide or protein.

With respect to the results of the fusion test, similar results were obtained (FIGS. 17(A) and (B)). From these results, it was revealed that the incorporation of the physiologically active substance did not greatly affect the effect development of the carrier.

(13) Delivery to Cellular Cytosol 1

Many reports have been made on carriers, which have such properties as to promote membrane fusion and membrane disruption in a weakly acidic environment and which enables an included or incorporated substance to deliver via an endosome to a cellular cytosol. An attempt was made to deliver a physiologically active substance to a cellular cytosol by use of a formulated pH sensitive carrier.

Figure 18:
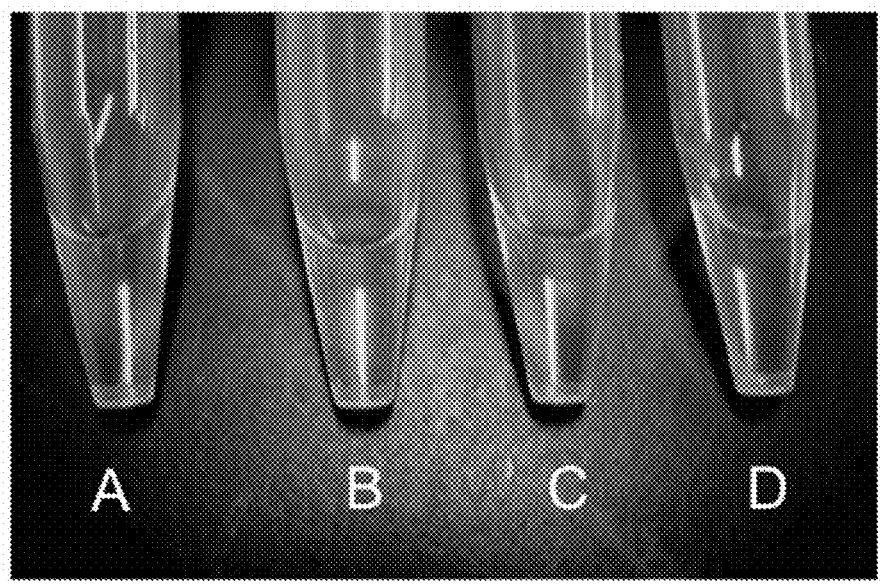
FIG. 18 is a photograph of (A) a solution of a fluorescence-labeled peptide alone, (B) a solution of fluorescence-labeled peptide-containing DLPC alone, (C) a solution of a fluorescence-labeled peptide-containing DLPC-deoxycholate complex, and (D) a solution of a fluorescence-labeled peptide-containing DLPC-ursodeoxycholate complex.

A carrier was prepared using 140 μg/mL of a fluorescence-labeled peptide solution relative to 1000 nmol of DLPC and 1600 nmol of deoxycholic acid or ursodeoxycholic acid. For a control, a carrier was prepared using 140 μg/mL of a fluorescence-labeled peptide solution relative to 1000 nmol of DLPC. In FIG. 18, there is shown a photograph of (A) a solution of a fluorescence-labeled peptide alone, (B) a solution of a fluorescence-labeled peptide-containing DLPC alone, (C) a solution of a fluorescence-labeled peptide-containing DLPC-deoxycholate complex, and (D) a solution of a fluorescence-labeled peptide-containing DLPC-ursodeoxycholate complex.

The solution (B) of the fluorescence-labeled peptide-containing DLPC, the solution (C) of the fluorescence-labeled peptide-containing DLPC-deoxycholate complex, and the solution (D) of the fluorescence-labeled peptide-containing DLPC-ursodeoxycholate complex became weakly fluorescent over the solution (A) of the fluorescence-labeled peptide alone. This is due to the fluorescence-labeled peptide being fixed to the hydrophobic domains of the carrier, thus suggesting that the fluorescence-labeled peptide is incorporated in the carrier.

Next, the delivery of a fluorescence-labeled peptide to the cellular cytosol was attempted. More particularly, 100 µL of each of the fluorescence-labeled peptide-containing samples (A) to (D) described above (14 µg of the fluorescence-labeled peptide/well) was administered into the RAW cells cultured in 1900 µL of a 10% FBS-containing MEM medium and taken up in overnight. The cells were rinsed and subjected to three hours post-incubation, followed by observation of the cells through a fluorescence microscope.

Figure 19:
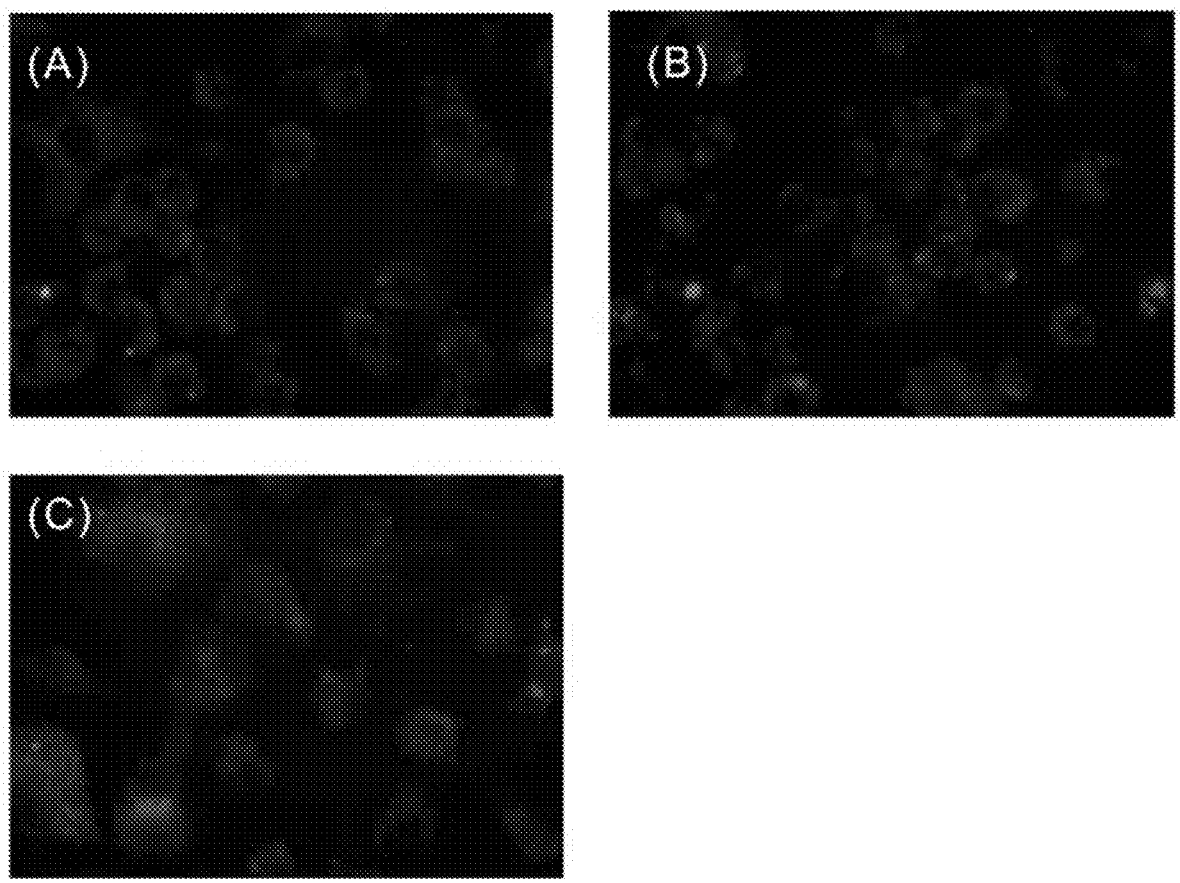
FIG. 19 is a fluorescence micrograph of cells treated with a fluorescence-labeled peptide alone in (A), a fluorescence-labeled peptide-containing DLPC alone in (B) and a fluorescence-labeled peptide-containing DLPC-deoxycholate complex in (C).
Figure 20:
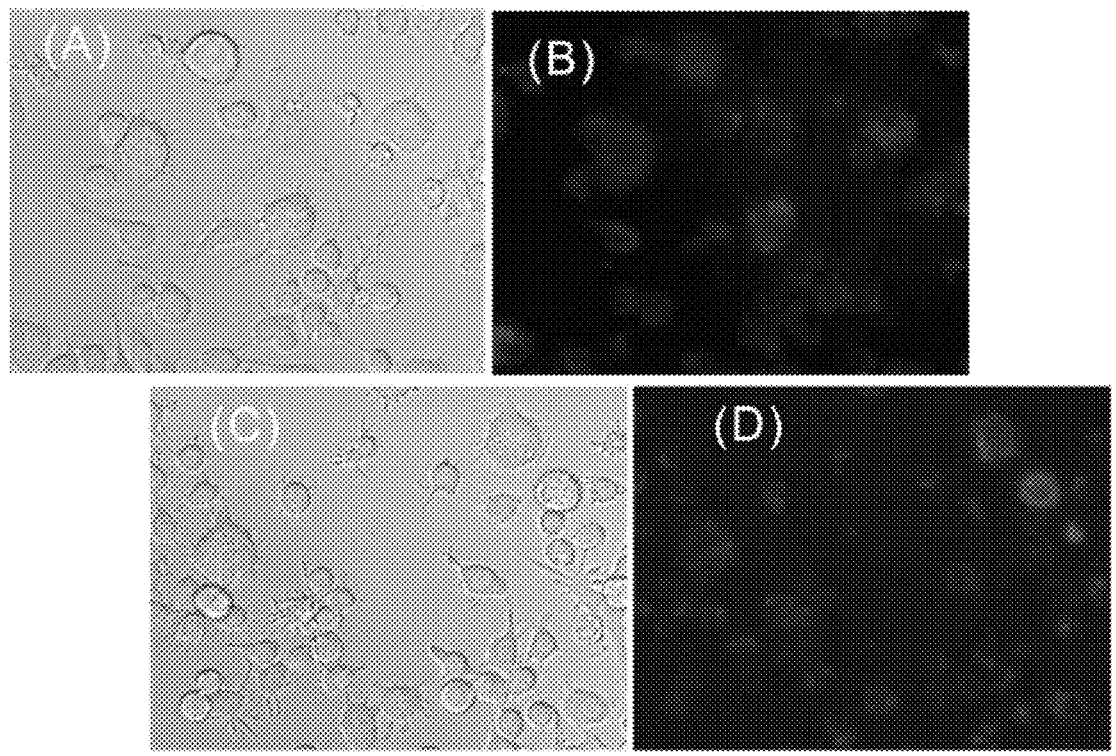
FIG. 20 is a micrograph in (A) and a fluorescence micrograph in (B) of cells treated with a fluorescence-labeled peptide-containing DLPC-deoxycholate complex, and a micrograph in (C) and a fluorescence micrograph in (D) of cells treated with a fluorescence-labeled peptide-containing DLPC-ursodeoxycholate complex, respectively.

In FIG. 19, there are shown fluorescence microphotographs of (A) the fluorescence-labeled peptide alone, (B) the fluorescence-labeled peptide-containing DLPC alone, and (C) the fluorescence-labeled peptide-containing DLPC-deoxycholate complex. In FIG. 20, there are shown (A) a microphotograph and (B) a fluorescence microphotograph of the fluorescence-labeled peptide-containing DLPC-deoxycholate complex, and (C) a microphotograph and (D) a fluorescence microphotograph of the fluorescence-labeled peptide-containing DLPC-ursodeoxycholate complex.

With the case of the fluorescence-labeled peptide alone (A) or the fluorescence-labeled peptide-containing DLPC alone, most of fluorescence was seen as a point of origin, indicating that the fluorescence-labeled peptide remained in the endosome (FIGS. 19(A) and (B)).

On the other hand, with respect to the DLPC-deoxycholate complex (C) incorporated with a fluorescence-labeled peptide, fluorescence was confirmed in substantially all the cells throughout the cell, indicating that the fluorescence-labeled peptide escaped from the endosome and migrated to the cytosol (FIG. 19(C)). Since the carrier was charged negatively and the post incubation was carried out for three hours, it is difficult to consider that this fluorescence is an image obtained by adsorption of the carrier over the entire surface of the cell, but it is considered that the fluorescence-labeled peptide is delivered to the cytosol via the endosome.

With respect to the carrier prepared by use of ursodeoxycholic acid, the fluorescence was observed throughout the cellular cytosol as in the case of deoxycholic acid, and efficient cytosolic delivery was confirmed (FIGS. 20(C) and (D)).

From the foregoing, it was shown that the illustrative pH sensitive carriers enable efficient cytosolic delivery of a physiologically active substance.

(14) Delivery to Cellular Cytosol 2

Subsequently, an attempt was made to deliver a protein to a cellular cytosol. β-gal was chosen as a model protein and incorporated in a pH sensitive carrier. The delivery to the cellular cytosol was evaluated by visualizing enzymatic activity after application to RAW cells and comparing the activities.

Carriers were prepared using 1.4 mg/mL of a β-gal solution relative to 1000 nmol of DLPC and 1600 nmol of deoxycholic acid or ursodeoxycholic acid.

Figure 21:
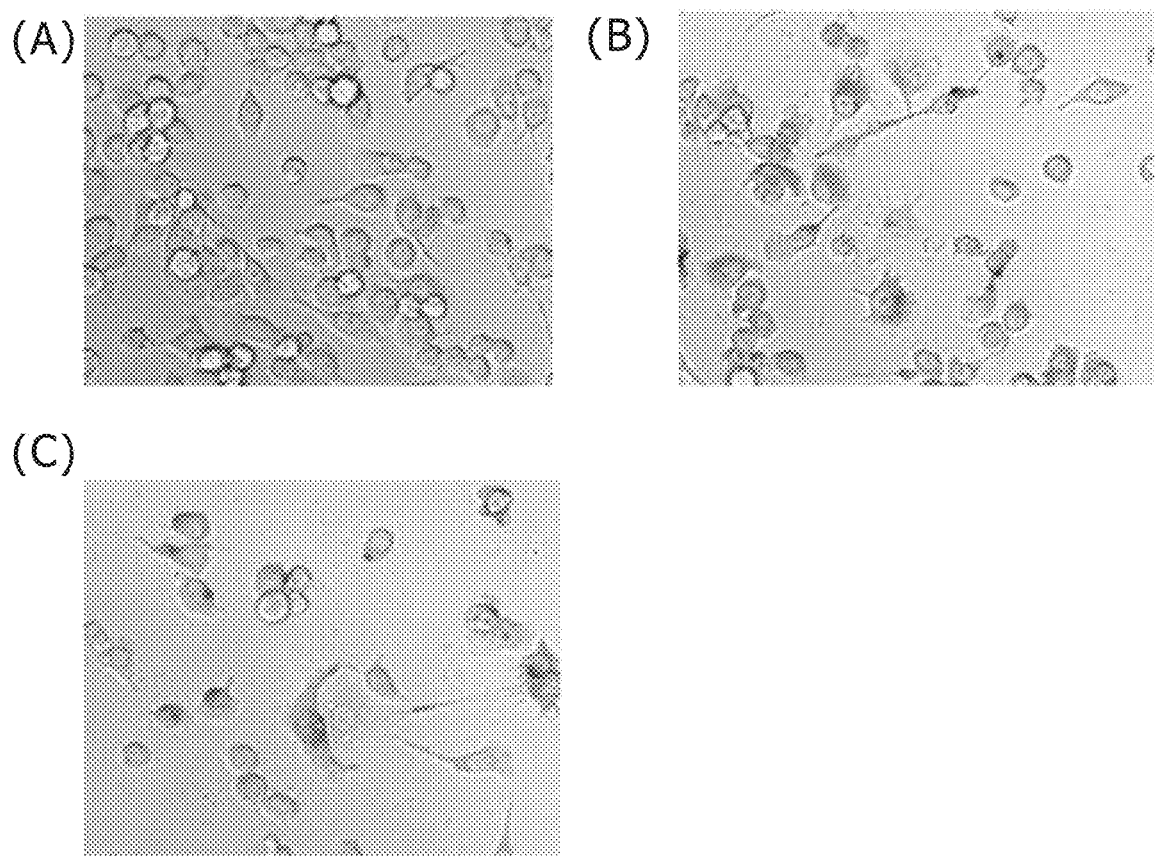
FIG. 21 shows the results of evaluating delivery of β-gal to cellular cytosol and particularly, the results of evaluation on β-gal alone in (A), β-gal-containing DLPC-deoxycholate complex in (B) and β-gal-containing DLPC-ursodeoxycholate complex in (C).

In FIG. 21, there are shown microphotographs of (A) β-gal alone, (B) a β-gal-containing DLPC-deoxycholate complex and (C) a β-gal-containing DLPC-ursodeoxycholate complex.

The cells to which β-gal alone had been added were not stained (FIG. 21(A)). This is due to the β-gal being decomposed in the endosome, indicating no migration to the cellular cytosol. On the other hand, with the case of the incorporation in the pH sensitive carriers, blue staining with β-gal was confirmed (FIGS. 21(B) and (C)), indicating that β-gal escaped from the endosome and migrated to the cellular cytosol while keeping enzymatic activity. According to Vincent M. Rotello et al., J. Am. Chem. Soc. 2010 132(8) 2642-2645, a similar experiment is conducted for the purpose of cytosolic delivery of β-gal and similar results as in the above literature are obtained herein, thus supporting the above discussion.

(15) Delivery to Cellular Cytosol 3

In (13) and (14) above, delivery of a physiologically active substance supported with a pH sensitive carrier was confirmed. Next, an attempt was made to deliver to cellular cytosol when a pH sensitive carrier and a physiologically active substance were respectively independently used. Where a pH sensitive carrier and a physiologically active substance were taken up in the same endosome, the endosome underwent membrane disruption by the membrane disruptive function promoting effect of the pH sensitive carrier. On this occasion, it is considered that the physiologically active substance mixed in the endosome is leached out from the endosome and can be delivered to the cellular cytosol.

Figure 22A:
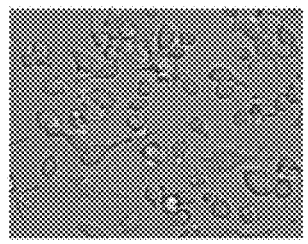
FIG. 22A shows the results of a test of checking the delivery to cellular cytosol when the respective pH sensitive carriers and physiologically active substances are independently used and are, respectively, superposed images of micrographs and fluorescence micrographs obtained by using, in a cell culture environment, of (A) fluorescence-labeled peptide-FITC alone, (B) fluorescence-labeled OVA-FITC alone, (C) a combination of fluorescence-labeled peptide-FITC and EYPC-deoxycholate complex, (D) a combination of fluorescence-labeled OVA-FITC and EYPC-deoxycholate complex, (E) a combination of fluorescence-labeled peptide-FITC and DLPC-deoxycholate complex, (F) a combination of fluorescence-labeled OVA-FITC and DLPC-deoxycholate complex, (G) a combination of fluorescence-labeled peptide-FITC and SPAN 80-deoxycholate complex, (H) a combination of fluorescence-labeled OVA-FITC and SPAN 80-deoxycholate complex, (I) a combination of fluorescence-labeled peptide-FITC and DDPC-deoxycholate complex, and (J) a combination of fluorescence-labeled OVA-FITC and DDPC-deoxycholate complex.
Figure 22A:
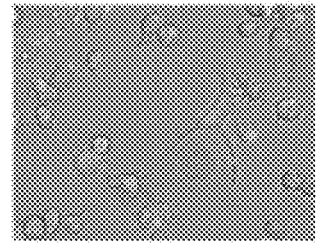
Figure 22A:
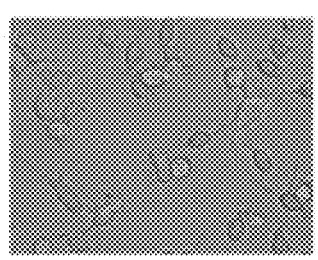
Figure 22A:
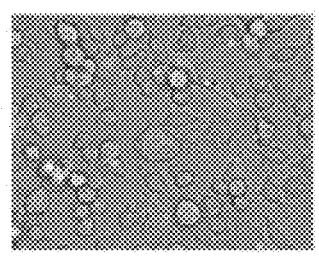
Figure 22A:
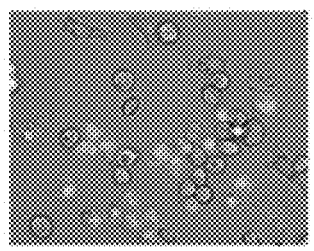
Figure 22A:
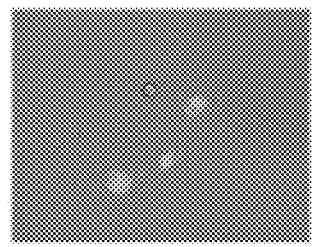
Figure 22A:
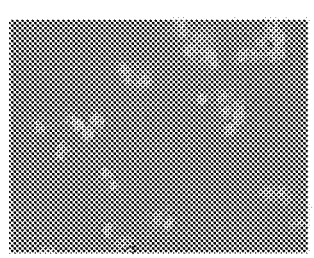
Figure 22A:
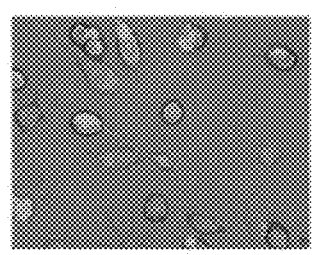
Figure 22A:
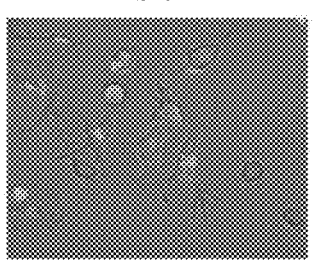
Figure 22A:
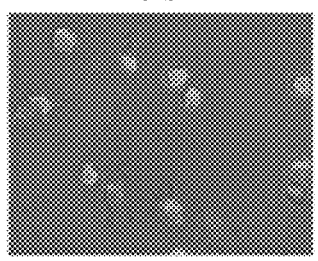

With the case where fluorescence-labeled peptide-FITC was added to RAW cells and also with the case where fluorescence-labeled OVA-FITC was added to RAW cells, the fluorescence in the cell was confirmed as a point of origin, indicating that the fluorescence-labeled peptide-FITC and the fluorescence-labeled OVA-FITC, respectively, remained in the endosome (FIGS. 22A (A) and (B)).

Next, the EYPC-deoxycholate complex, in which the membrane disruption promoting function and membrane fusion promoting function had not been observed in the foregoing (3) and (5), were used in combination with the fluorescence-labeled peptide-FITC or the fluorescence-labeled OVA-FITC. More particularly, a solution of EYPC-deoxycholate complex was further added to a culture solution of RAW cells containing the fluorescence-labeled peptide-FITC. Separately, a solution of EYPC-deoxycholate complex was further added to a culture solution of RAW cells containing the fluorescence-labeled OVA-FITC. In these cases, the fluorescence in the cells was confirmed as a point of origin like the above case, indicating that the fluorescence-labeled peptide-FITC and the fluorescence-labeled OVA-FITC, respectively, remained in the endosome (FIGS. 22A (C) and (D)).

Figure 22B:
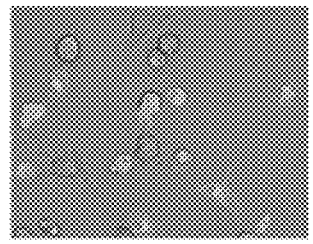
FIG. 22B shows the results of a test of checking the delivery to cell cytoplasm when the respective pH sensitive carriers and physiologically active substances are independently used and are, respectively, superposed images of micrographs and fluorescence micrographs obtained by using, in a cell culture environment, of, (K) a combination of fluorescence-labeled peptide-FITC and PEG-10 castor oil-deoxycholate complex, (L) a combination of fluorescence-labeled OVA-FITC and PEG-10 castor oil-deoxycholate complex, (M) a combination of fluorescence-labeled peptide-FITC and Tween 20-deoxycholate complex, (N) a combination of fluorescence-labeled OVA-FITC and Tween 20-deoxycholate complex, (O) a combination of fluorescence-labeled peptide-FITC and Tween 80-deoxycholate complex, (P) a combination of fluorescence-labeled OVA-FITC and Tween 80-deoxycholate complex, (Q) a combination of fluorescence-labeled peptide-FITC and α-tocopherol-deoxycholate complex, (R) a combination of fluorescence-labeled OVA-FITC and α-tocopherol-deoxycholate complex, (S) a combination of fluorescence-labeled peptide-FITC and DLPC-ursodeoxycholate complex, and (T) a combination of fluorescence-labeled OVA-FITC and DLPC-ursodeoxycholate complex.
Figure 22B:
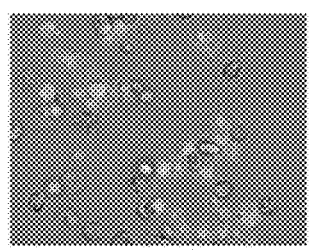
Figure 22B:
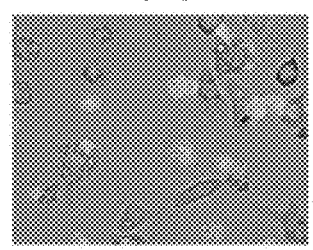
Figure 22B:
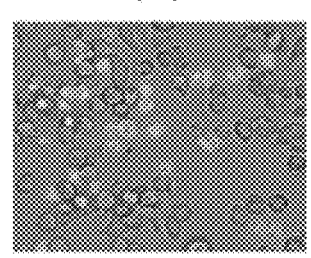
Figure 22B:
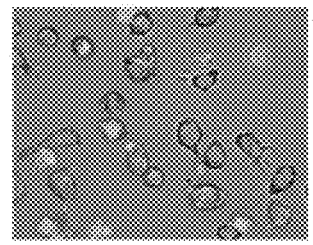
Figure 22B:
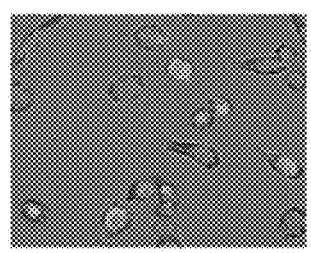
Figure 22B:
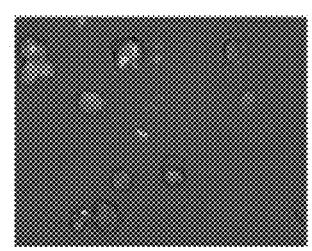
Figure 22B:
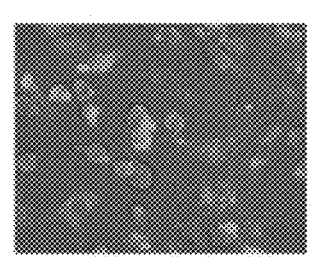
Figure 22B:
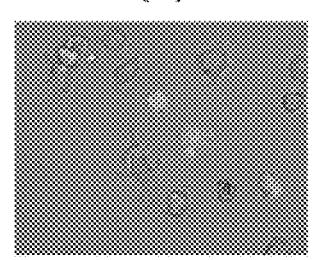
Figure 22B:
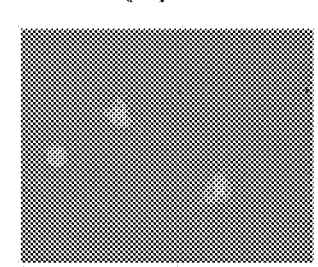
Figure 22C:
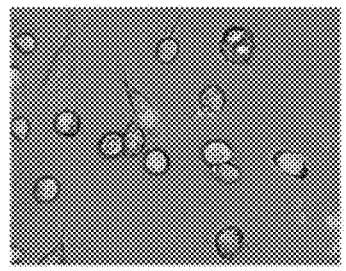
FIG. 22C shows the results of a test of checking the delivery to cell cytoplasm when the respective pH sensitive carriers and physiologically active substances are independently used and are, respectively, superposed images of micrographs and fluorescence micrographs obtained by using, in a cell culture environment, of, (U) a combination of fluorescence-labeled peptide-FITC and DLPC-glycyrrhizic acid complex, (V) a combination of fluorescence-labeled OVA-FITC and DLPC-glycyrrhizic acid complex, (W) a combination of fluorescence-labeled peptide-FITC and DLPC-chenodeoxycholate complex, (X) a combination of fluorescence-labeled OVA-FITC and DLPC-chenodeoxycholate complex, (Y) a combination of fluorescence-labeled peptide-FITC and DLPC-hyodeoxycholate complex, (Z) a combination of fluorescence-labeled OVA-FITC and DLPC-hyodeoxycholate complex, (AA) a combination of fluorescence-labeled peptide-FITC and DLPC-glycodeoxycholate complex, and (AB) a combination of fluorescence-labeled OVA-FITC and DLPC-glycodeoxycholate complex.
Figure 22C:
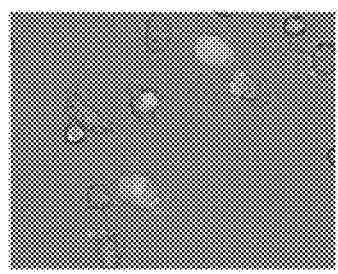
Figure 22C:
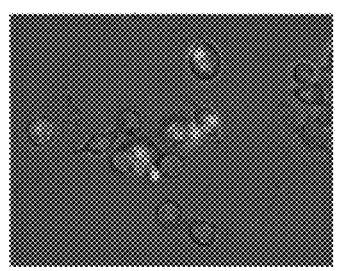
Figure 22C:
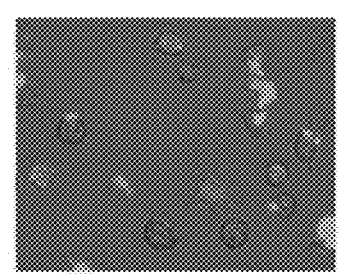
Figure 22C:
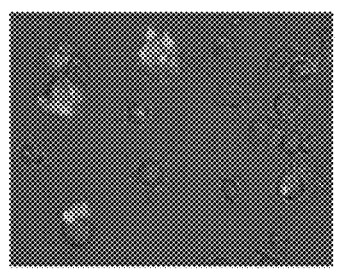
Figure 22C:
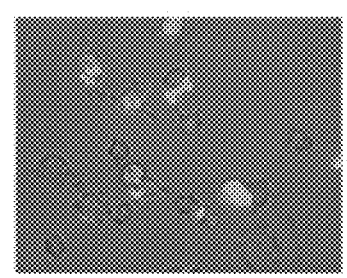
Figure 22C:
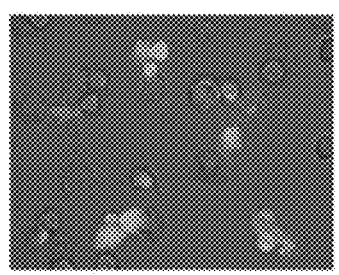
Figure 22C:
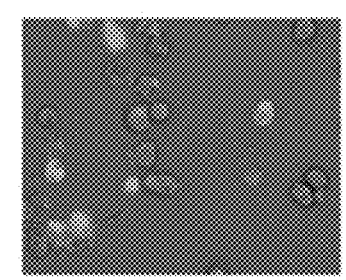

Next, a pH sensitive carrier was used in combination with the fluorescence-labeled peptide-FITC or the fluorescence-labeled OVA-FITC. More particularly, a solution of a pH sensitive carrier having a membrane disruptive function promoting effect was further added to a culture solution of RAW cells containing the fluorescence-labeled peptide-FITC. In addition, a solution of a pH sensitive carrier having a membrane disruptive function promoting effect was further added to a culture solution of RAW cells containing the fluorescence-labeled OVA-FITC. For the pH sensitive carrier, there were used DLPC-deoxycholate complex, SPAN 80-deoxycholate complex, DDPC-deoxycholate complex, polyoxyethylene castor oil (PEG-10 castor oil)-deoxycholate complex, Tween 20-deoxycholate complex, Tween 80-deoxycholate complex, α-tocopherol-deoxycholate complex, DLPC-ursodeoxycholate complex, DLPC-glycyrrhizic acid complex, DLPC-chenodeoxycholate complex, DLPC-hyodeoxycholate complex, and DLPC-glycodeoxycholate complex. The respective pH sensitive carriers were prepared using 160 nmol of a pH sensitive compound and 100 nmol of an amphipathic substance. In these cases, fluorescence was recognized throughout the cellular cytosol (FIG. 22A (E) to (J), FIG. 22B (K) to (T) and FIG. 22C (U) to (AB)).

Accordingly, it was shown that even when a physiologically active substance was used independently of pH sensitive carriers having a membrane disruptive function promoting effect (not supported), delivery to cellular cytosol could be made.

What is claimed is:

1. A method for treating tumor or inflammation in a patient in need thereof which comprises:

administering a pH sensitive drug which comprises a pH sensitive carrier which comprises at least one amphipathic substance, and a physiologically active substance supported in the pH sensitive carrier to induce the pH sensitive carrier to develop a membrane disruptive function and to deliver the physiologically active substance to the site, said pH sensitive carrier including at least one pH sensitive compound selected from the group consisting of deoxycholic acid, cholic acid, ursodeoxycholic acid, chenodeoxycholic acid, hyodeoxycholic acid, C27 bile acid, glycodeoxycholic acid, glycyrrhizic acid, glycyrrhetinic acid and salts thereof, and said at least one amphipathic substance being at least one selected from the group consisting of a phosphatidylcholine having 10 to 12 carbon atoms, a polyoxyethylene sorbitan monofatty acid ester having 12 to 18 carbon atoms, a sorbitan fatty acid ester having 16 to 18 carbon atoms, glycerol monooleate, glycerol dilaurate, glycerol distearate, glycerol dioleate, polyoxyethylene castor oil and α-tocopherol, and is capable of developing a membrane disruptive function promoting effect, and the pH sensitive compound being present in an amount not less than 10 moles per 100 moles of the amphipathic substance.

2. The method as defined in claim 1, wherein the pH sensitive compound and the amphipathic substance form micellar particles.

3. The method as defined in claim 2, wherein the particle size is 10 to 200 nm.

4. The method as defined in claim 1, wherein when a leakage of the pH sensitive compound alone in a leaching test is taken as La, a leakage of the amphipathic substance alone taken as Lb, a leakage of the pH sensitive carrier taken as Lc, leakages at a pH of 7.4, respectively, taken as Lc7.4, La7.4 and Lb7.4, and leakages at a pH of 5.0 or 4.5, respectively, taken as Lcx, Lax and Lbx, Δ represented by the following formula (1) is not smaller than 5 and Δ' represented by the following formula (2) is not smaller than 5:

$$\Delta = (Lcx - Lc7.4) - (Lax - La7.4) \quad \text{Equation (1)}$$

$$\Delta' = Lcx - (Lax + Lbx) \quad \text{Equation (2).}$$

5. The method as defined in claim 1, wherein the physiologically active substance is made of a protein or peptide.

6. A method for treating tumor or inflammation in a patient in need thereof which comprises:

administering a pH sensitive drug composition which comprises a pH sensitive carrier which comprises at least one amphipathic substance, and a physiologically active substance to induce the pH sensitive carrier to develop a membrane disruptive function and to deliver the physiologically active substance to the site, said pH sensitive carrier including at least one pH sensitive compound selected from the group consisting of deoxycholic acid, cholic acid, ursodeoxycholic acid, chenodeoxycholic acid, hyodeoxycholic acid, C27 bile acid, glycodeoxycholic acid, glycyrrhizic acid, glycyrrhetinic acid and salts thereof, and said at least one amphipathic substance being at least one selected from the group consisting of a phosphatidylcholine having 10 to 12 carbon atoms, a polyoxyethylene sorbitan monofatty acid ester having 12 to 18 carbon atoms, a sorbitan fatty acid ester having 16 to 18 carbon atoms, glycerol monooleate, glycerol dilaurate, glycerol distearate, glycerol dioleate, polyoxyethylene castor oil and α-tocopherol, and is capable of developing a membrane disruptive function promoting effect, and the pH sensitive compound being present in an amount not less than 10 moles per 100 moles of the amphipathic substance.

7. The method as defined in claim 6, wherein the pH sensitive compound and the amphipathic substance form micellar particles.

8. The method as defined in claim 7, wherein the particle size is 10 to 200 nm.

9. The method as defined in claim 6, wherein when a leakage of the pH sensitive compound alone in a leaching test is taken as La, a leakage of the amphipathic substance alone taken as Lb, a leakage of the pH sensitive carrier taken as Lc, leakages at a pH of 7.4, respectively, taken as Lc7.4, La7.4 and Lb7.4, and leakages at a pH of 5.0 or 4.5, respectively, taken as Lcx, Lax and Lbx, Δ represented by the following formula (1) is not smaller than 5 and Δ' represented by the following formula (2) is not smaller than 5:

$$\Delta = (Lcx - Lc7.4) - (Lax - La7.4) \quad \text{Equation (1)}$$

$$\Delta' = Lcx - (Lax + Lbx) \quad \text{Equation (2).}$$

10. The method as defined in claim 6, wherein the physiologically active substance is made of a protein or peptide.

* * * * *